(12) United States Patent
Stump

(10) Patent No.: US 12,733,946 B2
(45) Date of Patent: Sep. 15, 2026

(54) SHOULDER PROSTHESIS COMPONENTS AND ASSEMBLIES

(71) Applicant: HOWMEDICA OSTEONICS CORP., Mahwah, NJ (US)

(72) Inventor: David R. Stump, Columbia City, IN (US)

(73) Assignee: HOWMEDICA OSTEONICS CORP., Mahwah, NJ (US)

(*) Notice: Subject to any disclaimer, the term of this patent is extended or adjusted under 35 U.S.C. 154(b) by 57 days.

(21) Appl. No.: 18/616,274

(22) Filed: Mar. 26, 2024

(65) Prior Publication Data

US 2024/0225668 A1 Jul. 11, 2024

Related U.S. Application Data

(62) Division of application No. 17/177,596, filed on Feb. 17, 2021, now Pat. No. 11,969,175.

(60) Provisional application No. 62/978,544, filed on Feb. 19, 2020.

(51) Int. Cl.

| | |
|---|---|
| ***A61B 17/17*** | (2006.01) |
| ***A61B 90/00*** | (2016.01) |
| ***A61F 2/46*** | (2006.01) |
| *A61B 17/00* | (2006.01) |

(52) U.S. Cl.

CPC .......... *A61B 17/1778* (2016.11); *A61B 90/03* (2016.02); *A61B 90/08* (2016.02); *A61F 2/4612* (2013.01); *A61B 2017/00526* (2013.01); *A61B 2090/036* (2016.02); *A61B 2090/0807* (2016.02); *A61F 2002/4681* (2013.01)

(58) Field of Classification Search

CPC ........................................ A61B 17/15–17/158

See application file for complete search history.

(56) References Cited

U.S. PATENT DOCUMENTS

| | | | | |
|---|---|---|---|---|
| 8,123,753 B2 * | 2/2012 | Poncet | A61F 2/4637 | 606/87 |
| 2002/0099381 A1 * | 7/2002 | Maroney | A61B 17/15 | 606/86 R |
| 2005/0021038 A1 * | 1/2005 | Maroney | A61B 17/15 | 606/87 |
| 2006/0004373 A1 * | 1/2006 | Ondrla | A61B 17/15 | 606/87 |
| 2007/0173945 A1 * | 7/2007 | Wiley | A61F 2/4014 | 623/19.13 |

(Continued)

FOREIGN PATENT DOCUMENTS

| | | | |
|---|---|---|---|
| WO | WO-2018045160 A1 * | 3/2018 | A61B 90/13 |

*Primary Examiner* — Zade Coley
(74) *Attorney, Agent, or Firm* — DUANE MORRIS LLP

(57) ABSTRACT

Various embodiments disclosed herein relate to a humeral resection guide. The humeral resection guide can include a cutting block having a side surface and a cutting surface. The cutting surface can be configured to constrain at least one degree of freedom of movement of a cutting instrument during surgical alteration of the humerus. The humeral resection guide can include a boom extending away from the cutting surface of the cutting block, the boom comprising a cut depth adjustment feature disposed along at least a portion of a length of the boom. A method of using the humeral resection guide is disclosed. A method of manufacturing the humeral resection guide is also disclosed.

9 Claims, 37 Drawing Sheets

(56) References Cited

U.S. PATENT DOCUMENTS

2009/0270864 A1* 10/2009 Poncet ...................... A61F 2/40 606/83
2011/0054478 A1* 3/2011 Vanasse ............... A61B 17/809 606/87
2012/0296339 A1* 11/2012 Iannotti .............. A61B 17/1703 606/86 R
2013/0331850 A1* 12/2013 Bojarski ............... A61F 2/4657 606/102
2019/0175298 A1* 6/2019 Muir ...................... A61B 90/35

* cited by examiner 711
712
719
719
709
719
719
719
703

1200
1222
1296B
1212
1282
1282
1213
1278
1274
1230
1202
1258
1378
1374
1214
1204
1218

1200
1226
1216
1230
1202
1238
1234
1204
1218
1222
1210
1208
1206
1242
1370
1214

2506
2508
2520
2516
2512
2510

2508
2522
2518
2524
2505
2516

2250
2254
180
H
103,203,303,503,
603,703,803,903

2200
2204
164
168
103,203,303,503,
603,703,803,903
H 2420
2422
2424
2428
2432
H 2400
2404
2408
2412
H

SHOULDER PROSTHESIS COMPONENTS AND ASSEMBLIES

CROSS-REFERENCE TO RELATED APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

The present application relates to apparatuses and methods for reverse and/or anatomic shoulder prostheses and, in particular, for apparatuses and methods for resecting a humerus and implanting a shoulder prosthesis component in the humerus.

Description of the Related Art

Arthroplasty is the standard of care for the treatment of shoulder joint arthritis. A typical anatomical shoulder joint replacement attempts to mimic anatomic conditions. A metallic humeral stem and a humeral head replacement are attached to the humerus of the arm and replace the humeral side of the arthritic shoulder joint. Such humeral head replacement can articulate with the native glenoid socket or with an opposing glenoid resurfacing device.

For more severe cases, a reverse reconstruction can be employed. In a reverse reconstruction the kinematics of the shoulder joint are reversed by securing a spherical device (sometimes called a glenoid sphere) to the glenoid and implanting a humeral implant with a cavity capable of receiving the glenoid sphere.

In some treatments, the clinician may use a kit that includes many different components and tools for implanting anatomical and reverse anatomical shoulder reconstructions. The use of numerous tools can increase the cost of the treatment procedure, and may unnecessarily complicate the procedure. Accordingly, there remains a continuing need for improved shoulder prosthesis components and assemblies.

SUMMARY OF THE INVENTION

Improved humeral components, kits, assemblies, and methods are needed to provide more robust implantation of the anchor (whether a stemless anchor or a stemmed anchor) into the humerus. Various embodiments disclosed herein relate to improved stemless humeral anchors having elongate distal fins and that serve a bone filling function. Moreover, it can be desirable to utilize a kit that reduces the number of humeral anchors and/or tools used to implant the anchors. Various embodiments disclosed herein relate to kits and systems that provide a shared tooling interface for stemless and stemmed humeral anchors, such that the clinician can use a shared set of tools for implanting stemless and stemmed anchors, and for performing both anatomical and reverse anatomical reconstructions.

In one embodiment, a humeral anchor is disclosed. The humeral anchor can include a distal portion extending proximally from a distal end of the humeral anchor, the distal portion configured to occupy a portion of a metaphysis of a humerus when implanted. The humeral anchor can include a proximal portion extending distally from a proximal end of the humeral anchor. The humeral anchor can include a recess extending distally from the proximal end of the humeral anchor and into the proximal portion. The humeral anchor can include an inner periphery disposed about the recess adjacent to the proximal end of the humeral anchor. The inner periphery can include a concave locking feature disposed in the inner periphery. The inner periphery can include a convex locking feature disposed in the inner periphery, the concave locking feature spaced apart from the convex locking feature.

In some embodiments, the concave locking feature can include a first concave locking feature and a second concave locking feature disposed opposite the first concave locking feature. The first concave locking feature and the second concave locking features can be disposed at medial and lateral portions of the humeral anchor respectively. The convex locking feature can include a first convex locking feature and a second convex locking feature disposed opposite the first convex locking feature. The first convex locking feature and the second convex locking features can be disposed at anterior and posterior portions of the humeral anchor respectively. The concave locking feature can be configured to provide an interference fit for an articular body comprising a concave articular surface. The convex locking feature can include an elongate fin projecting toward the recess. The humeral anchor can include a stemless humeral anchor. The distal portion can include a first section and a second section distal the first section, the second section comprising a fin extending distally from the first section. The second section can include a plurality of fins extending distally from the first section. The first section can include a second recess distal the recess. A stem can extend from the distal end of the humeral anchor.

In another embodiment, a humeral anchor is disclosed. The humeral anchor can include a distal portion extending proximally from a distal end of the humeral anchor, the distal portion configured to occupy a portion of a metaphysis of a humerus when implanted. The humeral anchor can include a proximal portion extending distally from a proximal end of the humeral anchor and having an outer surface that is enlarged to occupy at least a majority of the volume of a metaphysis of a humerus into which the humeral anchor is to be disposed. The proximal portion can have a lateral side configured to be disposed adjacent to a cortical wall of a lateral portion of a humeral metaphysis and a medial side configured to be spaced apart from a cortical wall of a medial side of the humeral metaphysis. The humeral anchor can include a bone compression surface disposed at the proximal end of the humeral anchor, the bone compression surface being disposed about the medial side of the proximal portion and being configured to extend from the medial side of the proximal portion to the cortical wall of the medial side of the humeral metaphysis when implanted in a humerus.

In some embodiments, the bone compression surface can include a flange that extends outward from the proximal end of the proximal portion of the humeral anchor. The flange can include a circular outer periphery having a radius corresponding to a radius of the lateral side of the proximal portion. An annular surface can be disposed at a proximal face of the humeral anchor, the flange comprising a portion of the annular surface of a proximal face. Rotational orientation indicia can be formed on or in the annular surface disposed at the proximal face of the humeral anchor. A recess can extend distally from the proximal end of the humeral anchor and into the proximal portion and an inner periphery disposed about the recess adjacent to the proximal end of the humeral anchor, the inner periphery comprising a locking feature disposed in the inner periphery, the locking features being aligned with the bone compression surface.

In another embodiment, a kit for a shoulder prosthesis is disclosed. The kit can include a first stemless humeral anchor comprising a first distal portion configured to occupy a portion of a metaphysis of a humerus when implanted. The first stemless humeral anchor can comprise a first proximal portion extending proximally from a proximal end of the first distal portion to a proximal end of the first humeral anchor. The first stemless humeral anchor can comprise a first recess extending from the proximal end of the first humeral anchor into the first proximal portion. The first stemless humeral anchor can comprise a first distally-extending fin, the first fin extending distally from the first distal portion to a distal end of the first humeral anchor, a first height defined between the proximal and distal ends of the first humeral anchor. The kit can include a second stemless humeral anchor comprising a second distal portion configured to occupy a portion of a metaphysis of a humerus when implanted. The second stemless humeral anchor can comprise a second proximal portion extending proximally from a proximal end of the second distal portion to a proximal end of the second humeral anchor. The second stemless humeral anchor can include a second recess extending from the proximal end of the second humeral anchor into the second proximal portion. The second stemless humeral anchor can include a second distally-extending fin, the second fin extending distally from the second distal portion to a distal end of the second humeral anchor, a second height defined between the proximal and distal ends of the second humeral anchor. A ratio of the second height to the first height can be in a range of 1.15 to 2.5.

In some embodiments, the kit can include a first stemmed humeral anchor having an anchor body and a stem extending distally from the anchor body. The kit can include one or more articular components configured to connect to the first and second humeral anchors. The one or more articular components can comprise an anatomic articular component having a rounded, convex surface configured to engage a glenoid surface of the patient. The one or more articular components can include a reverse articular body having a rounded, concave surface.

In another embodiment, a humeral anchor is disclosed. The humeral anchor can comprise an interior surface disposed about a first recess between a first end of the humeral anchor and a second location, and disposed about a second recess between the second location and a third location, the first and second recesses having different volumes. The humeral anchor can comprise a distally-extending fin, the fin extending distally from the third location to a second end of the humeral anchor, the fin having a fin height that is at least 10% of a total height of the humeral anchor.

In some embodiments, the humeral anchor can include a plurality of distally-extending fins extending distally from the third location to the second end. The plurality of fins can include a first fin extending along an inferior direction of the anchor and a second fin having directional components extending along a superior direction and one of an anterior and posterior direction. The humeral anchor can include an inner periphery disposed about the first recess adjacent to the first end of the humeral anchor. The inner periphery can include a concave locking feature disposed in the inner periphery. The inner periphery can include a convex locking feature disposed in the inner periphery, the concave locking feature spaced apart from the convex locking feature.

In another embodiment, a method of implanting a shoulder prosthesis into a patient is disclosed. The shoulder prosthesis can comprise a stemless humeral anchor having an anchor body and a plurality of fins extending distally from the anchor body. The method can include removing a portion of a humerus of the patient to form a cavity in the humerus. The method can include orienting the stemless humeral anchor relative to the humerus such that a first fin of the plurality of fins is oriented along an inferior direction and a second fin of the plurality of fins is oriented to have directional components along a superior direction and one of an anterior and posterior direction. The method can include inserting the stemless humeral anchor into the cavity of the humerus.

In some embodiments, the method can include orienting the stemless humeral anchor relative to the humerus such that the second fin is oriented to have directional components along the superior direction and the anterior direction. The method can further comprise orienting the stemless humeral anchor relative to the humerus such that a third fin of the plurality of fins is oriented to have directional components along the superior direction and the posterior direction. The first and second fins can be angled relative to one another by a first angle, wherein the second and third fins are angled relative to one another by a second angle equal to the first angle. The method can include resecting the humerus to form a resection surface prior to removing the portion of the humerus. Removing the portion of the humerus can comprise reaming the humerus to form the cavity. The method can include drilling a second cavity distal to and having a smaller diameter relative to the cavity. The method can include connecting an articular body to the stemless humeral anchor.

In another embodiment, a humeral anchor is disclosed. The humeral anchor can include a distal portion extending proximally from a distal end of the humeral anchor, the distal portion extending along a longitudinal axis of the humeral anchor, the distal portion being tapered inwardly along the longitudinal axis toward the distal end of the humeral anchor. The humeral anchor can include a proximal portion extending distally from a proximal end of the humeral anchor. The humeral anchor can include a recess extending distally from the proximal end of the humeral anchor and into the proximal portion. The humeral anchor can include an inner periphery disposed about the recess adjacent to the proximal end of the humeral anchor. The inner periphery can comprise a concave locking feature disposed in the inner periphery. The inner periphery can comprise a convex locking feature disposed in the inner periphery, the concave locking feature spaced apart from the convex locking feature.

In some embodiments, the concave locking feature can include a first concave locking feature and a second concave locking feature disposed opposite the first concave locking feature. The first concave locking feature and the second concave locking features can be disposed at medial and lateral portions of the humeral anchor respectively. The convex locking feature can include a first convex locking feature and a second convex locking feature disposed opposite the first convex locking feature. The first convex locking feature and the second convex locking features can be disposed at anterior and posterior portions of the humeral anchor respectively. The concave locking feature can be configured to provide an interference fit for an articular body comprising a concave articular surface. The convex locking feature can comprise an elongate fin projecting toward the recess.

In another embodiment, a humeral anchor is disclosed. The humeral anchor can include a distal portion extending proximally from a distal end of the humeral anchor, the distal portion extending along a longitudinal axis of the humeral anchor. The humeral anchor can include a proximal portion extending distally from a proximal end of the humeral anchor and having an outer surface that is enlarged to occupy at least a majority of the volume of a metaphysis of a humerus into which the humeral anchor is to be disposed. The proximal portion can have a lateral side configured to be disposed adjacent to a cortical wall of a lateral portion of a humeral metaphysis us and a medial side configured to be spaced apart from a cortical wall of a medial side of the humeral metaphysis. The humeral anchor can include a bone compression surface disposed adjacent to the proximal end of the humeral anchor, the bone compression surface being disposed about only the medial side of the proximal portion and being configured to extend from the medial side of the proximal portion to the cortical wall of the medial side of the humeral metaphysis when implanted in a humerus.

In some embodiments, the bone compression surface can comprise a flange that extends outward from the proximal end of the proximal portion of the humeral anchor. The flange can comprise a circular outer periphery having a radius corresponding to a radius of the lateral side of the proximal portion. An annular surface can be disposed at a proximal face of the humeral anchor, the flange comprising a portion of the annular surface of a proximal face. Rotational orientation indicia can be formed on or in the annular surface disposed at the proximal face of the humeral anchor. A recess can extend distally from the proximal end of the humeral anchor and into the proximal portion and an inner periphery disposed about the recess adjacent to the proximal end of the humeral anchor, the inner periphery comprising a locking feature disposed in the inner periphery, the locking features being aligned with the bone compression surface.

In another embodiment, a humeral anchor is disclosed. The humeral anchor can include a proximal portion having an enlarged outer surface extending distally from a proximal end of the humeral anchor. The humeral anchor can include a distal portion extending between the proximal portion and a distal end of the humeral anchor, the distal portion extending along a longitudinal axis of the humeral anchor. The distal portion can include a circular periphery at a first location along the longitudinal axis of the humeral anchor adjacent to the distal end. The distal portion can include an oblong periphery at a second location disposed between the first location and the proximal end of the humeral anchor. The distal portion can comprise an at least partially polygonal periphery at a third location disposed between the second location and the proximal end of the humeral anchor. The distal portion can comprise an anti-rotation fin disposed at an edge of the at least partially polygonal periphery.

In some embodiments, one or more circular peripheries are disposed along a length of the humeral anchor from the distal end to the first location. The oblong periphery can comprise a first dimension in an anterior-posterior direction and a second dimension in a medial lateral direction, the second dimension being larger than the first dimension. The at least partially polygonal periphery can comprise a curved convex side configured to be oriented laterally and a generally anterior-posterior oriented side disposed between ends of the convex side. The anti-rotation fin can comprise a projection extending in a medial direction from the generally anterior-posterior oriented side. The at least partially polygonal periphery can be in a cross-section oriented at an angle to a longitudinal axis of the distal portion and parallel to the proximal end of the humeral anchor. The humeral anchor can include a second at least partially polygonal periphery disposed at a fourth location between the third location and the proximal end of the humeral anchor, an anti-rotation fin being disposed at the second at least partially polygonal periphery. The anti-rotation fin can extend continuously from the at least partially polygonal periphery at the third location to the second at least partially polygonal periphery at the fourth location.

In another embodiment, a bone anchor inserter is disclosed. The bone anchor inserter can include a first end and a second end opposite the first end. The bone anchor inserter can include an elongate body extending along a longitudinal axis between the first end and the second end. The bone anchor inserter can include a handle disposed between the first end and the second end, the handle having a first configuration and a second configuration. The bone anchor inserter can include a bone anchor interface disposed at the second end, the bone anchor interface having a bone anchor retention configuration corresponding to the first configuration of the handle and a bone anchor release configuration corresponding to the second configuration of the handle. The bone anchor inserter can include a first impaction head coupled with the elongate body and disposed at a first angle to the longitudinal axis thereof. The bone anchor inserter can include a second impaction head coupled with the elongate body and disposed at a second angle to the longitudinal axis thereof. A force applied to the first impaction head can direct an impacting force to a first bone anchor in a direction aligned with a longitudinal axis of the first bone anchor to embed the first bone anchor in the bone. A force applied to the second impaction head can direct an impacting force to a second bone anchor, the impacting force applied to the second impaction head oriented in a direction perpendicular to a resection plane of the bone to embed the second bone anchor in the bone.

In some embodiments, the first impaction head can be disposed at an angle to the second impaction head. An angle between 35 degrees and 65 degrees can be disposed between the first impaction head and the second impaction head. The handle can be pivotably coupled with the elongate body, the first configuration and the second configuration provided by pivoting the handle. A spring can be disposed between the handle and the elongate body to facilitate placement and retention of the bone anchor interface in the bone anchor retention configuration.

In another embodiments, a bone anchor inserter is disclosed. The bone anchor inserter can include a first end and a second end opposite the first end. The bone anchor inserter can include an elongate body extending between the first end and the second end along a longitudinal axis. The bone anchor inserter can include a bone anchor interface disposed at the second end, the bone anchor interface having a bone anchor retention configuration and a bone anchor release configuration. The bone anchor inserter can include an impaction head coupled with the elongate body and disposed at an end of the elongate body adjacent to the second end and opposite the first end. A force applied to the impaction head can direct an impacting force to a stem portion of a bone anchor, the impacting force applied to the impaction head oriented in a direction aligned with a longitudinal axis of the bone anchor to embed the stem portion of the bone anchor within the medullary canal.

In some embodiments, the impaction head can be oriented at an acute angle to the longitudinal axis of the elongate body.

In another embodiment, a kit is disclosed. The kit can include a stemless bone anchor comprising a first portion configured to be advanced into a metaphysis portion such that the first portion is disposed between a resection surface and a continuous expanse of bone disposed between the resection surface and a medullary canal of the bone. The stemless bone anchor can comprise a second portion opposite the first portion, the second portion comprising an inserter interface. The bone anchor inserter can include a bone anchor comprising a first portion and a second portion opposite the first portion, the first portion comprising a stem configured to be advanced into a diaphysis portion and into a medullary canal of the bone and a second portion, the second portion comprising an inserter interface. The bone anchor inserter can include an inserter comprising a bone anchor interface, the bone anchor interface configured to be engaged with the inserter interface of the stemless bone anchor or with the inserter interface of the bone anchor comprising the stem.

In some embodiments, the inserter can further comprise an impaction head disposed between the bone anchor interface and an end of the inserter opposite to the bone anchor interface, the impaction head configured to transfer an impacting force applied to the impaction head to bone anchor comprising the stem to embed the stem in a medullary canal of a bone. The impaction head can be a first impaction head and further comprising a second impaction head disposed at an angle to the second impaction head. The angle between the first impaction head and the second impaction head can be 45 degrees. The angle between the first impaction head and the second impaction head can be between 35 degrees and 65 degrees. The inserter can comprise a first impaction head and a second impaction head disposed at a first angle to each other. A second inserter can comprise a bone anchor interface, the bone anchor interface configured to be engaged with the inserter interface of the stemless bone anchor or with the inserter interface of the bone anchor comprising the stem, the second inserter comprising a first impaction head and a second impaction head disposed at a second angle relative to each other. Each of the first angle and the second angle can be between 35 degrees and 65 degrees.

In another embodiment, a method is disclosed. The method can include providing a first bone anchor comprising a stemless bone engagement portion, a second bone anchor comprising a stem, the first bone anchor and the second bone anchor each comprising an inserter interface, and an inserter comprising a bone anchor interface configured to engage the inserter interface of either the first bone anchor or the second bone anchor. The method can include engaging the bone anchor interface of the inserter with the inserter interface of the first bone anchor. The method can include advancing the first bone anchor into bone matter exposed at a resection of a bone. The method can include engaging the bone anchor interface of the inserter with the inserter interface of the second bone anchor. The method can include advancing the second bone anchor into bone matter at the resection of the bone to position the stem of the second bone anchor in a medullary canal of the bone.

In some embodiments, advancing the second bone anchor into bone matter can further comprise applying a force to an impaction head of the inserter to apply a force aligned with the second bone anchor to embed the stem in the bone. The impaction head can be a first impaction head and advancing the first bone anchor into bone matter can further comprise applying a force to a second impaction head of the inserter to apply a force perpendicular to the resection of the bone. Advancing the first bone anchor into bone matter can further comprise applying a force to an impaction head of the inserter to apply a force perpendicular to the resection of the bone. The inserter can be a first inserter. The method can comprise providing a second inserter. The first inserter and the second inserter can each have a stemmed anchor impaction head and a stemless anchor impaction head. The first inserter can have a first angle between the stemmed anchor impaction head and the stemless anchor impaction head thereof. The second inserter can have a second angle between the stemmed anchor impaction head and the stemless anchor impaction head thereof. The second angle can be different from the first angle. The method can comprise selecting one of the first inserter or the second inserter based on an angle at which a resection is formed in the bone. The first angle and the second angle can be between 35 degrees to 65 degrees.

In another embodiment, a device for removing bone is disclosed. The device can include a proximal end and a distal end. The device can include a drive shaft at the proximal end of the device, the drive shaft rotatable about a drive shaft axis. The device can include a reamer head rotatable about the drive shaft axis to remove bone. The reamer head can include a distal portion comprising a plurality of radial arms, each of the plurality of radial arms comprising a lateral cutting edge. The reamer head can include a proximal portion comprising a distal facing cutting edge.

In some embodiments, each of the plurality of radial arms can comprise a first flat face and a second flat face opposite the first flat face, the first and second flat faces separated by a thickness. A width of each of the first and second flat faces, measured in a radial direction, can be greater than the thickness. Each of the plurality of arms can comprise a proximal section and a distal section, the proximal section projecting radially outward of the distal section. A guide channel can be configured to receive a guide pin, each of the plurality of radial arms extending radially outward from the guide channel. The proximal portion can comprise a depth stop configured to control an insertion depth of the reamer head, the depth stop being proximal of and extending radially outward of the distal facing cutting edge. The distal facing cutting edge can be positioned radially outward of the plurality of radial arms. The distal facing cutting edge can extend circumferentially around the proximal portion of the reamer head. The distal facing cutting edge can comprise a plurality of cutting teeth. The proximal portion of the reamer head can comprise a plurality of apertures in a proximal face of the reamer head.

In another embodiment, a device for removing bone is disclosed. The device can include a first end and a second end. The device can include a drive shaft at the first end of the device, the drive shaft rotatable about a drive shaft axis. The device can include a reamer head rotatable about the drive shaft axis to remove bone. The reamer head can include an inner portion comprising a lateral facing cutting edge, the inner portion configured to form a first cavity portion in the bone, a second cavity portion at a greater depth than the first cavity portion, and a stepped portion between the first cavity portion and the second cavity portion. An outer portion can be positioned radially outward of the inner portion, the outer portion comprising a distal facing cutting edge, the outer portion configured to form a recessed surface proximal of and at least partially surrounding the first cavity portion.

In some embodiments, a profile of the distal facing cutting edge can be different from a profile of the lateral facing cutting edge. The second cutting edge can comprise a plurality of cutting teeth. A guide channel can be configured to receive a guide pin. The reamer head further can comprise a depth stop configured to control an insertion depth of the reamer head, the depth stop being proximal of and extending radially outward of the distal facing cutting edge.

In another embodiment, a method of removing bone is disclosed. The method can include advancing a reamer toward an end of a bone, the reamer comprising a drive shaft and a reaming head. The method can include driving the reamer about a drive axis of the drive shaft. The method can include forming a cavity in the bone with the reaming head. The cavity can comprise a first cavity portion and a second cavity portion extending a greater depth into the bone than the first cavity portion. The cavity can include a stepped portion between the first cavity portion and the second cavity portion. The method can include forming a recessed surface below a resection plane of the bone with the reaming head, the recessed surface at least partially surrounding the first cavity portion. The method can include positioning an anchor structure of an implant in the cavity in the bone. The method can include positioning a collar of the implant on the recessed surface in the bone.

In some embodiments, forming the cavity in the bone and forming the recessed surface can occur simultaneously. In some embodiments, forming the cavity in the bone and forming the recessed surface can occur sequentially. After forming the cavity in the bone, the recessed surface can be formed in the bone. Advancing the reamer can comprise advancing the reamer along a guide pin. The method can include forming the recessed surface in the bone until a depth stop contacts the resection plane of the bone.

In one embodiment, a humeral resection guide is disclosed. The humeral resection guide can include a cutting block having a side surface configured to face an exterior surface of a humerus and a cutting surface disposed non-parallel relative to the side surface. The cutting surface can be configured to constrain at least one degree of freedom of movement of a cutting instrument during surgical alteration of the humerus. The humeral resection guide can include a boom extending away from the cutting surface of the cutting block, the boom comprising a cut depth adjustment feature disposed along at least a portion of a length of the boom. The humeral resection guide can include a cut depth indicator disposed at a population derived location along the length of the boom. The cut depth indicator can be configured to indicate that the cutting surface is at a target cut depth for the alteration of the humerus when the cut depth indicator is aligned with a support.

In some embodiments, the cut depth adjustment mechanism can comprise a slot extending along at least a portion of the length of the boom. The population derived location of the cut depth indicator can be derived at least in part from image data of a plurality of humeruses. The cut depth indicator can comprise a plurality of markings spaced apart along at least a portion of the length of the boom. The boom can extend away from the cutting block at an obtuse angle relative to the cutting surface. The obtuse angle can be in a range of 130° to 150°. The obtuse angle can be approximately 135°. The obtuse angle can be approximately 145°. The humeral resection guide can include the support. The support can be adjustably connected to the cut depth adjustment mechanism, the support configured to be positioned along the cut depth adjustment mechanism at a plurality of or over a range of locations along the length of the boom. The support can comprise a cross arm and a handle connected to the cross arm, the cross arm extending anteriorly relative to the handle between the handle and the boom such that the boom and the cutting block are spaced anteriorly from the handle by the cross arm. The cross arm can be rotatably coupled to the handle about a longitudinal axis of the handle. The humeral resection guide can include a projection extending distally from the handle and distal of the cutting block, the projection sized and shaped to be inserted into the humerus. The humeral resection guide can include a depth stop at a distal portion of the handle, the depth stop wider than the rod. The cutting block can comprise one or a plurality of pin holes therethrough, the pin hole(s) extending through the side surface to an opposing side face, the opposing side face disposed away from the exterior surface of the humerus when the side surface is positioned against and/or adjacent to the exterior surface of the humerus.

In another embodiment, a method of manufacturing a humeral resection guide is disclosed. The humeral resection guide can include a cutting block and a boom extending from the cutting block at an obtuse angle. The method can include for each humerus of a plurality of humeruses, adjusting the boom relative to a handle assembly such that the cutting block is disposed at a target cut depth for that humerus. The method can include for each humerus of the plurality of humeruses, determining a target location along a length of the boom to which the handle assembly is connected when the cutting block is disposed at the target cut depth. The method can include determining a range of target locations along the length of the boom based at least in part on the determined target locations for the plurality of humeruses. The method can include providing a cut depth indicator on the boom at a target region of the boom based at least in part on the determined range of target locations.

In some embodiments, providing the cut depth indicator can comprise providing a plurality of markings spaced apart along the length of the boom. Determining the target location can comprise measuring a distance from an end of the boom to a cross arm of the handle assembly.

In another embodiment, a method of surgically altering a humerus using a humeral resection guide is disclosed. The humeral resection guide can include a cutting block and a boom extending away from the cutting block. The method can include orienting a side surface of the cutting block to face an exterior surface of the humerus. The method can include adjusting the boom relative to a handle using a cut depth indicator on the boom to position the cutting block at a target cut depth.

In some embodiments, the method can include further adjusting the boom relative to the handle based at least in part on a patient anatomy. The method can include cutting through the humerus at the target cut depth.

BRIEF DESCRIPTION OF THE DRAWINGS

These and other features, aspects and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters denote corresponding features consistently throughout similar embodiments. The following is a brief description of each of the drawings.

FIG. 3A-1 is a perspective view of a stemless humeral anchor and a reverse articular assembly from the system of FIG. 2 prior to inserting the reverse articular assembly and showing engagement features of these components.

FIG. 4C-1 is a top view of the stemless humeral anchor of FIG. 4C.

FIG. 4C-2 is a cross-sectional view of another embodiment of the stemless humeral anchor of FIG. 4C-1 with enhanced bone retention structures, with the cross-section taken along section 4C-2—in FIG. 4C-1.

FIG. 4D is a side view of a humeral anchor, according to another embodiment.

FIG. 4D-1 is a side view of a humeral anchor, according to another embodiment.

FIG. 4F is a schematic side view of a humeral anchor having four fins, according to another embodiment.

FIG. 4F-1 is a bottom view of the stemless humeral anchor of FIG. 4F, according to another example.

DETAILED DESCRIPTION OF THE PREFERRED EMBODIMENT

This application is directed in various examples to novel and inventive shoulder implants and tools that can be used to implant them. The shoulder implants can be part of hemi- and total shoulder joint arthroplasty systems (as improvements of the systems illustrated in FIGS. 1A and 1B, discussed below). In some cases the tools can be used with either a stemless anchor or an anchor that has a stem portion (forming an example of a stemmed humeral anchor) configured to extend into a diaphysis portion of a humerus. In some cases the tools can be used with anatomic shoulder configurations (e.g., as improvements to the tools used to arrive at the configuration of FIG. 1A) and/or reverse shoulder configurations (e.g., as improvements to the tools used to arrive at the configuration of FIG. 1B). These implants and tools can be used separately or can be combined in a system or kit that can even be provided in an operating room, allowing for intra-operative adaptation of a pre-operative plan to an enhanced surgical outcome that may only become fully apparent during the surgery, as discussed below.

I. Reverse and Anatomic Configurations for Total Shoulder Arthroplasty

Figure 1A:
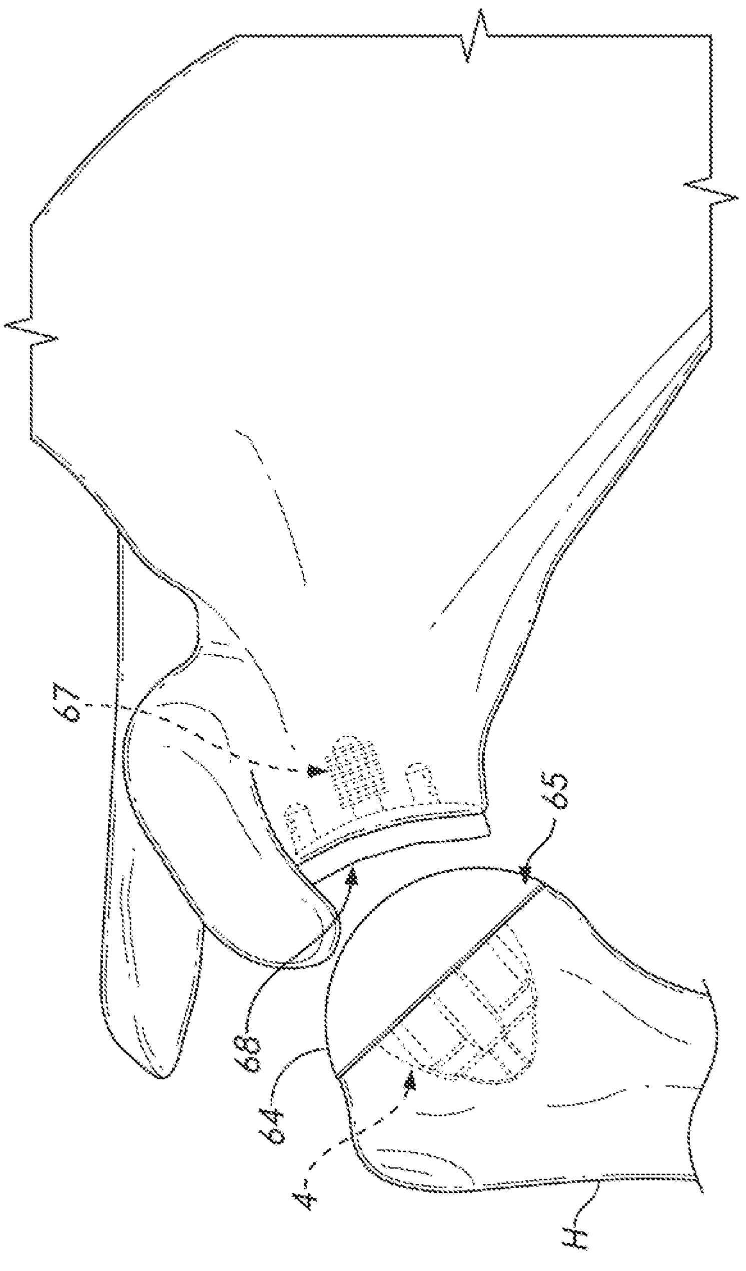
FIG. 1A shows an anatomic total shoulder arthroplasty system disposed in the humerus and the glenoid of a shoulder joint, the system including a stemless humeral anchor.
Figure 1B:
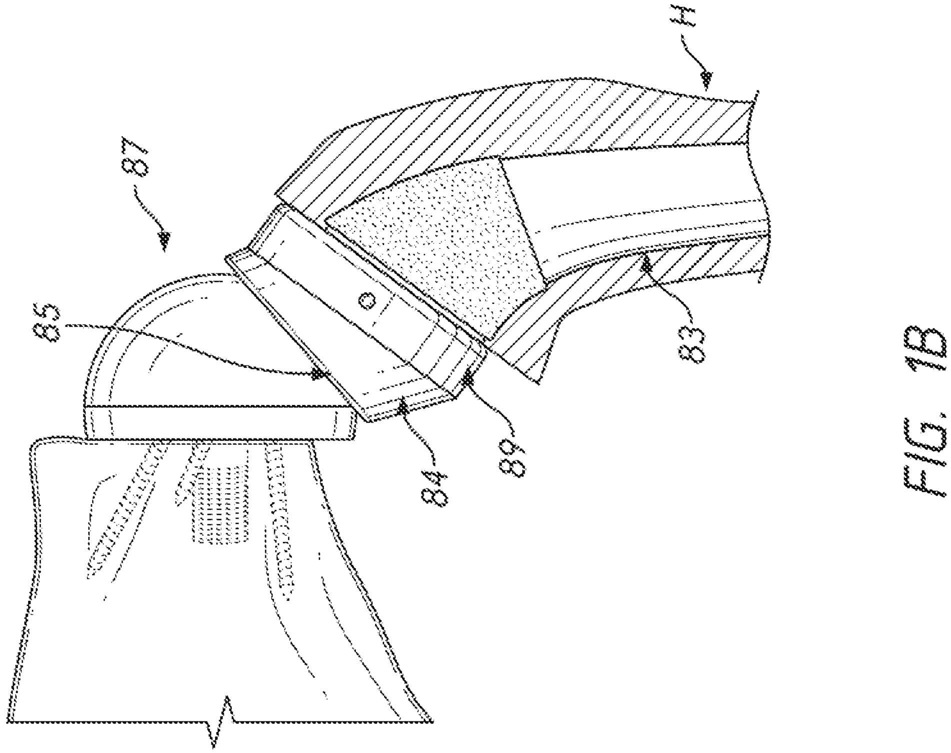
FIG. 1B shows a reverse total shoulder arthroplasty system in a shoulder joint, the system including a humeral stem anchor.

FIGS. 1A and 1B show two approaches to total shoulder arthroplasty. FIG. 1A shows an anatomic approach in which the humeral head is replaced with an articular body 64 having a convex articular surface 65. The glenoid of the scapula can be modified with an implant 67 providing a concave surface 68 for articulation of the humeral articular body 64 The humeral articular body 64 is secured to the humerus H using a stemless anchor 4 that is dedicated for and only compatible with the anatomic articular body 64.

FIG. 1B shows a reverse approach in which the humerus H is fitted with an articular body 84 having a concave articular surface 85. The glenoid region of the scapula is fitted with a spherical articular body, commonly called a glenosphere 87 (sometimes called a glenoid sphere). In this case, the concave articular surface 85 is placed on the humerus articulates of the glenosphere 87, which is fixed relative to the scapula. The reverse articular body 84 is mounted to a tray 89 that is disposed between the reverse humeral articular body 84 and a stem anchor 83 that is surgically implanted in the humerus H. The humerus H is prepared by providing access to the medullary canal of the humerus H.

One can see that the anatomic and reverse approaches generally use different hardware to secure the articular components. So, switching from an anatomic to a reverse configuration involves extraction of the stemless anchor 4. The bone stock that remains after such an extraction may or may not be suitable for supporting a stem anchor 83. Also, the presence of the tray 89 requires more of the joint space. Thus, the reverse configuration may only be suitable for some patients with large joint space or following more invasive preparation of the humerus and/or the scapula. Fortunately the implants, tools, devices, systems and kits can reduce the need for conversion and revision surgeries which can be sub-optimal for patient outcomes.

II. Systems and Kits With Shared Implant Components

Figure 2:
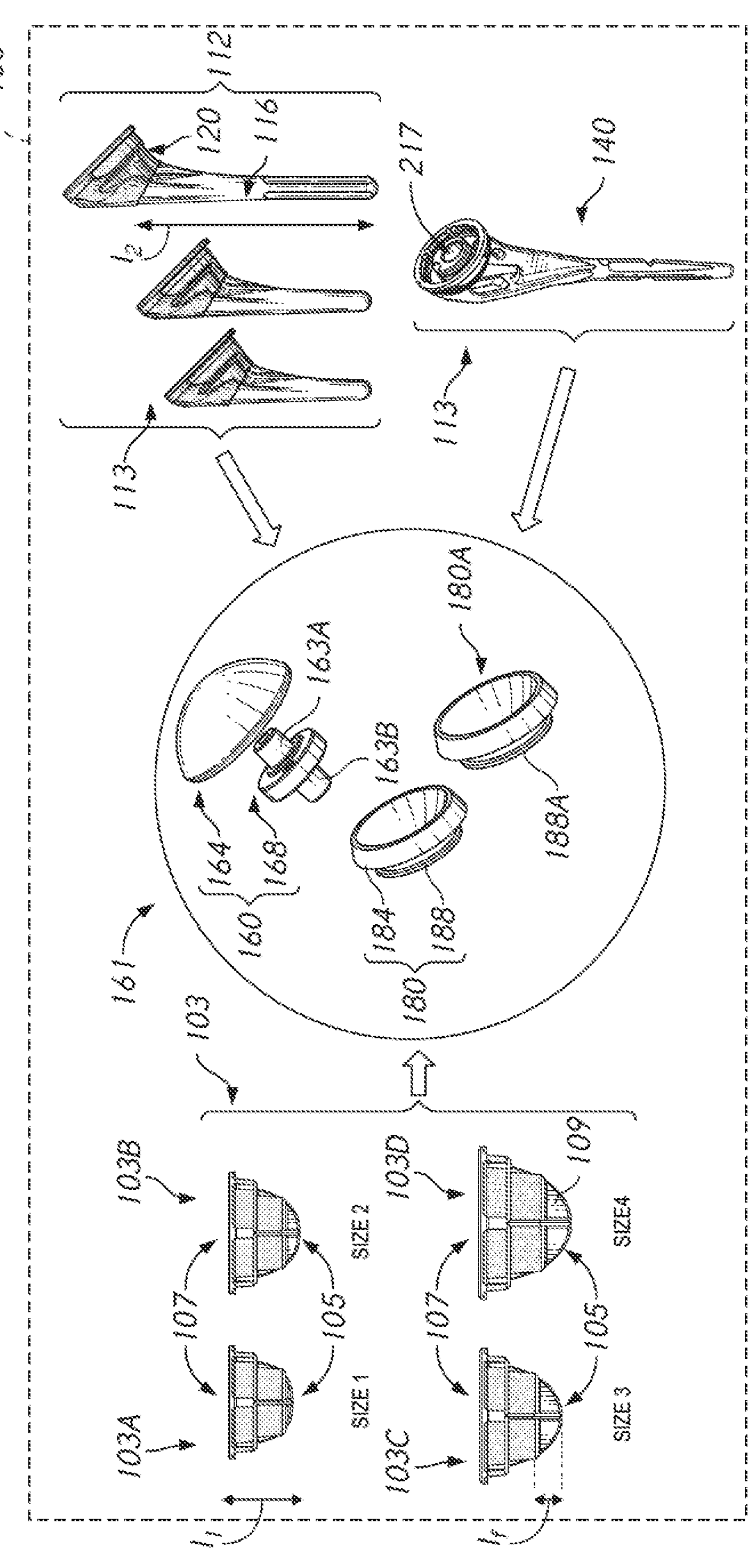
FIG. 2 is a schematic diagram of a shoulder arthroplasty system comprising an arthroplasty kit that can be used in performing anatomic or reverse arthroplasty, in converting from one of anatomic to reverse, or reverse to anatomic arthroplasty, according to various embodiments.

FIG. 2 is a schematic diagram of a total arthroplasty system comprising an arthroplasty kit 100 that can be used to perform anatomic or reverse arthroplasty, or to convert from one of anatomic to reverse or reverse to anatomic arthroplasty, according to various embodiments. The kit 100 can comprise one or a plurality of stemless humeral anchors 103, one or a plurality of stemmed humeral anchors 113, and one or a plurality of articular components 161. The stemless humeral anchors 103 can have a tapered profile in which a distal portion 105 and a proximal portion 107 of the anchor 104. The distal portion 105 of the anchors 103 shown in FIG. 2 can have one or a plurality of fins 109 extending distally. The fins 109 can be configured to secure the anchors 103 into the humerus.

As shown in FIG. 2, the stemless anchors 103 can be provided in a plurality of sizes to accommodate patients of different sizes, different degrees of bone damage to the humerus, etc. In some embodiments, the lateral size of the stemless anchors 103 may vary so as to fit within different-sized resections of the humerus. For example, the kit 100 can comprise a plurality of stemless anchors 103A, 103B, 103C, 103D . . . 103*n*, with n being the number of different sizes. Although four sizes are illustrated in FIG. 2 (e.g., n=4, with anchors 103A-103D), in other embodiments, the kit can include any suitable number of anchors. In some embodiments, a length $l_1$ of the stemless anchors 103A-103D may also vary so as to extend into the humerus by a depth that the clinician selects based on the particular patient being treated. Furthermore, and as explained below in connection with FIG. 4A, the anchors 103A-103D can have different fin lengths $l_f$ of the fins 109 to accommodate different sizes of the humerus.

In various embodiments, the fin lengths $l_f$ of the anchors 103A-103D can differ substantially so as to beneficially provide a wide range of anchor strengths to the humerus and accommodate patients with different levels of bone damage. In the arrangement of FIG. 2, for example, the first anchor 103A can have the shortest overall length $l_1$ and the shortest overall fin length $l_f$. The fourth anchor 103D can have the longest overall length $l_1$ and the longest overall fin length $l_f$. In various embodiments, a ratio of an overall length $l_1$ of one anchor 103 (for example, the largest anchor 103) to an overall length $l_1$ of another anchor 103 (for example, the smallest anchor 103) in the kit 100 can be in a range of 1.15 to 2.5, in a range of 1.18 to 2.5, in a range of 1.2 to 2.5, in a range of 1.2 to 2, in a range of 1.2 to 1.8, in a range of 1.2 to 1.6, in a range of 1.3 to 1.6, or in a range of 1.25 to 1.4.

The kit 100 can also include one or a plurality of stemmed humeral anchors 113. The kit 100 can include one or more humeral stem anchors 112, each of which includes a proximal metaphysis portion 120 and an elongate diaphysis portion 116 extending therefrom. The diaphysis portion 116 is sometimes referred to herein as a stem or stem portion. In some embodiments, the kit 100 can also include a trauma or fracture stem anchor 140, which can be used in patients that have experienced a fracture of the humerus H. The stemmed humeral anchors 113 may be used in patients in which stemless anchors 103 may not be adequately secured to the humerus, for example, in patients that have experienced severe bone loss. The trauma or fracture stem may be used where the humerus has fractured into one or more pieces. As with the stemless anchors 103, the kit 100 can include stemmed anchors 113 having a plurality of different sizes, e.g., different lateral sizes and/or different lengths $l_2$. For example, as shown in FIG. 2, the stemmed humeral anchors 113 can have respective lengths $l_2$ that are longer than the lengths $l_1$ of the stemless anchors 103. Beneficially, the inclusion of differently-sized stemmed anchors 113 in the kit 100 can enable the clinician to select the appropriate size for a particular patient to ensure a secure implant of the anchor 113 into the patient, in view of the patient's bone size and health. In various embodiments, the lengths $l_2$ of the stemmed humeral anchors can be in a range of 55 mm to 175 mm. By contrast, the shorter lengths $l_1$ of the stemless humeral anchors 103 can be in a range of 16 mm to 28 mm. In various embodiments, stemmed humeral anchors 113, 140 can be configured to reach into the intramedullary canal of the humerus H for additional anchorage.

Beneficially, the kit 100 can comprise one or a plurality of shared humeral components that be used with either the stemless humeral implants 103 or the stemmed humeral implants 113, depending on which implant 103 or 113 would be more appropriate for a particular patient's humeral anatomy. For example, the shared humeral components of the kit 100 can comprise a plurality of articular components or assemblies 161 that can be used in conjunction with either the stemless implants 103 or the stemmed implants 113. As explained herein, both the stemless humeral anchors 103 and the stemmed humeral anchors 113 can include shared engagement features that can be used with the same set of tools and/or articular components. For example, as described herein, the stemless anchors 103 and stemmed anchors 113 can include convex and concave locking features configured to engage with the same set of articular components.

For example, the kit 100 can include an anatomic articular component 160 configured to mechanically couple to both the stemless humeral implants 103 and the stemmed humeral implants 113. The clinician may select the anatomic articular component 160 for procedures in which an anatomic reconstruction is suitable. The anatomic articular component 160 can comprise a coupler 168 and an articular body 164 (anatomical) configured to mechanically engage the coupler 168. As shown in FIG. 2, the articular body 164 for the anatomic articular component 160 can comprise a rounded, convex surface configured to engage a glenoid surface of the patient. The coupler 168 can serve to mechanically connect the anatomical articular body 164 (e.g., a rounded or essentially spherical surface) to either a stemless humeral implant 103 or a stemmed humeral implant 113, depending on the patient's humeral bone structure. The articular body 164 and the coupler 168 can comprise a metal, such as cobalt, chrome, or titanium. In some embodiments, the articular body comprises a pyrocarbon layer on at least the articular surface. In various embodiments, the kit 100 can include anatomic articular components 160 having a plurality of sizes.

The kit 100 can also include a reverse articular component 180 configured to mechanically couple to both the stemless humeral implants 103 and the stemmed humeral implants 113. The clinician may select the reverse articular component 180 for procedures in which a reverse anatomic reconstruction is suitable. The reverse articular component 180 can comprise a reverse articular body 184 and a locking device 188 configured to secure the reverse articular component 180 to a stemless humeral implant 103 or a stemmed humeral implant 113, depending on the clinician's recommendation during the procedure. As shown, the reverse articular body 184 can comprise a rounded concave surface (e.g., essentially spherical) configured to engage with a glenosphere connected to the glenoid of the patient (not shown but in some cases combined with the kit into a larger surgical kit). In addition, in some embodiments, the kit 100 can include a wear resistant reverse articular component 180A, which may be generally similar to the reverse articular component 180 but may further be formed to include vitamin E to promote long-term compatibility with the patient's bone structure. The reverse components 180, 180A can comprise a polymer, including, for example, ultra high molecular weight polyethylene. In various embodiments, the kit 100 can include reverse articular components 180, 180A having a plurality of sizes.

During an arthroplasty procedure, the clinician may inspect the bone structure of the humerus and/or the scapula to determine whether the anatomy is suitable for a stemless or stemmed humeral anchor, and whether the anatomy is suitable for an anatomical or reverse anatomical reconstruction. Beneficially, the kit 100 shown in FIG. 2 can provide the clinician with a total arthroplasty system including components that are compatible with stemless or stemmed anchors, and with anatomical or reverse anatomical constructions. For example, during a procedure, the clinician may observe that the patient has sufficient humeral bone structure so that a stemless anchor 103 may be used to reduce the damage to the patient's anatomy. The clinician may also elect whether to proceed with an anatomical reconstruction or a reverse construction, and can accordingly select either the anatomical articular component 160 or the reverse articular component 180, 180A.

Similarly, if during a shoulder arthroplasty procedure, the clinician determines that the patient's bone structure is damaged or otherwise more suited to a stemmed anchor 113, then the clinician can select an appropriately sized stemmed anchor 113. The clinician can further select whether to proceed with an anatomical reconstruction or a reverse construction, and can accordingly select either the anatomical articular component 160 or the reverse articular component 180, 180A. Beneficially, the kit 100 of FIG. 2 includes interchangeable or interoperable components that can be used in stemmed or stemless anchors, and with anatomical or reverse anatomical reconstructions. Because the shared humeral articular components 161 (e.g., anatomical or reverse anatomical articular bodies) can be used with either the stemless or stemmed anchors 103, 113, the clinician can make, or change, reconstruction decisions during surgery. The kit 100 can accordingly enable the clinician to quickly determine the reconstruction procedure most suitable for a patient and can provide the clinician with the components to be used for that reconstruction procedure.

As explained above, for humeral fractures, the kit 100 can also include one or more trauma stems 140. Beneficially, the trauma stem(s) 140 can include engagement features generally similar to or the same as the engagement features in the stemless anchors 103 and humeral stem anchors 112, such that the stemless anchors 103, the humeral stem anchors 112, and the trauma stem(s) 140 can be used with a common set of shared articular components 161 and tools. Beneficially, therefore, the kit 100 can provide a shared set of implantation tools and a shared set of articular components 161 that can be used with either stemless or stemmed humeral anchors 103, 113, and that can be used for anatomical or reverse anatomical reconstructions.

In some embodiments, the coupler 168 can comprise a proximal extension 163A configured to connect to the articular body 164 and a distal extension 163B. The distal extension 163B for the fracture stem 140 can be received within a recess 217 of the fracture stem 140 for anatomical reconstructions. The disc or middle portion 162 disposed between the proximal extension 163A and the distal extension 163B can be eliminated since the recess 217 is elevated toward the resection plane. In a modified embodiment, the recess 217 is recessed from (e.g., extends distally from) a distal end of a second recess. In those embodiments, the disc or middle portion 162 provides a spacer function in use in the trauma stem 140. Additional details of trauma stems may be found throughout International Application No. PCT/US2015/065126, filed Dec. 15, 2015, the entire contents of which are hereby incorporated by reference herein in their entirety and for all purposes.

III. Examples of Humeral Anchors

As noted above, this application discloses some kits and systems that provide shared components and that may include multiple types of humeral anchors. The humeral anchors can include stemless anchors, anchors with stem portions (examples of stemmed humeral anchors), and fracture anchors that can have stems.

A. Stemless Humeral Anchor Examples

Some stemless humeral anchor examples disclosed herein includes features for enhanced metaphyseal retention and/or features for enhanced articular component connection or retention. These features can increase the percentage of patients in a patient population that can benefit from a stemless approach, which is generally less invasive than a stemmed approach.

Figure 3A:
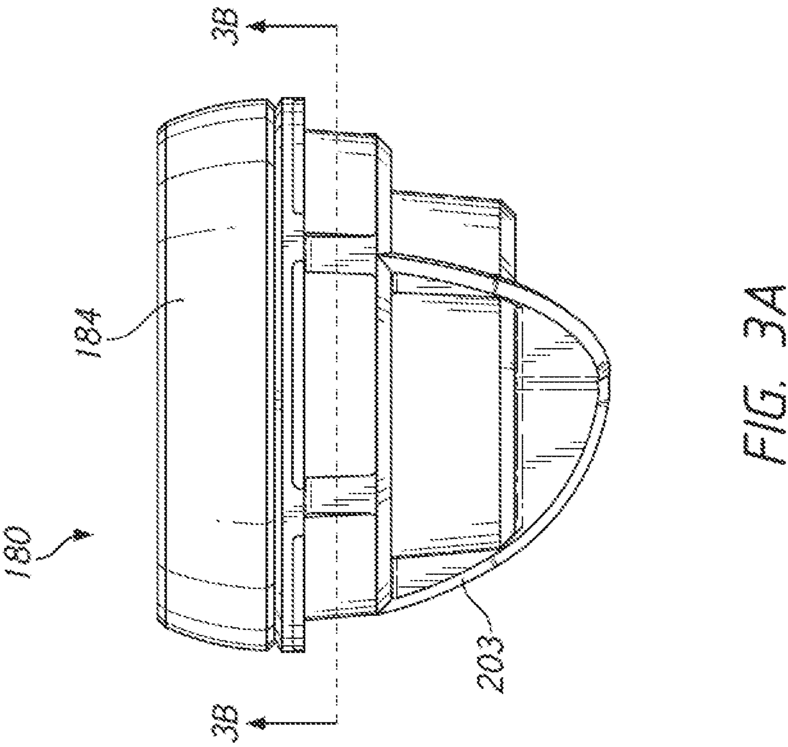
FIG. 3A is a side view showing a reverse articular body connected to a humeral stemless anchor, according to various embodiments.
Figure 3:
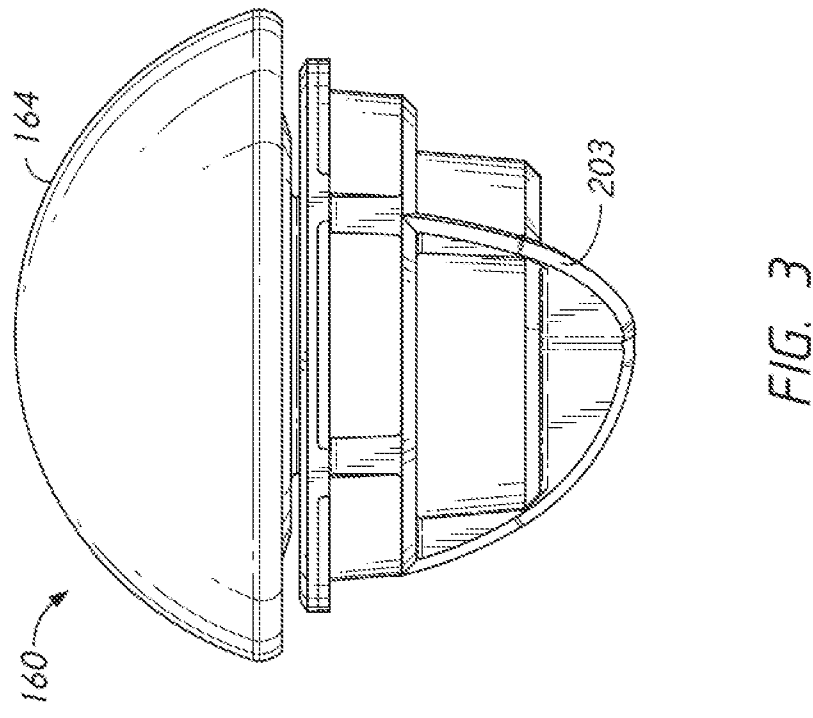
FIG. 3 is a side view showing an anatomical articular body connected to a humeral stemless anchor, according to various embodiments.
Figures 1, 3A:
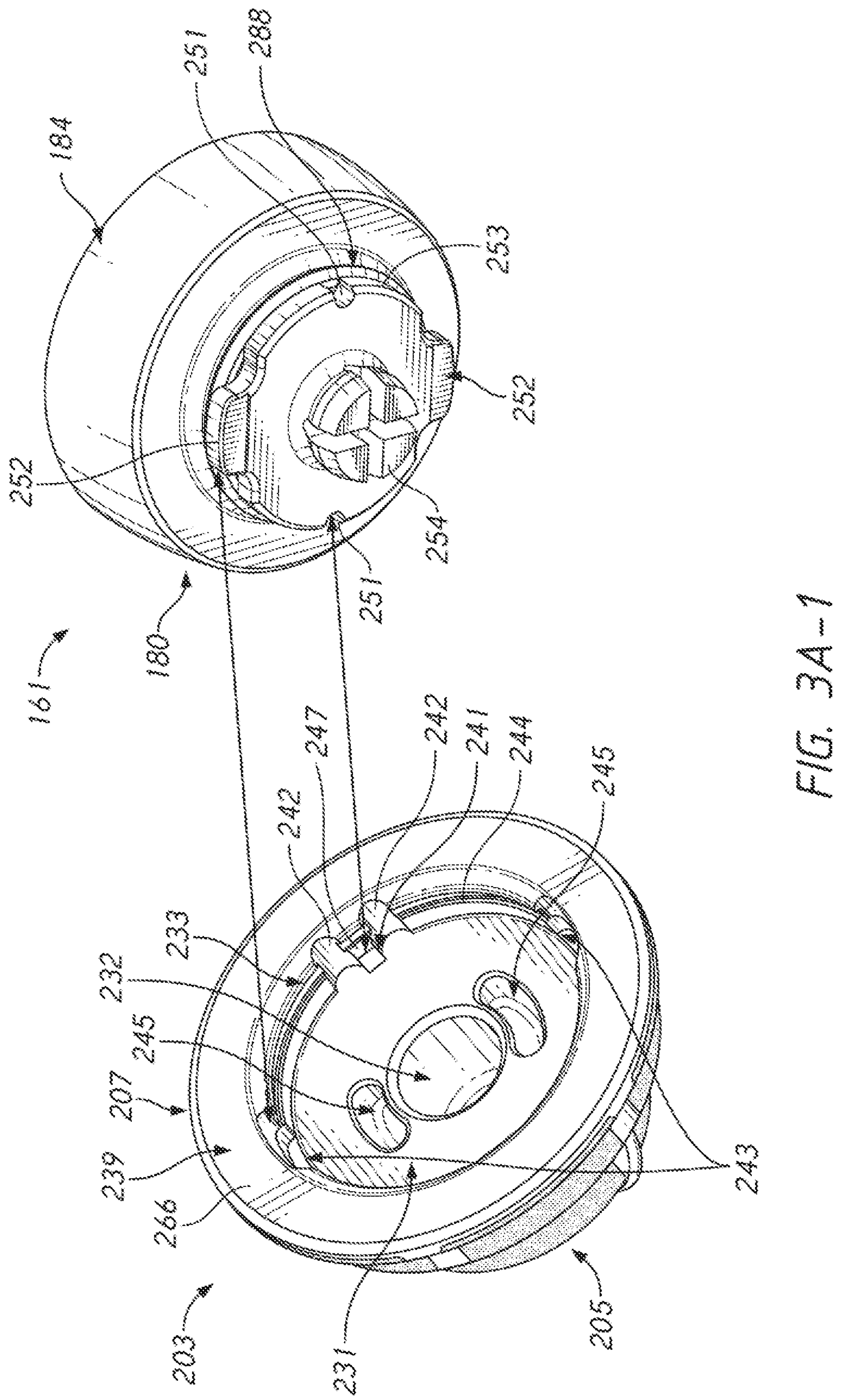
Figure 3B:
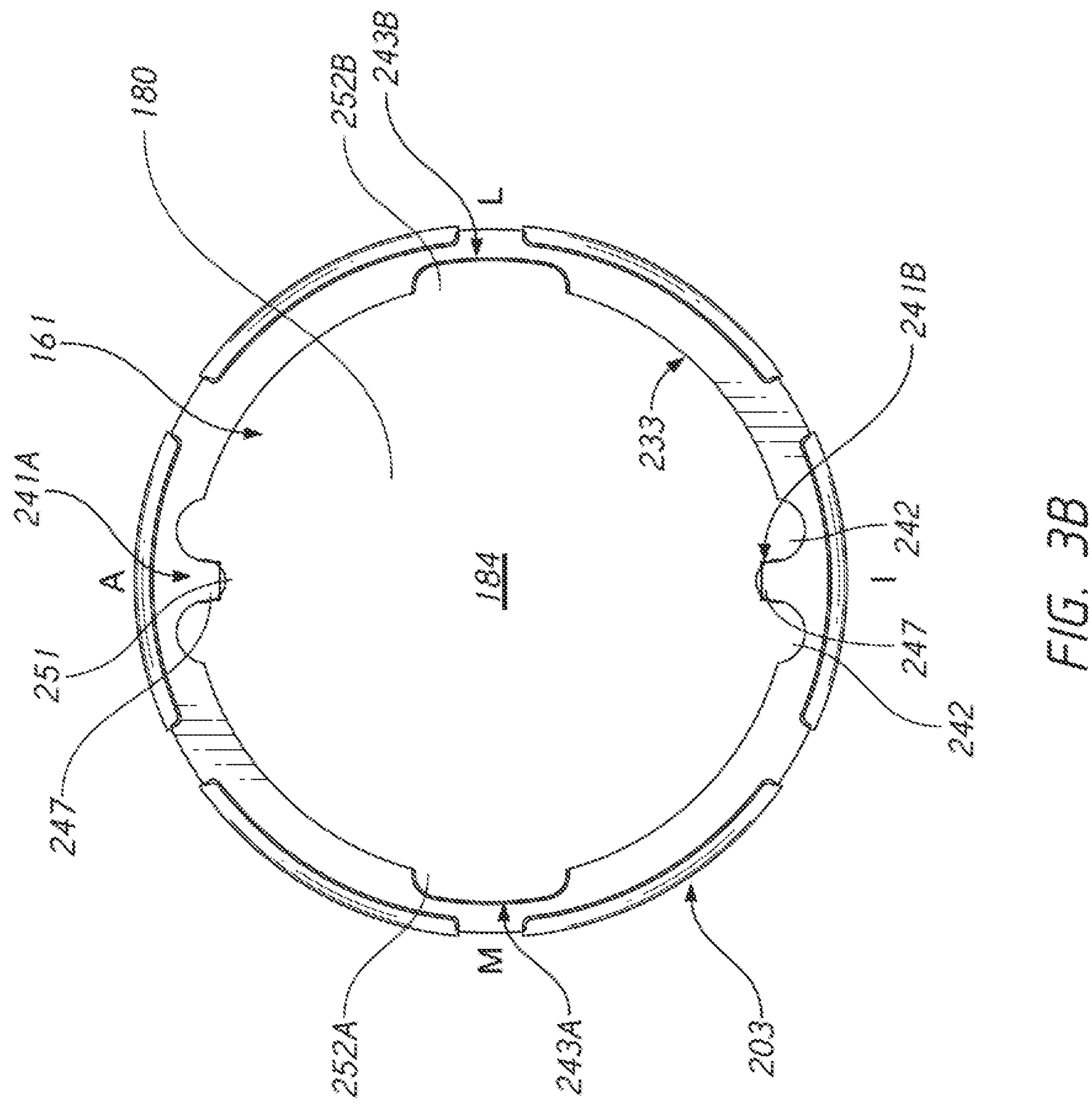
FIG. 3B is a cross-sectional view of the stemless humeral anchor and the reverse articular assembly of FIG. 3A after the reverse articular assembly has been inserted, the section being taken transverse to the direction of insertion of the reverse articular assembly.
Figure 3C:
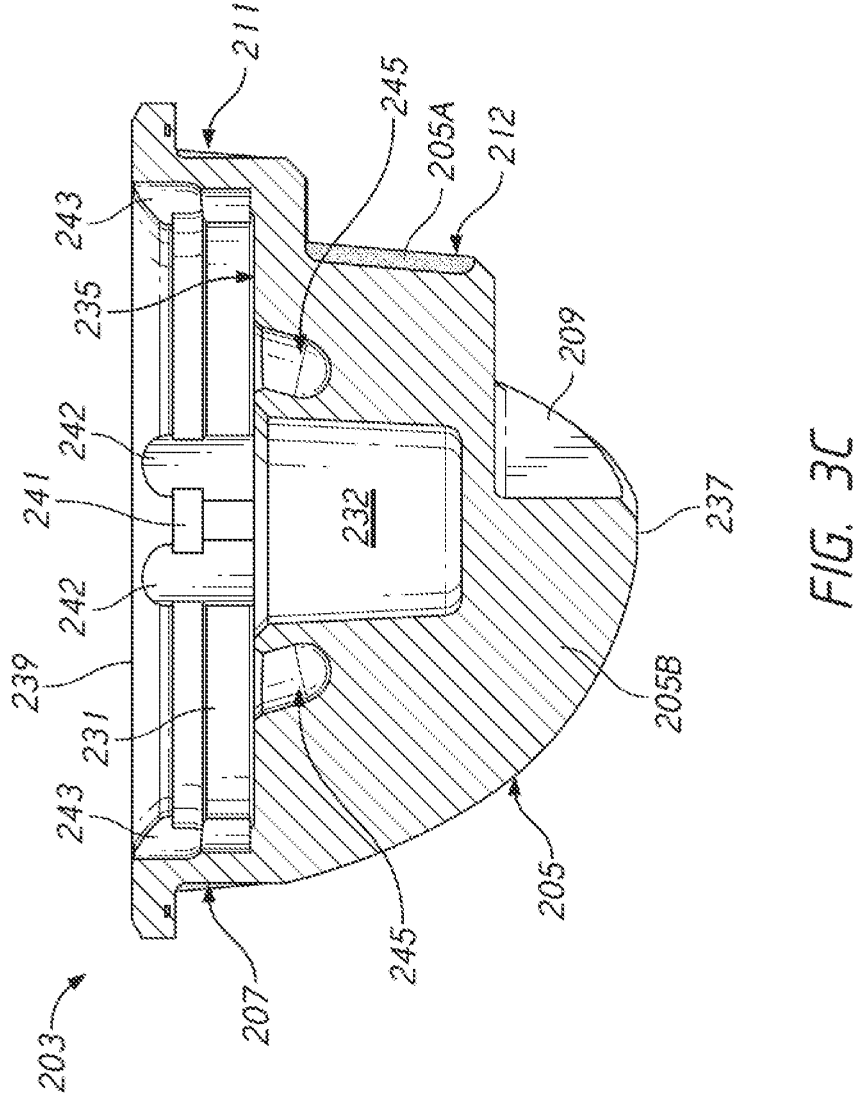
FIG. 3C is a cross-sectional view of the stemless humeral anchor of FIG. 3A, the section being taken along the direction of insertion of the reverse articular assembly.

FIGS. 3-3C illustrate an example of a stemless humeral anchor 203. Unless otherwise noted, the components of FIGS. 3-3C may be the same as or generally similar to like-numbered components of FIG. 2, with the reference numerals incremented by 100. In FIGS. 3-3A-1, the stemless humeral anchor 203 is shown as being connected to (or prior to being connected to) an articular component 161, which can comprise the anatomical articular component 160 or the reverse articular component 180. In FIG. 3, the stemless humeral anchor 203 is shown connected to the anatomical articular body 164 of the anatomical articular component 160. In FIG. 3A, the stemless humeral anchor 203 is shown connected to the reverse articular body 184 of the reverse articular component 180. The articular component 161 can be an articular assembly, e.g., a polymeric articular body and a locking component such as a locking ring.

As shown in FIGS. 3A-1-3C, a first recess 231 can extend distally from a proximal end 239 of the humeral anchor 203 and into the proximal portion 207. The first recess 231 can be sized and shaped to receive a distal or lateral portion of the articular component 161, including the reverse articular body 184 and a locking device 288. As shown in FIG. 3C, the first recess 231 can be disposed in the proximal portion 207 of the anchor 203. The proximal portion 207 can be defined at least in part by a first proximal exterior surface 211. A second recess 232 can extend distally from the first recess 231 into a first section 205A of the distal portion 205 of the anchor 203. The second recess 232 can be sized and shaped to receive the distal extension 163B of the coupler 168 for connecting the anatomic articular component 160 to the stemless humeral anchor 203. The first and second recesses 231, 232 can have different volumes. For example, the volume of the first recess 231 (and/or a diameter or major lateral dimension of the first recess 231) can be larger than the volume of the second recess 232 (and/or a diameter or major lateral dimension of the second recess 232). Thus, the combined space formed by the recesses 231, 232 can be larger toward the proximal end 239 of the anchor 203 and smaller toward a distal end 37 of the anchor 203, as shown, e.g., in FIG. 3C.

The first section 205A of the distal portion 205 can be defined at least in part by a second distal exterior surface 212, and can be dimensioned to occupy a portion of a metaphysis of the humerus when implanted. A second section 205B of the distal portion 205 can comprise the one or more fins 209 configured to extend farther into the metaphysis than the first section 205A to secure the anchor 203 to the humerus. As shown in FIG. 3C, the second recess 232 can be tapered inwardly to engage the coupler 168, e.g., a tapered surface portion of the distal extension 163B thereof. One or a plurality of blind holes 245 can also extend distally from a distal interior surface 235 of the proximal portion 207 bounding the distal end of the first recess 231 into the second section 205B of the distal portion 205. The blind holes 245 can engage a tool that enables insertion of the humeral anchor 203 into the humerus. An example of a tool that can engage the blind holes 245 is discussed below in Section IV(A) and Section IV(B). As shown in FIGS. 3A-1 and 3C, the blind holes 245 can extend distally at angled inwardly towards the interior second recess 232.

The anchor 203 can include an inner periphery 233 disposed about the first recess 231 adjacent to the proximal end 239 of the humeral anchor 203. The inner periphery 233 can be a surface portion extending from the distal interior surface 235 to the proximal end 239 of the humeral anchor 203. The inner periphery 233 can include one or a plurality of concave locking features 243 disposed in the inner periphery 233 and one or a plurality of convex locking features 241 disposed in the inner periphery 233. As shown in FIGS. 3A-1-3C, in one example where both are provided, the concave locking feature 243 can be circumferentially spaced apart from the convex locking feature 241. Further, in the embodiment of FIGS. 3A-3C, the anchor 203 includes a plurality, e.g., two or a pair, of concave locking features 243A, 243B spaced apart from one another along the inner periphery 233. The locking features 243A, 243B can be disposed opposite one another across the recess 231 on the inner periphery 233. In some embodiments, as shown in FIG. 3B, a first concave locking feature 243A can be disposed at a medial portion M of the humeral anchor 203, and a second concave locking feature 243B be disposed at a lateral portion L of the humeral anchor 203. In some examples, a first concave locking feature 243A can be disposed at an anterior portion of the humeral anchor 203 and a second concave locking feature 243B be disposed at a posterior portion of the humeral anchor 203. The first concave locking feature 243A and the second concave locking feature 243B be disposed opposite one another on the inner periphery 233. An angle can be defined between the first and second locking features 243A, 243B, e.g., 180 degrees, 120 degrees, 90 degrees, 60 degrees or other angular separation therebetween. More than two locking features 243A or 243B can be provided, e.g., three at 120 degree spacing, four at 90 degree spacing, six at 60 degree spacing. The spacing between the locking features 243A, 243B can be unequal in some embodiments.

The concave locking features 243 can comprise a curved surface extending radially outward relative to the inner periphery 233. The concave locking features 243A, 243B can be sized relative to locking features of the articular component 161 that provides an interference connection between the articular component 161 and the locking features 243A, 243B. Such interference fit can include an aspect of the concave locking features 243A, 243B being smaller than a corresponding exterior surface of the articular component 161.

A plurality, e.g., two or a pair, of convex locking features 241A, 241B can also be disposed opposite one another along the inner periphery 233. In some embodiments, as shown in FIG. 3B, a first convex locking feature 241A can be disposed at an anterior portion A of the humeral anchor 203, and a second opposing convex locking feature 241B be disposed at a posterior portion P of the humeral anchor 203. The convex locking feature 241 can comprise a projection 247 extending radially inward relative to the inner periphery 233 towards the first recess 231. The projection 247 can be elongate with a longitudinal direction oriented proximal-distal in the first recess 231, e.g., parallel to a direction of insertion of the articular component 261. The projection 247 can extend toward a central portion of the first recess 231 from an adjacent portion of the periphery 233. Portions of the periphery 231 adjacent to the projection 247 can be concave in structure facing toward the first recess 231 relative to the projection 247. For example, the convex locking feature 241 can be adjacent to a pair of concave recesses 242 formed in the inner periphery 233. As with the concave locking features 243A, 243B, the convex locking features 241A, 241B can be sized relative to corresponding locking features of the articular component 161 that provides an interference connection between the articular component 161 and the convex locking features 241A, 241B. Such an interference fit can include an aspect of the convex locking features 241A, 241B being smaller than a corresponding exterior surface of the articular component 161, for example, the projection 247 can extend into and engage a corresponding locking feature of the articular component 161.

A circumferential groove 244 can extend circumferentially along the inner periphery 233. The groove 244 can comprise a plurality of segments disposed circumferentially between concave locking feature 243A and convex locking feature 241A, between concave locking feature 243A and convex locking feature 241B, between concave locking feature 243B and convex locking feature 241A, and between concave locking feature 243A and convex locking feature 241B. The groove 244 can comprise any suitable number of segments, for example, four, six, etc. As explained below, the groove 244 can be sized relative to the locking feature 288 of the articular component 161 to provide a snap or interference fit with the locking feature 288. In various embodiments, the groove 244 can comprise a distally-facing surface that can secure the locking feature 288 of the articular component 161 to the anchor 203.

The clinician can insert the articular component 161 (e.g., the reverse articular component 180 shown in FIG. 3A-1) into the first recess 231 of the stemless humeral anchor 203 to secure the articular component 161 to the anchor 203. The locking feature 288 of the articular component 161 can comprise convex tabs 252 spaced apart from one another, for example, on opposite sides of the articular component 161. The locking feature 288 can also comprise concave slots 251 spaced apart from one another. A locking ring 253 can be disposed circumferentially within a groove of the articular component 161. A distal projection 254 can extend distally from the locking feature 288 to engage the stemless humeral anchor 203 in the second recess 232.

When the clinician inserts the articular component 161 into the first recess 231, the clinician can align the articular component 161 relative to the first recess 231 such that the convex tabs 252 engage with the corresponding concave locking features 243 of the anchor 203 and such that the concave slots 251 engage with the corresponding convex locking features 241 of the anchor 203. The tabs 252, slots 251, concave locking features 243, and convex locking features 241 can be dimensioned such that, upon insertion of the articular component 161 into the first recess 231, an interference or friction fit is formed between the reverse articular component 180 and the humeral anchor 203. The concave locking features 243 and convex locking feature 241 can serve as anti-rotation features to inhibit relative rotation between the anchor 203 and the articular component 161. The locking ring 253 can extend into the circumferential groove 244 of the anchor 203. The locking ring 253 can serve to lock the articular component 180 into the anchor 203 and to prevent the articular component 161 from translating vertically outward from the anchor 203.

FIG. 3B shows the connection of the articular component 161 (such as a reverse articular component 180) to the anchor 203. The outer periphery of the articular component 161 can be seen inside the inner periphery 233 of the anchor 203. As explained above, the tabs 252 can engage the concave locking features 243A, 243B of the anchor 203 in an interference fit. Similarly, the concave slots 251 of the articular component 161 can engage the projections 247 of the convex locking features 241A, 241B in an interference fit. Although not illustrated in the view of FIG. 3B, the locking ring 253 can fit within the groove 244 of the inner periphery 233.

In embodiments where one or a plurality of locking features have different configurations, the rotational position can be more easily confirmed intra-operatively. For example, the tabs 252 can be visually confirmed to be rotationally positioned correctly relative to the concave locking features 243A, 243B. By providing two opposite tabs 252, only two rotational positions can result in securing the articular component 161 to the anchor 203. In some cases, these two positions provide identical biomechanics of the shoulder joint when assembled. The two positions are rotationally symmetric. In other embodiments the two positions provide two options for biomechanics such that the surgeon can select among two positions of the articular component 180 relative to the anchor 203. In a first rotation position, a tab 252A is positioned in a superiorly positioned concave recess 243A and a tab 252B is positioned in an inferiorly positioned concave recess 243B. In a second rotational position, the tab 252A is positioned in the inferiorly positioned concave recess 243B and the tab 252B is positioned in the superiorly positioned concave recess 243B.

In various embodiments, the proximal end 239 of the humeral anchor 203 can comprise a collar or rim 266 configured to be positioned against the humerus. As explained below in connection with the stemmed humeral anchor 1200 of FIG. 6C, the rim 266 can comprise a cancellous bone compression member, which can include a bone compression surface. The bone compression surface of the stemless anchor 203 can be generally similar to the bone compression member shown in FIG. 6C. For example, the bone compression surface can be disposed adjacent to or at the proximal end 239 of the humeral anchor 203 and can be disposed about a medial side of the proximal portion 203. As with FIG. 6C, the bone compression surface can be disposed about only the medial side, e.g., about a portion of the periphery of the proximal end 239 not including the lateral side of the humeral stem. The bone compression member of the stemless anchor 203 may include features generally similar to those described below in connection with FIG. 6C.

For example, as with the stemmed anchor 1200 of FIG. 6, the cancellous bone compression member of the stemless anchor 203 can be made for a patient in a patient specific manner. For example, in various embodiments, the shoulder of the patient (e.g., the humerus and/or glenoid) can be imaged during pre-operative imaging procedures. The cancellous bone compression member of the stemless anchor 203 can be shaped to specifically match the patient's anatomy based on the imaging performed before surgery. For example, in various embodiments, the cancellous bone compression member can be manufactured using various types of additive manufacturing techniques such as three-dimensional (3D) printing. The image data representative of the patient's cancellous bone structure can be transmitted to 3D printing machinery which can manufacture the cancellous bone compression member to substantially match or conform to the patient's cancellous bone tissue. The member can be shaped to extend at least to an inner wall portion of a cortical bone layer. The member can be shaped to extend beyond an inner wall portion of a cortical bone layer. The member can be shaped to follow the shape of the periphery of the humerus at the resection surface. These configurations can be made patient specific to reduce, minimize or eliminate stress shielding and concomitant bone loss. Accordingly, various embodiments disclosed herein can beneficially provide patient-specific structures to improve the fit of the anchor within the humerus.

Figures 4A, 4B:
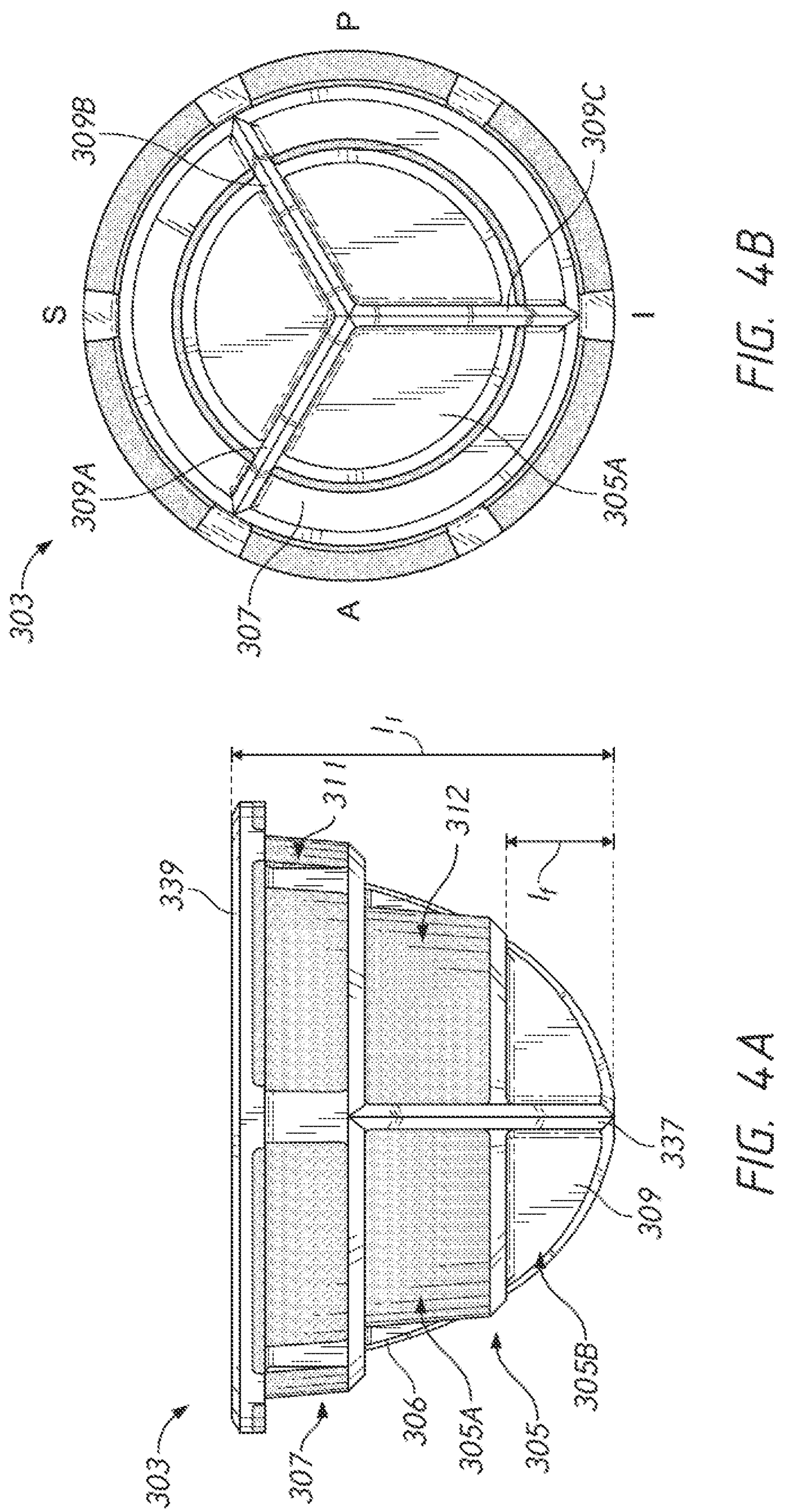
FIG. 4A is a side view of a stemless humeral anchor, according to various embodiments.
FIG. 4B is a bottom view of the stemless humeral anchor of FIG. 4A, according to an example.

FIGS. 4A-4G illustrate various features of the exterior surface of humeral anchors. For example, FIG. 4A is a schematic side view of a stemless humeral anchor 303. The humeral anchor 303 can be the same as or different from the humeral anchors 103, 203 of FIGS. 2-3C. Unless otherwise noted, the components of FIG. 4A may be the same as or generally similar to like-numbered components of FIGS. 3-3C, with the reference numerals incremented by 100 relative to the reference numerals of FIGS. 3-3C. As shown in FIG. 4A, the proximal portion 307 of the stemless humeral anchor 303 can include a first proximal exterior surface 311. A first section 305A of the distal portion 305 of the stemless humeral anchor 303 can include the second distal exterior surface 312. The first proximal exterior surface 311 can be wider than the second distal exterior surface 312. For example, the first proximal exterior surface 311 can be disposed about the first recess 331. The second distal exterior surface 312 can be disposed about the second recess (for example, the second recess 232 shown in FIG. 3C). In various embodiments, a ratio of a first width of the proximal portion 307 (for example, as measured at opposing locations of the first proximal exterior surface 311) to a second width of the first distal section 305A (for example, as measured at opposing locations of the second distal exterior surface 312) can be in a range of 1.2 to 2, in a range of 1.2 to 1.8, in a range of 1.25 to 1.8, in a range of 1.3 to 1.75, in a range of 1.3 to 1.7, or in a range of 1.3 to 1.6. Such ratios of first to second widths can beneficially serve a bone-filling function to secure the anchor 302 to the humerus.

In the illustrated embodiment, as explained above, both the first and second surfaces 311, 312 can serve a bone filling function, e.g., the respective widths of the first and second surfaces 311, 312 can be sufficiently large so as to fill and secure the anchor 302 to the humerus. In some embodiments, the first proximal exterior surface 311 can be tapered inwardly. In other embodiments, the first exterior surface 311 can comprise a straight or generally cylindrical surface. The first exterior surface 311 can form a right cylinder relative to the proximal end 339 of the humeral anchor 303. In other words the first exterior surface 311 extends perpendicular to a plane that includes the proximal end 339 of the anchor 303. In other embodiments, the first exterior surface 311 can be tapered inwardly. The surface 311 can be oriented at an angle of 5 degrees from perpendicular from the plane that includes the proximal end 339 of the anchor 303. The surface 311 can be oriented at an angle between 1 degree and 10 degrees from perpendicular from the plane that includes the proximal end 339 of the anchor 303. In various embodiments, the second distal surface 312 can comprise a straight or generally cylindrical surface. For example, the surface 312 can also be oriented perpendicular to a plane that includes the proximal end 339 of the anchor 303. In other embodiments, the second exterior surface 312 can be tapered inwardly. For example, the second surface 312 can be oriented at an angle of 5 degrees from perpendicular from the plane that includes the proximal end 339 of the anchor 303. The surface 312 can be oriented at an angle between 1 degree and 10 degrees from perpendicular from the plane that includes the proximal end 339 of the anchor 303.

As explained above in connection with FIGS. 3-3C, the fins 309 of the second distal section 305B can extend distally from the first distal section 305A to a distal end of the humeral anchor 303. The fin length $l_f$ can be sufficiently long so as to reduce, minimize or eliminate rotation of the anchor 303 within the metaphysis upon application of a load, e.g., a torque, to an articular component coupled with the anchor. In various embodiments, for example, the fin length $l_f$ can be at least 10% of the overall first length $l_1$ of the humeral anchor 303, at least 11% of the overall first length $l_1$ of the humeral anchor 303, at least 20% of the overall first length $l_1$ of the humeral anchor 303, at least 24% of the overall first length $l_1$ of the humeral anchor 303, at least 28% of the overall first length $l_1$ of the humeral anchor 303, at least 29% of the overall first length $l_1$ of the humeral anchor 303, at least 30% of the overall first length $l_1$ of the humeral anchor 303, at least 31% of the overall first length $l_1$ of the humeral anchor 303, at least 33% of the overall first length $l_1$ of the humeral anchor 303, or at least 34% of the overall first length $l_1$ of the humeral anchor 303. In various embodiments, the fin length $l_f$ can be in a range of 8% to 40% of the overall first length $l_1$ of the humeral anchor 303, in a range of 10% to 40% of the overall first length $l_1$ of the humeral anchor 303, in a range of 11% to 40% of the overall first length $l_1$ of the humeral anchor 303, in a range of 24% to 40% of the overall first length $l_1$ of the humeral anchor 303, in a range of 30% to 40% of the overall first length $l_1$ of the humeral anchor 303, in a range of 8% to 35% of the overall first length $l_1$ of the humeral anchor 303, or in a range of 30% to 35% of the overall first length $l_1$ of the humeral anchor 303. Moreover, one or a plurality of radial projections 306 can extend radially outward from the humeral anchor 303. As shown, for example, the radial projections 306 can extend outwardly from the second distal surface 312. The radial projections 306 can enhance the connection of the humeral anchor 303 to the humerus. The radial projections 306 can be tapered inwardly and distally as shown.

FIG. 4B is a bottom view of the stemless humeral anchor 303 of FIG. 4A. In the embodiment of FIG. 4B, the anchor 303 can comprise three (3) fins 309A, 309B, and 309C. As shown in FIG. 4B, fin 309C can be oriented along an inferior direction I. Fin 309A can be oriented diagonally so as to have respective directional components along an anterior direction A and a superior direction S. Fin 309B can be oriented diagonally so as to have respective directional components along a posterior direction P and the superior direction S. As shown the fins 309A-309C can be evenly spaced apart, for example, by about 120°. The directions inferior I, superior S, anterior A, and posterior P each corresponding to a direction of a humerus of a patient when any of the anchors 303, 403, 503, are applied. During implantation, the clinician can orient the humeral anchor 303 in this manner and can insert the anchor 303 into the humerus with the illustrated orientation. This orientation may beneficially improve the anchoring of the implant to the humerus because the orientation of the anterior-superior and posterior-superior fins have more surface area facing a direction more likely to be subject to a tilt out force.

Figures 1, 4C:
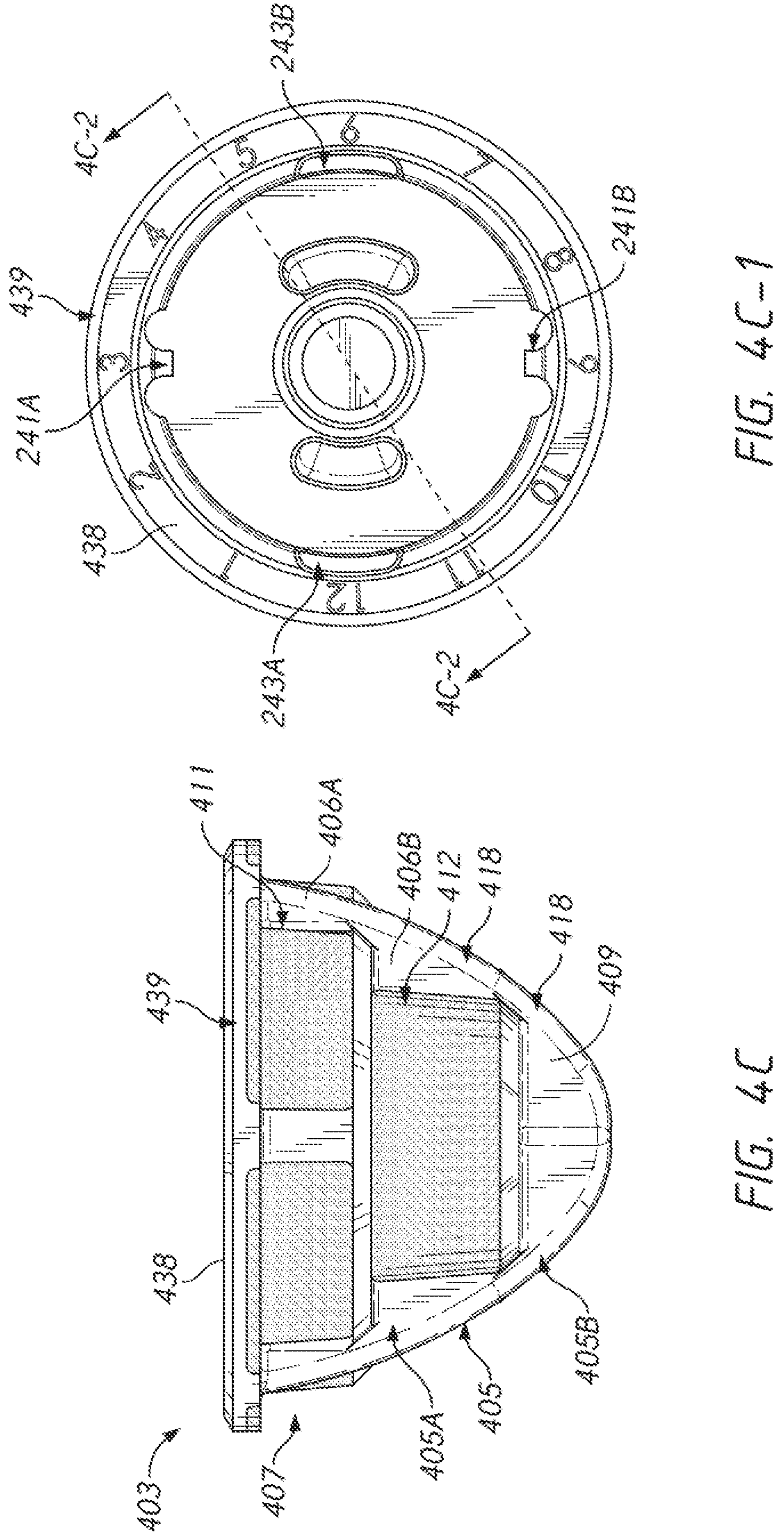
Figures 2, 4C:
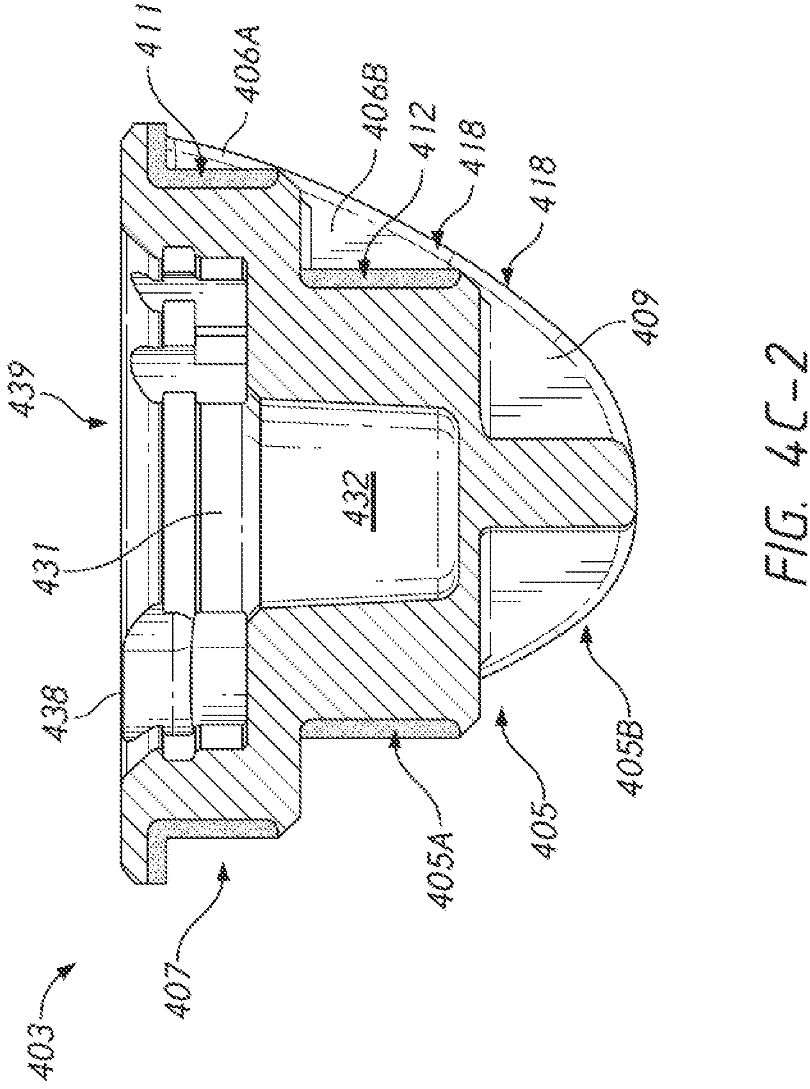
FIG. 4C is a side view of a stemless humeral anchor, according to another embodiment.

FIGS. 4C-4C-2 illustrate another example of a stemless humeral anchor 403, in which a fin structure extends along an entire length of the anchor 403. FIG. 4C is a side view of the anchor 403. FIG. 4C-1 is a top view of the anchor 403. FIG. 4C-2 is a side sectional view of the stemless humeral anchor 403 taken along section 4C-2-4C-2 of FIG. 4C-1. Unless otherwise noted, the components of FIGS. 4C-4C-2 may be the same as or generally similar to like-numbered components of FIG. 4A, with the reference numerals incremented by 100 relative to the reference numerals of FIG. 4A. For example, as with FIG. 4A, the anchor 403 of FIGS. 4C-4C-2 includes a distal fin 409 extending from a first distal section 405A to a distal end of the anchor 403. Moreover, the anchor 403 includes a radial projection 406B extending radially outward from the second distal surface 412. In addition, the anchor 403 can include an additional radial projection 406A extending radially outward from the first proximal surface 411. The projections 406A, 406B can be tapered inwardly and distally. In the illustrated embodiment, moreover, the projections 406A, 406B may be shaped so as to define a continuous surface with one another and with the fin 409. For example, as shown in FIGS. 4C and 4C-2, the fin 409 and the projections 406A, 406B may cooperate to define a radially- and distally-extending fin structure having a common outer rib 418. As shown, the fins 409 and projections 406A, 406B can have rounded edges. The radially- and distally-extending fin structure can extend from a collar 438 at the proximal end 439 of the anchor 403 to the distal end of the anchor 403, e.g., the distal end of the fin 409. Beneficially, the use of the elongated fin structure of FIGS. 4C-4C-2 can improve the securement of the anchor 403 to the humerus.

Figures 1, 4D:
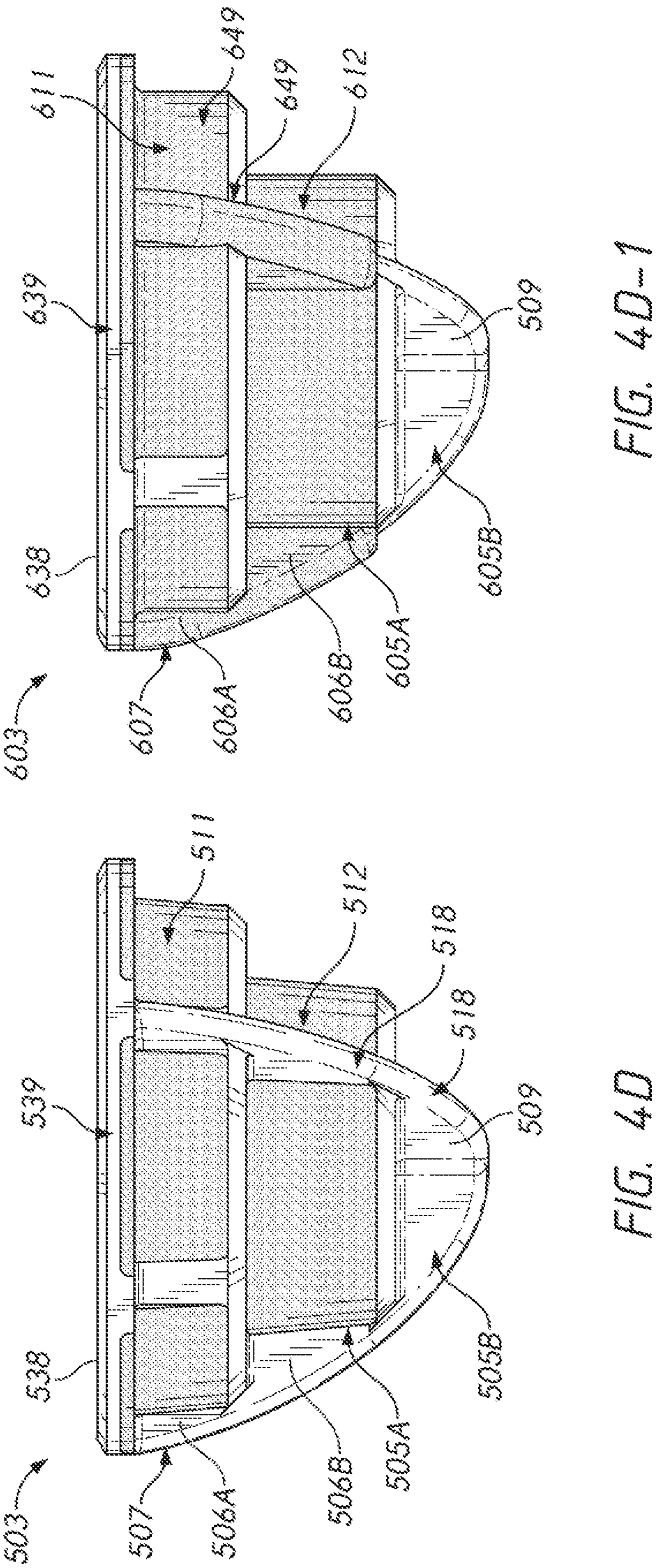

FIG. 4D illustrates another example of a stemless humeral anchor 503. Unless otherwise noted, the components of FIG. 4D may be the same as or generally similar to like numbered components of FIGS. 4A-4C-2, with the reference numerals incremented by 100. In the embodiment of FIG. 4D, the first exterior surface 511 and the second exterior surface 512 can comprise cylindrical surfaces with vertical sidewalls, e.g., sidewalls that are perpendicular to the collar 538 at the proximal end 539 of the anchor 503. A width of the proximal portion 507, which can be defined at least in part by the first exterior surface 511, can have a first width. A width of the first distal section 505A, which can be defined at least in part by the second exterior surface 512, can have a second width that is less than the first width. In various embodiments, the second width can be less than the first width in a range of about 0.5 mm to about 4 mm, in a range of about 1 mm to about 3 mm, or in a range of about 1.5 mm to about 2.5 mm, for example, by about 2 mm.

FIG. 4D-1 is a side view of a humeral anchor 603, according to another embodiment. The humeral anchor 603 may be generally similar to the humeral anchor 503 of FIG. 4D. For example, the anchor 603 can have a fin structure that extends from the collar 638 at the proximal end 639 to the distal end of the anchor 603. Moreover, the proximal portion 607 and the first distal section 605A can have straight cylindrical profiles. In the embodiment of FIG. 4D-1, a porous material 649 can be provided on at least a portion of the fin structure. For example, in the illustrated embodiment, the porous material 649 can be provided along the radial projections 606A, 606B, in addition to the exterior surfaces 611, 612 of the proximal and first distal sections 607, 605A. The porous material 649 can be provided to foster ingrowth of bone tissue into the radial projections 606A, 606B. In other embodiments, the porous material 649 can also be provided on the fins 609.

Figure 4E:
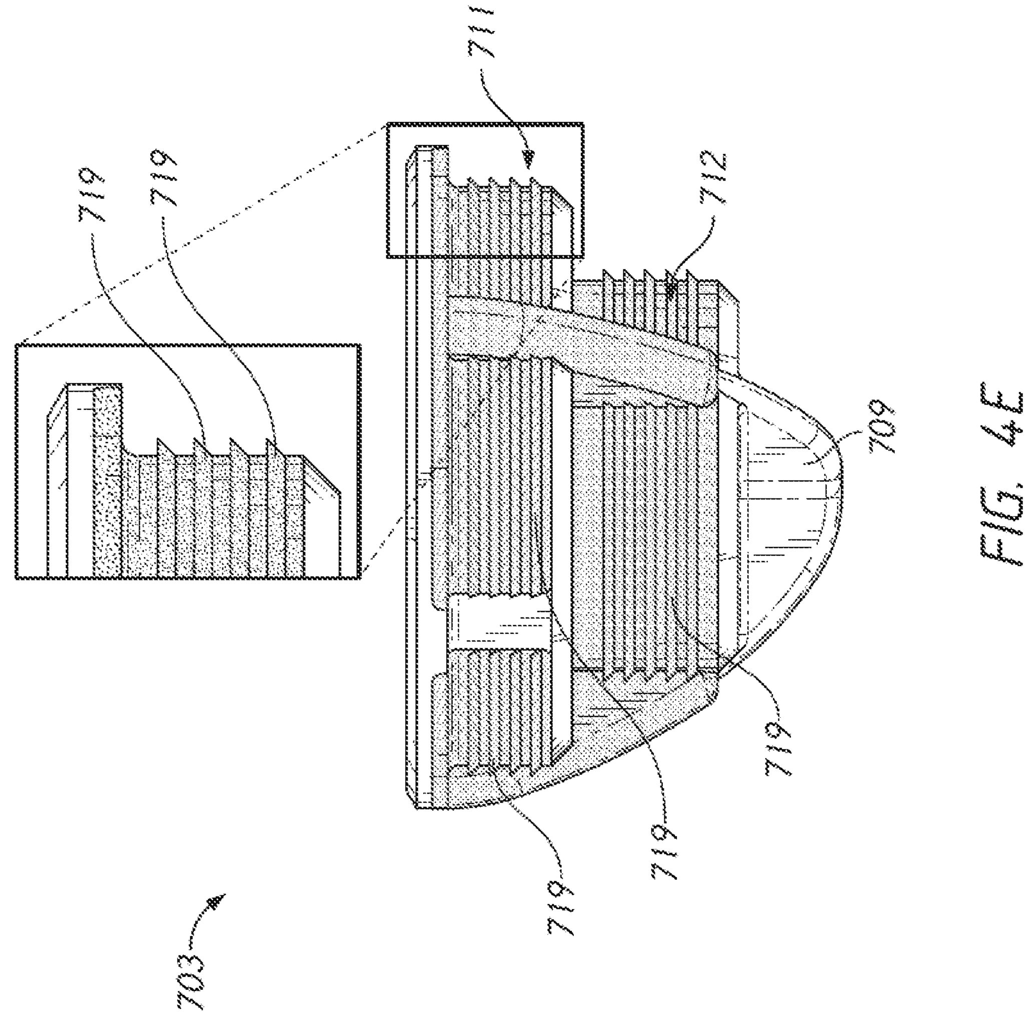
FIG. 4E is a schematic side view of a humeral anchor having a plurality of anchoring teeth, according to various embodiments.

FIG. 4E is a schematic side view of a stemless humeral anchor 703, according to another embodiment. Unless otherwise noted, the components of FIG. 4E may be the same as or generally similar to like-numbered components of FIG. 4D-1, with the reference numerals incremented by 100 relative to the reference numerals of FIG. 4D-1. In the embodiment of FIG. 4E, a plurality of teeth 719 can be provided on the first proximal surface 711 and/or on the second distal surface 712. In various embodiments, multiple teeth 719 can be provided on each of the first and second surfaces 711, 712. In other embodiments, teeth 719 may be provided on only one of the first and second surfaces 711, 712. As shown, each of the teeth 719 can comprise a proximally oriented face, surface, or extent. The teeth 719 can assist in securing the anchor 703 to the humerus. In various embodiments, the teeth 719 can comprise a metal. FIG. 4E shows that the teeth 719 can include one or a plurality of arcuate projections disposed around one or both of the surfaces 711, 712. The teeth 719 can include ring-like projections in some examples. The teeth 719 can include proximally larger and distally smaller structures. The teeth 719 can include a plurality of aligned ring-like structures, e.g., two, three, four or more ring-like projections on one and/or both of the surfaces 711, 712. One or more or all of the teeth 719 can present a proximally oriented surface that will engage bone matter and resist allowing the anchor 703 to back out of the humerus under expected operational loads.

Figures 1, 4F:
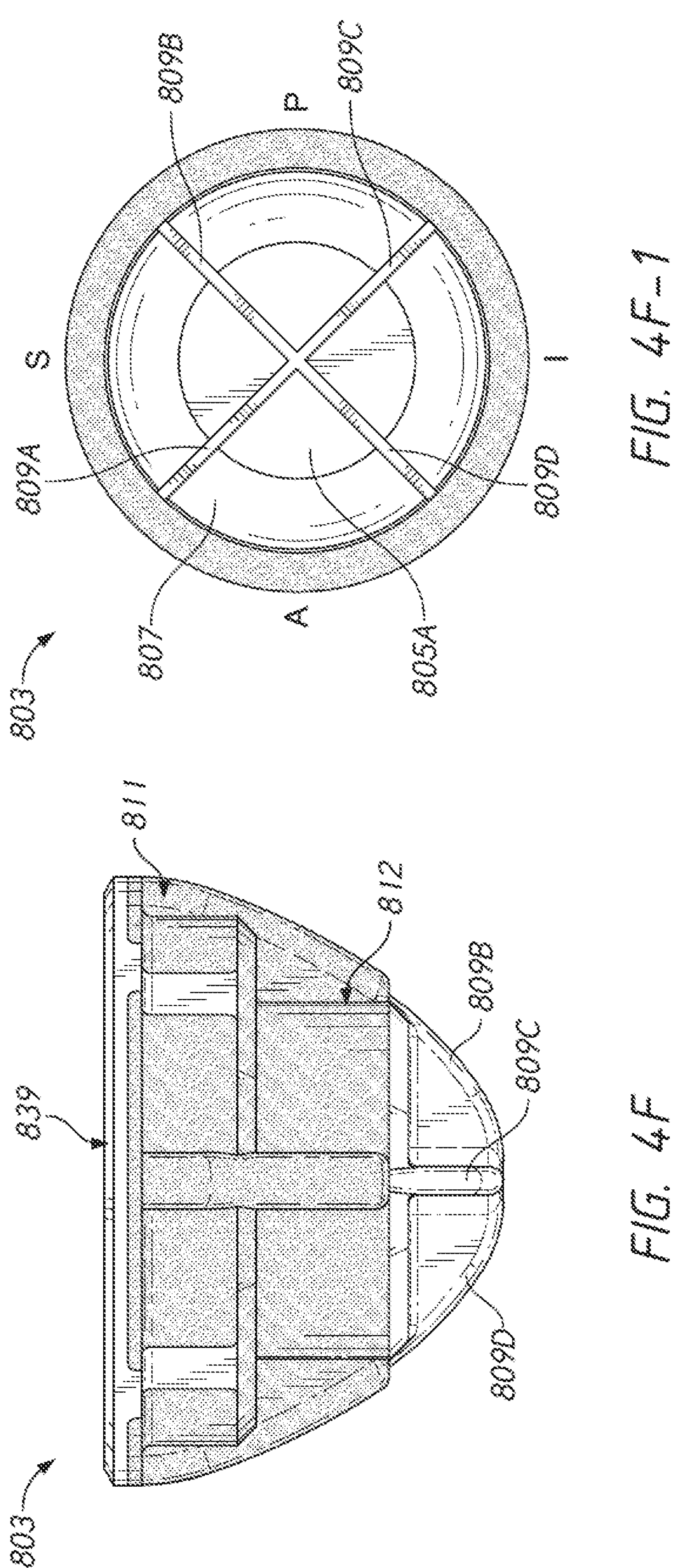

FIG. 4F is a schematic side view of a humeral anchor 803, according to another embodiment. FIG. 4F-1 is a schematic bottom view of the stemless humeral anchor 803 of FIG. 4-F. Unless otherwise noted, the components of FIGS. 4F-4F-1 may be the same as or generally similar to like-numbered components of FIG. 4E, with the reference numerals incremented by 100 relative to the reference numerals of FIG. 4E. Unlike the embodiment of FIG. 4E, in FIGS. 4F-4F-1, the anchor 803 includes four (4) fins 809A, 809B, 809C, and 809D. Fin 809A can be oriented diagonally relative to the anatomy so as to have respective directional components along the anterior direction A and the superior direction S. Fin 809B can be oriented can be oriented diagonally relative to the anatomy so as to have respective directional components along the posterior direction P and the superior direction S. Fin 809C can be oriented diagonally relative to the anatomy so as to have respective directional components along the posterior direction P and the inferior direction I. Fin 809D can be oriented diagonally relative to the anatomy so as to have respective directional components along the anterior direction A and the inferior direction I. As shown the fins 809A-809D can be evenly spaced apart, for example, by about 90°. The configuration of the anchor 803 is advantageous in providing one-third more surface area of engagement with the cancellous bone of the metaphysis of a humerus to which the anchor 803 is applied. Also, all four fins 809A-809D are positioned to resist a tilt out force in a direction more likely to be subject to such a force. Thus, with only one-third more fins, the tilt out resistance can be roughly doubled compared to the configuration and orientation of the anchor shown in FIG. 4B.

Figure 4G:
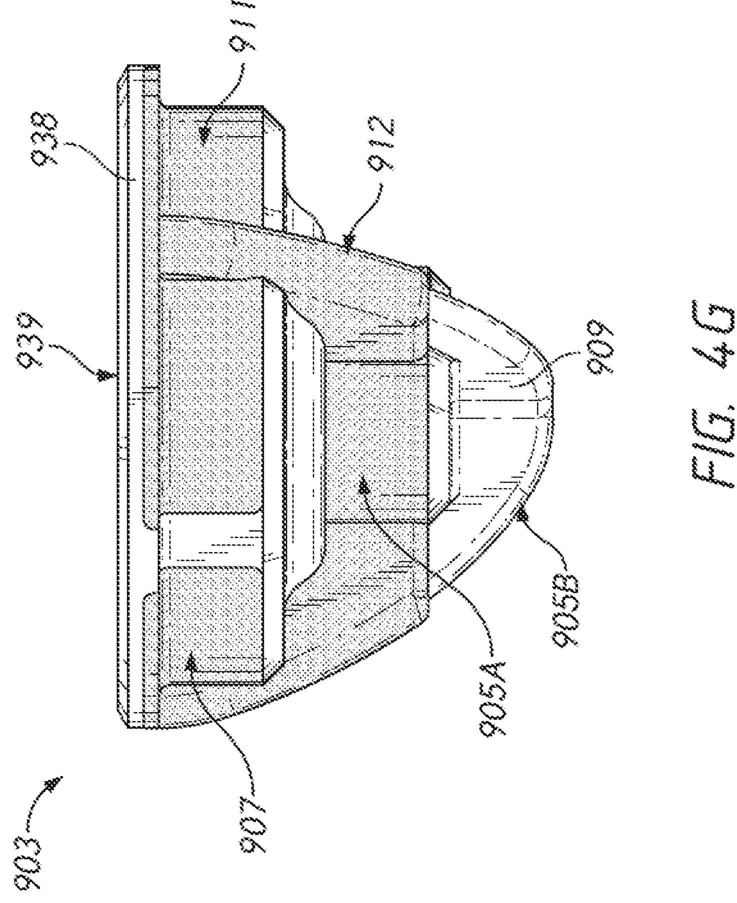
FIG. 4G is a side view of a stemless humeral anchor having a bone-preserving profile, according to another embodiment.

FIG. 4G is a side view of a humeral anchor 903 according to various embodiments. Unless otherwise noted the components shown in FIG. 4G may be the same as or generally similar to like numbered components of FIGS. 4A-4F-1, with the reference numerals incremented by 100 relative to FIGS. 4F-4F-1. In the embodiment of FIG. 4G, the first distal section 905A may be smaller than the bowl-shaped first distal sections 505A and 605A of FIGS. 4D-4D-1. The proximal portion 907 and the first distal section 905A may comprise straight cylindrical profiles with walls that are perpendicular to the collar 938 at the proximal end 939 of the anchor 903. The width of the proximal portion 907 can be at least 1 mm, at least 1.5 mm, or at least 2 mm larger than the width of the first distal section 905A. The narrow first distal section 905A can enhance the area of a fin 909 at the level of the distal section 905A in direct contact with bone matter when the anchor 903 is implanted. The anchor 903 of FIG. 4G can comprise a bone-preserving stemless anchor in which the distal section 905A of the distal portion 905 is narrower than the distal portion of other anchors disclosed herein. The narrower distal section 905A can enable the use of fin(s) 909 having increased surface area. By increasing the surface area of the fin 909 contacting the bone, the anchor 903 can be less susceptible to a lever-out force or other load that could potentially dislodge the anchor 903.

The size of the distal section 905A can be made sufficiently large enough, however, to receive the distal extension 163B of the coupler 168. In some embodiments, the width or size of the distal section 905A can be made slightly larger than the width of the distal extension 163B in a plurality of the sizes of anchors 903 in a kit. As explained above, in some kits, multiple sizes of stemless anchors 903 may be provided. In various embodiments, the widths of the proximal portion 907 and the distal portion 905 of the anchors 903 (e.g., the exterior surfaces 911, 912 and fin(s) 909) in a kit may vary so as to fit within differently-sized bone structures, but the width of the second or distal recess (similar to the second recess 232) may be about the same for each sized anchor 903 in the kit (or may vary only slightly). In some embodiments, a width of the second or distal recess for each anchor 903 in the kit may differ by less than 15%, less than 10%, less than 5%, or less than 1% of the width of a particular anchor 903 of the kit.

In the embodiment of FIG. 4G, a ratio of a first width of the first proximal recess (similar to the first recess 231) to a second width of the second distal recess (similar to the second recess 232) can be in a range of 2:1 to 3.25:1, in a range of 2.2:1 to 3.1:1, or in a range of 2.25:1 to 3:1. As explained above, in some embodiments, the widths of the second distal recesses of each anchor 903 of a kit may be about the same, or may vary only slightly. The first widths of the first proximal recesses of the anchors 903 of the kit may differ such that a ratio of the first width of the first proximal recess (similar to the first recess 231) of the largest anchor 903 in the kit to the first width of the first proximal recess of the smallest anchor 903 in the kit is in a range of 1.2 to 1.5, in a range of 1.25 to 1.45, or in a range of 1.3 to 1.4.

B. Examples Humeral Anchors With Stem Portions

For some patients it is preferred to provide enhanced or different anchorage of a humeral implant within the humerus H. The bone quality in the metaphysis M may be such that a stemless anchor would not provide adequate tilt out performance or would not be expected to sufficiently integrate with the bone. As such, an anchor with a distal portion adapted to reach to the diaphysis D of the humerus H may be a good choice for a patient.

Figure 5:
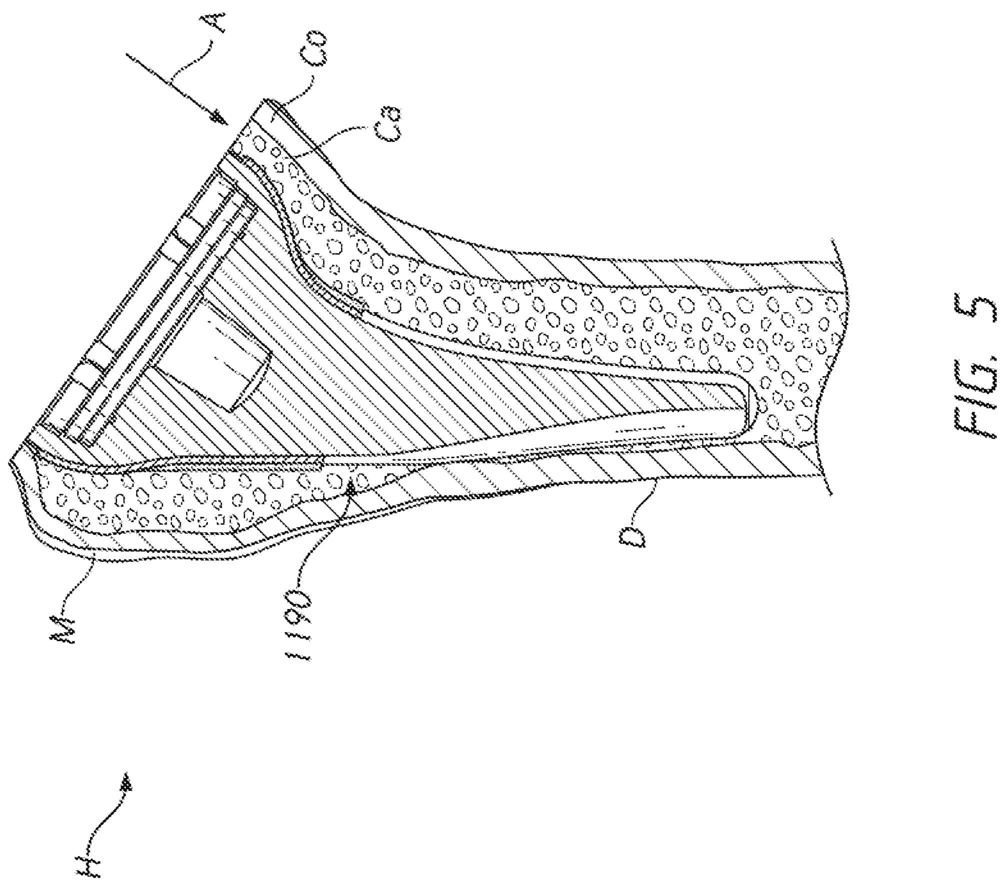
FIG. 5 is a side sectional view of an example of a humeral stem that has a distal portion that can extend into the diaphysis of the humerus.

FIG. 5 shows an example of a humeral stem 1190 that has a distal portion that can extend into the diaphysis D of the humerus H. The positioning of the humeral stem 1190 can be challenging. For example, it may be desired that a lateral side of a proximal end of the humeral stem 1190 (upper left side in FIG. 5) abut, engage or touch the cortical bone Co layer. This can provide a predictable performance of the humeral stem 1190 in the humerus H. Meanwhile, the medial side of the proximal end of humeral stem 1190 (upper right side in FIG. 5) may be spaced from the cortical bone Co due to the non-circular shape of the resected humerus H. More particularly, the distance from supero-lateral edge of the resection to the infero-medial edge of the resection may be larger than the diameter of the metaphysis portion of the humeral stem 1190 at the proximal end of the humeral stem 1190. As such, a portion of the cancellous bone Ca at the arrow A will not be engaged by the humeral stem 1190 and will be exposed following implantation of the humeral stem 1190. Although the cancellous bone Ca at the arrow A may be somewhat compressed by the method of inserting the humeral stem 1190 (discussed further below), the non-engaged state of the cancellous bone Ca at this location may result in disadvantageous processes such as stress shielding leading to resorption of the bone.

FIGS. 6A-6M illustrate various examples of a humeral stem 1200 that can be implanted in a resected humerus H. The humeral stem 1200 can be provided in the kit 100 as one of the plurality of stemmed humeral anchors 113. Any one or more of the features of the humeral stem 1200 can be incorporated into the humeral stem 1190, which can be provided in the kit 100.

Figures 6A, 6B:
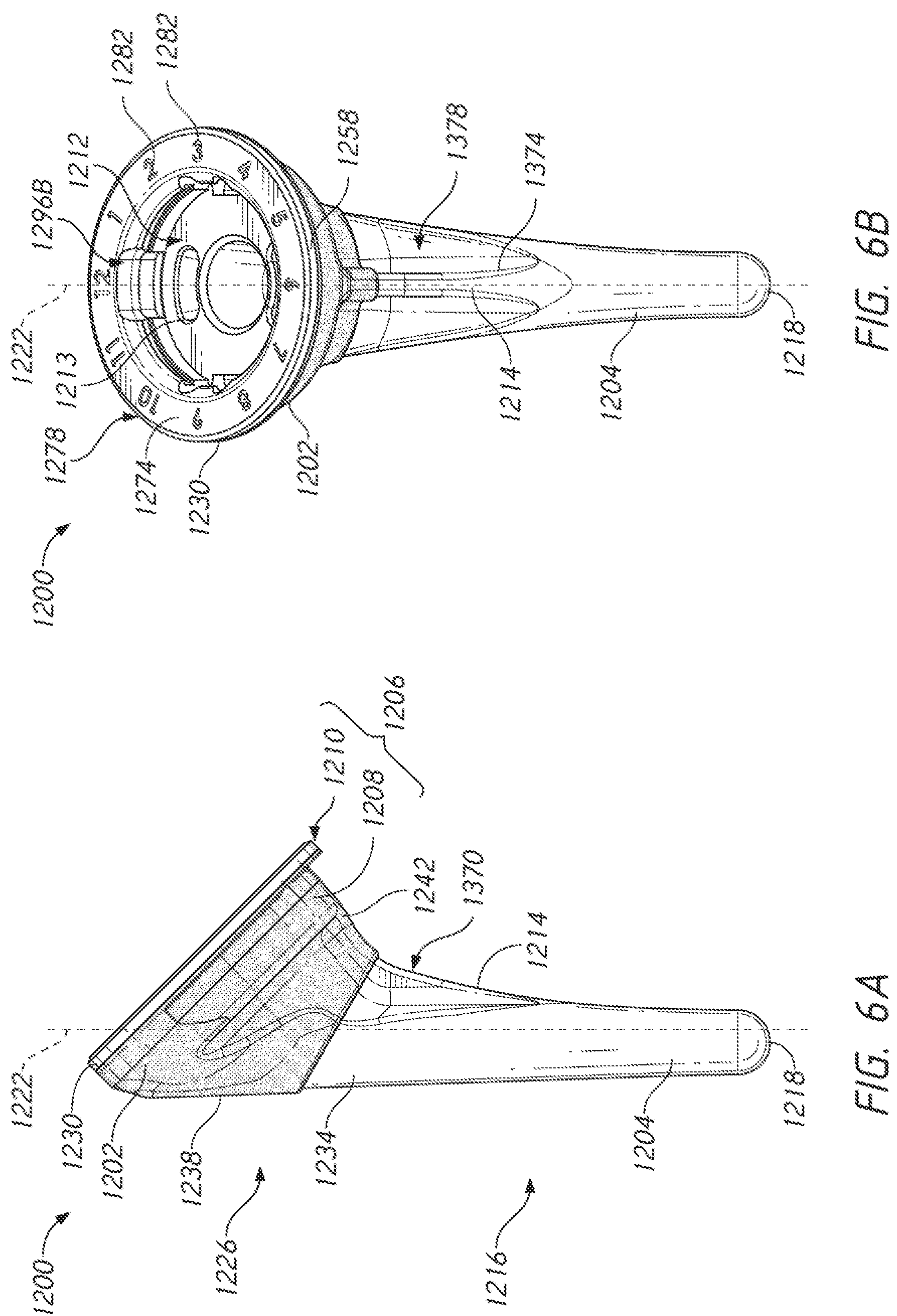
FIG. 6A is a side view of a humeral stem anchor, according to various embodiments.
FIG. 6B illustrates a proximal and medial aspect of the humeral stem anchor of FIG. 6A.

FIG. 6A shows that the humeral stem 1200 includes a metaphysis portion 1202 and a diaphysis portion 1204. The metaphysis portion 1202 is configured to be placed in the metaphysis M of a humerus H and the diaphysis portion 1204 is configured to be placed in the diaphysis D of the humerus H (see FIG. 5). The metaphysis portion 1202 has a larger area in any given cross-section thereof than the diaphysis portion 1204. The metaphysis portion 1202 is generally configured to occupy a large volume of the metaphysis M similar to the construction of the stemless anchors discussed above. In some cases, the metaphysis portion 1202 has an overall volume that is equal to or exceeds that of a corresponding size stemless implant in the kit 100. The diaphysis portion 1204 may be tapered in way that periphery will match and generally file the shape and volume of an intramedullary canal of the humerus H. At least the metaphysis portion 1202 has a cancellous bone interface 1206. The cancellous bone interface 1206 can include a portion of the outer surface of the humeral stem 1200 that is disposed and configured to touch the cancellous bone Ca and to provide a desired result between the humeral stem 1200 and the cancellous bone Ca or a function of preserving the cancellous bone Ca. In some cases, the cancellous bone interface 1206 includes a porous zone 1208 that is configured to provide or enhance bone in-growth in the humeral stem 1200. The porous zone 1208 can be a texture or a surface with pores sized to encourage bone matter to grow therein or thereon. The cancellous bone interface 1206 can include a cancellous bone compression member 1210 that is configured to reduce or minimize the effects of stress shielding.

FIG. 6B shows a proximal and medial aspect of the humeral stem 1200. This aspect includes an articular body interface 1212. The articular body interface 1212 is a portion to which an articular body, such as a reverse should implant articular body can be coupled. As will be discussed in greater detail below, the articular body interface 1212 can include features that receive and engage features of such an articular body, as discussed further below. The articular body interface 1212 can be located at a proximal end of the humeral stem 1200. The articular body interface 1212 can include indicia for directing a surgeon in orienting an articular body insert. The humeral stem 1200 also can include a tooling interface 1213. The tooling interface 1213 can be similar to the blind holes 245 discussed above in connection with the stemless humeral anchor 203. In some cases the kit 100 includes tools that can be used for both humeral stems and stemless anchors, as discussed below in connection with FIGS. 7-20. For such kits 100 the tooling interface 1213 can be identical between the humeral stem 1200 and a stemless implant as described above in connection with FIGS. 3A-4G.

A good outcome following implantation of the humeral stem 1200 in the humerus H will be the retention of the stem in a fixed position in the humerus H. An anti-rotation member 1214 seen in FIGS. 6A and 6B can reduce motion of the humeral stem 1200 in the humerus H, in particular rotation about a longitudinal axis 1222 of a distal portion 1216 of the humeral stem 1200. The anti-rotation member 1214 can be disposed in the metaphysis portion 1202. The anti-rotation member 1214 can extend along the metaphysis portion 1202 toward the diaphysis portion 1204. FIG. 6A shows that the humeral stem 1200 can have a porous portion generally corresponding to the metaphysis portion 1202 and a smooth portion extending from a distal end 1218 of the humeral stem 1200 toward the metaphysis portion 1202. The anti-rotation member 1214 can include a first portion extending into a porous portion and a second portion in the smooth portion. The anti-rotation member 1214 can extend continuously from the porous metaphysis portion 1202 into a transition region between the metaphysis portion 1202 and the diaphysis portion 1204.

FIG. 6B shows that the anti-rotation member 1214 can project from anterior and posterior zones of reduced volume. The anterior and posterior zones can be configured as proximally enlarged flutes which can accommodate volumes of preserved humeral bone below the resection plane. The anterior and posterior zones can be seen as concave profiles on a medial half of the body of the humeral stem 1200 from the anti-rotation member 1214 toward the lateral half of the humeral stem 1200. The anterior and posterior zones preserve humeral bone compared to a configuration where the flutes are not present, e.g., where the humeral stem 1200 is continuously convex in the region of the anti-rotation member 1214.

FIGS. 6A-6J further show that the humeral stem 1200 can include a distal portion 1216 that extends along the longitudinal axis 1222 proximally from the distal end 1218. The distal portion 1216 is tapered inwardly along the longitudinal axis 1222 toward the distal end 1218 of the humeral anchor 1200. The humeral stem 1200 includes a proximal portion 1226. The proximal portion 1226 extends distally from a proximal end 1230 of the humeral anchor humeral stem 1200. The humeral stem 1200 includes an outer surface 1234. The outer surface 1234 in the proximal portion 1226 is enlarged to occupy at least a majority of the volume of a metaphysis of the humerus into which the humeral anchor is to be disposed. The outer surface 1234 in the distal portion 1216 can be slender to fit within an intramedullary canal without substantial preparation thereof. The outer surface 1234 can be porous in part and can be smooth in part.

The humeral stem 1200 includes a lateral side 1238. The lateral side 1238 is configured to be disposed adjacent to a cortical wall of a lateral portion of a humeral metaphysis. As discussed further below a humerus can be prepared by resection and by reaming and broaching to prepare a space therein. In one approach the lateral side 1238 of the humeral stem 1200 is configured to be disposed adjacent to a lateral cortical bone wall or segment, e.g., an inner surface of a cortical bone layer. Such placement provides a consistent anatomic reference in the humerus in some techniques. Such placement allows a medial side 1242 to be consistently spaced relative to a medial cortical wall. For example, the medial side 1242 or a method of implanting the humeral stem 1200 can be configured to cause the medial side 1242 to be spaced apart from the medial cortical wall. Such spacing allows preserves the medial cortical wall such that the humeral stem 1200 is not likely to break through the medial cortical wall when the humeral stem 1200 is applied to the patient.

Figure 6D:
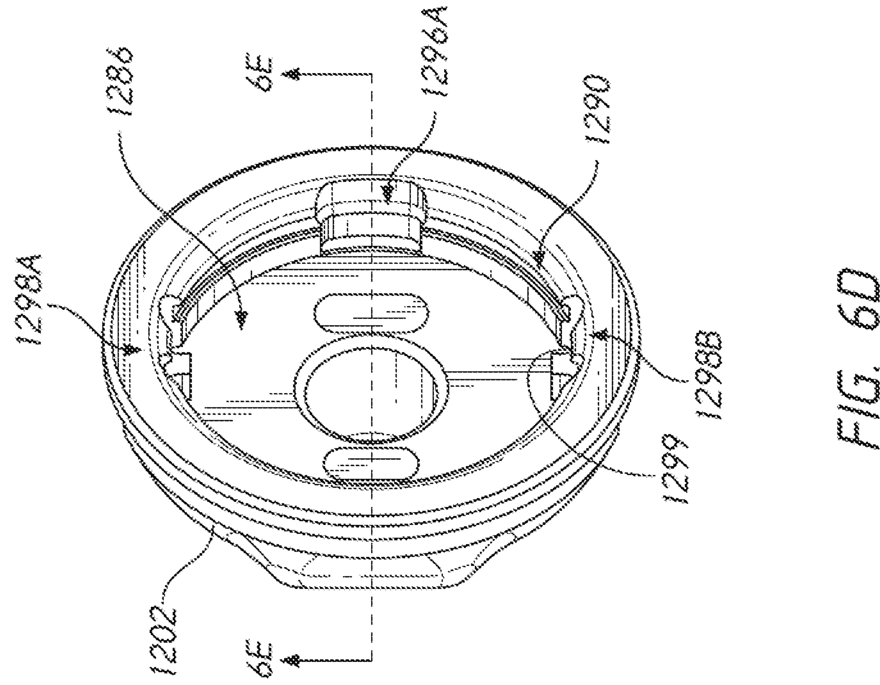
FIG. 6D is a perspective view of a proximal portion of a humeral stem anchor, according to various embodiments.
Figure 6C:
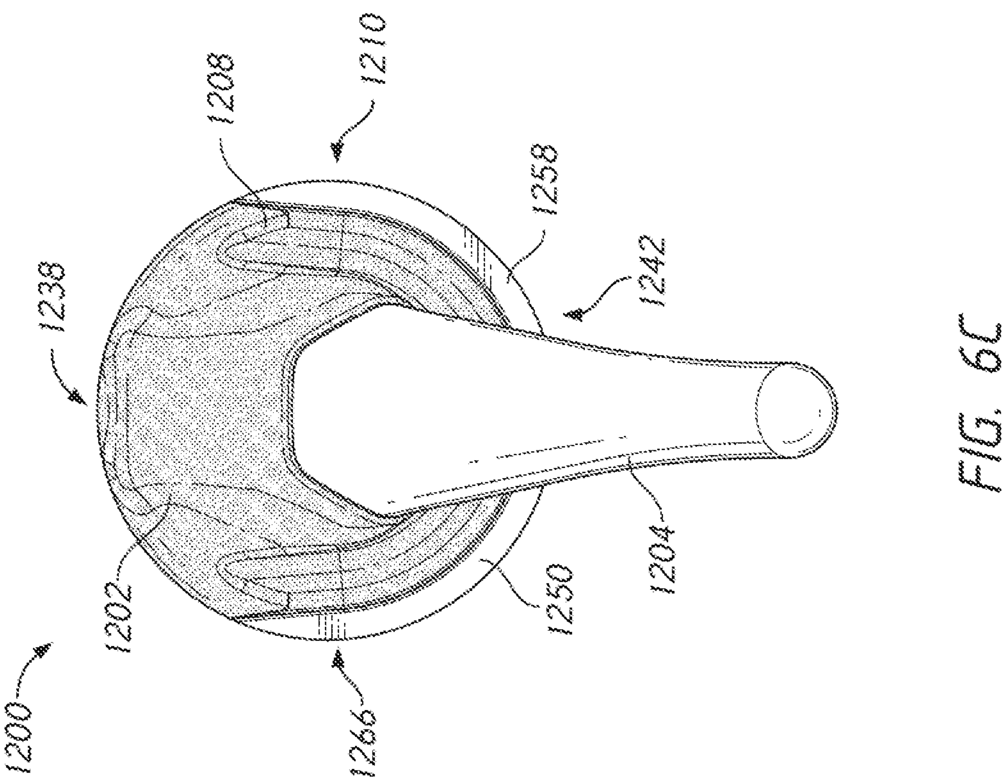
FIG. 6C illustrates a distal and lateral aspect of the humeral stem anchor of FIG. 6A, which includes a cancellous bone compression member.

FIGS. 6A and 6C provide additional details of the cancellous bone compression member 1210 in various examples. The cancellous bone compression member 1210 can include a bone compression surface 1250. The bone compression surface 1250 can be disposed adjacent to or at the proximal end 1230 of the humeral anchor 1200. In one example, the bone compression surface 1250 is disposed about the medial side 1242 of the proximal portion 1226. The bone compression surface 1250 can be disposed about only the medial side 1242, e.g., about a portion of the periphery of the proximal end 1230 not including the lateral side 1238 of the humeral stem 1200. The cancellous bone compression member 1210 is configured to extend from the medial side 1242 of the proximal portion to the cortical wall of the medial side of the humeral metaphysis when implanted in a humerus. FIG. 5 shows a gap at the arrow A between the medial side of the humeral stem 1190 and the inside surface or wall of the cortical bone Co. The bone compression surface 1250 can be configured to bridge the gap or space left by the humeral stem 1190. By closing the gap shown at the arrow A bone loss due to stress shielding can be reduced, minimized or even eliminated. This can result in a more stable, long lasting implant and also can reduce, minimize or even eliminate instances of revision surgery which can be traumatic and in some cases not even possible for aging patients.

The bone compression surface 1250 can comprise a distal facing side of a flange 1258. The flange 1258 can extend outward from the proximal end 1230 of the proximal portion 1226 of the humeral stem 1200. The shape of the outer periphery of the flange 1258 can be any suitable shape. For example, the flange 1258 can have a circular outer periphery 1266. The circular outer periphery 1266 can have a radius corresponding to a radius of the lateral side of the proximal portion 1226 of the humeral stem 1200. The proximal end 1230 of the humeral stem 1200 can have an annular face with a circular shape. A radius of the circular shape can extend to the same lateral position as the lateral side 1238 of the proximal portion 1226 adjacent to the annular face. A radius of the circular shape can extend farther medially than the medial side 1242 of the proximal portion 1226 adjacent to the annular face. This can provide an overhang configuration of the bone compression surface 1250 on the medial side 1242 and less or no bone compression surface on the lateral side 1238. A result of this configuration is that the width of the bone compression surface 1250 can taper at least at one and in some cases at both opposing ends thereof until the bone compression surface 1250 is not present, e.g., from about 10 o'clock to about 2 o'clock as seen in FIG. 6C. In the illustrated embodiment, the bone compression surface 1250 is present in more than one-half of the periphery of the cancellous bone compression member 1210. The bone compression surface 1250 can be present in less than one-half of the periphery of the cancellous bone compression member 1210, e.g., only between 8 o'clock and 4 o'clock in one example. The bone compression surface 1250 could be present entirely around the proximal end 1230 with a varying width, e.g., with a lesser width on the lateral side 1238.

In a further example, the configuration of the cancellous bone compression member 1210 can be made for a patient in a patient specific manner. For example, in various embodiments, the shoulder of the patient (e.g., the humerus and/or glenoid) can be imaged during pre-operative imaging procedures. The cancellous bone compression member 1210 can be shaped to specifically match the patient's anatomy based on the imaging performed before surgery. For example, in various embodiments, the cancellous bone compression member 1210 can be manufactured using various types of additive manufacturing techniques such as three-dimensional (3D) printing. The image data representative of the patient's cancellous bone structure can be transmitted to 3D printing machinery which can manufacture the cancellous bone compression member 1210 to substantially match or conform to the patient's cancellous bone tissue. The member 1210 can be shaped to extend at least to an inner wall portion of a cortical bone layer. The member 1210 can be shaped to extend beyond an inner wall portion of a cortical bone layer. The member 1210 can be shaped to follow the shape of the periphery of the humerus at the resection surface. These configurations can be made patient specific to reduce, minimize or eliminate stress shielding and concomitant bone loss. Accordingly, various embodiments disclosed herein can beneficially provide patient-specific structures to improve the fit of the anchor within the humerus.

FIG. 6B shows that the humeral stem 1200 can have an annular surface 1274 disposed at a proximal face 1278 of the humeral anchor. The flange 1258 can comprise a portion of the annular surface 1274 of the proximal face 1278. In some cases, the flange 1258 includes the bone compression surface 1250 on one side and the annular surface 1274 disposed on the opposite side thereof. The annular surface 1274 can include indicia helpful in orienting an articular component or assembly relative to the humerus of the patient. The annular surface 1274 can include rotational orientation indicia 1282 formed on or in the annular surface 1274 disposed at the proximal face 1278 of the humeral anchor 1200. In the illustrated embodiment, the rotational orientation indicia 1282 are numbers in the form of a clock face to indicate twelve discrete rotational positions. While this form of the rotational orientation indicia 1282 is intuitive, the indicia can be fewer or more numbers, letters, colors or other indicia or combination of indicia. In some cases, an articular assembly or component to be coupled with the humeral stem 1200 is asymmetric such that the rotational position thereof relative to the humeral stem 1200 changes the bio-mechanics of the assembly. The indicia on the annular surface 1274 can guide the surgeon on placing the articular assembly or component, as discussed further below. In brief, the indicia on the humeral stem 1200 (whether a trial implant or a final implant) can be used during a trial for a group of articular components or assemblies to indicate a desired position. Then, when the final implant is initially placed in the opened joint space the indicated orientation can be replicated prior to permanent connection of the final articular component or assembly with the humeral stem 1200.

Figure 6F:
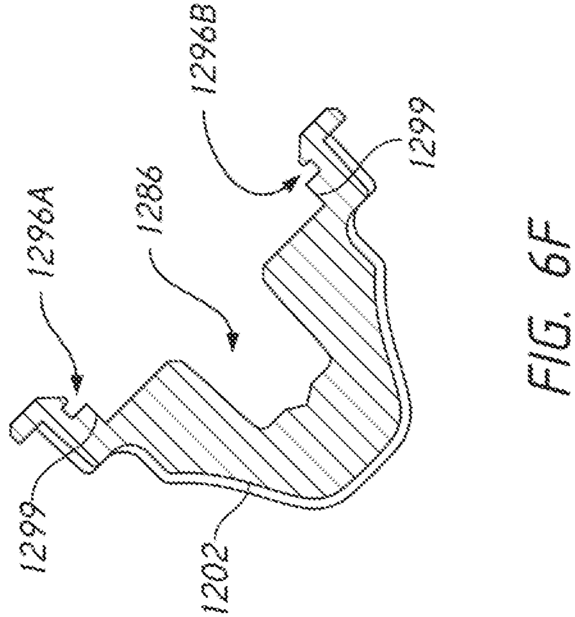
FIG. 6F is a sectional view of the humeral stem anchor of FIG. 6E, taken along section 6F-6F.
Figure 6E:
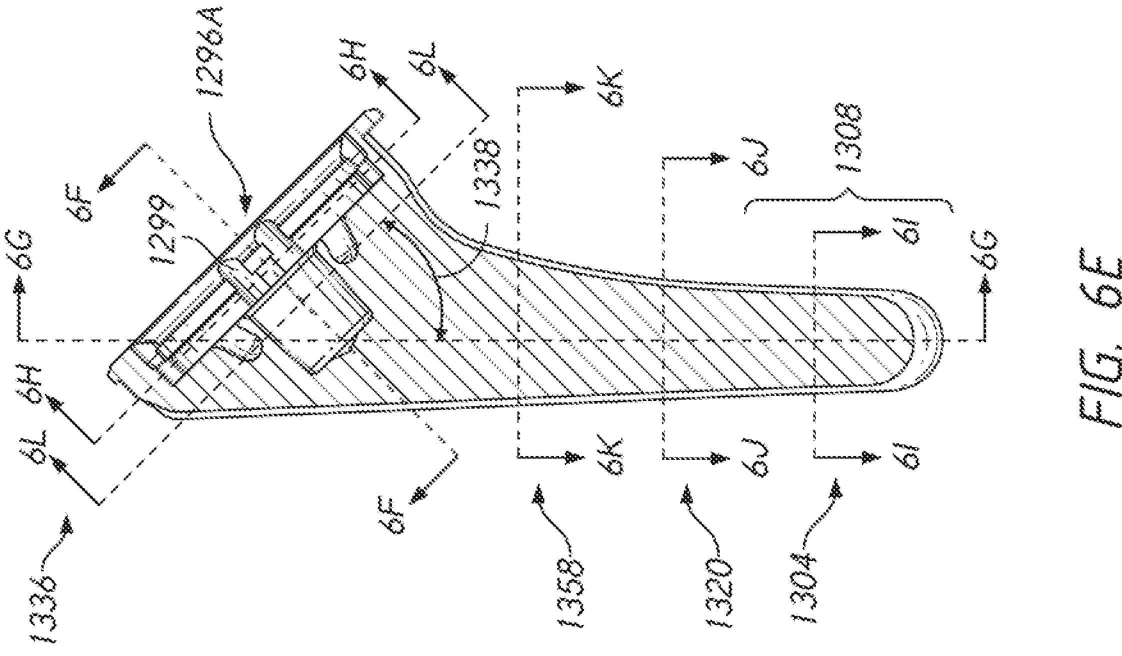
FIG. 6E is a side sectional view of the humeral stem anchor of FIG. 6D, taken along section 6E-6E of FIG. 6D.
Figure 6H:
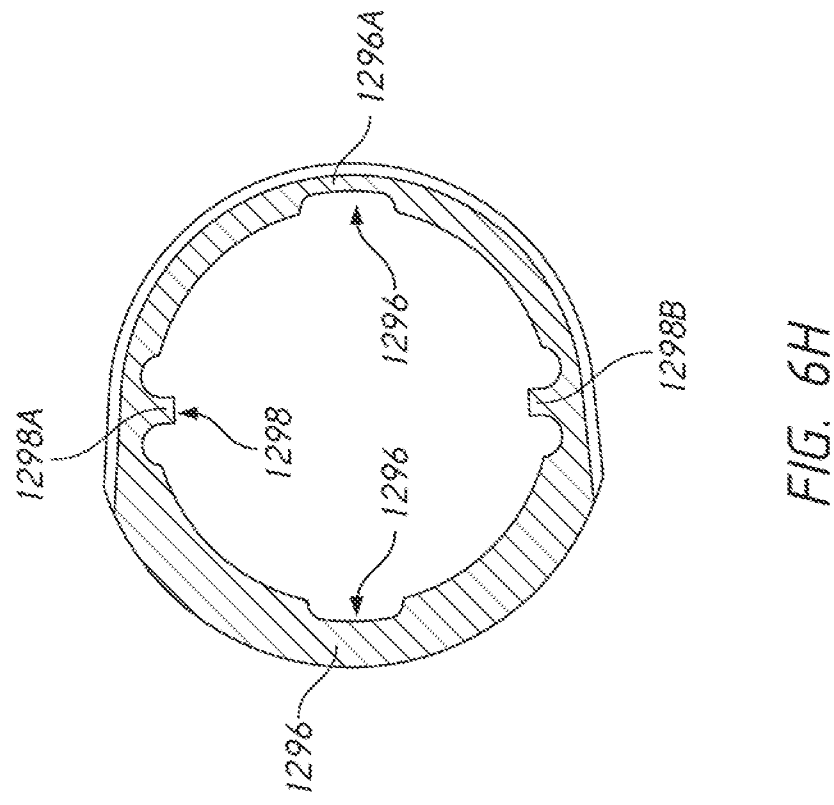
FIG. 6H is a sectional view of the humeral stem anchor of FIG. 6E, taken along section 6H-6H.
Figure 6G:
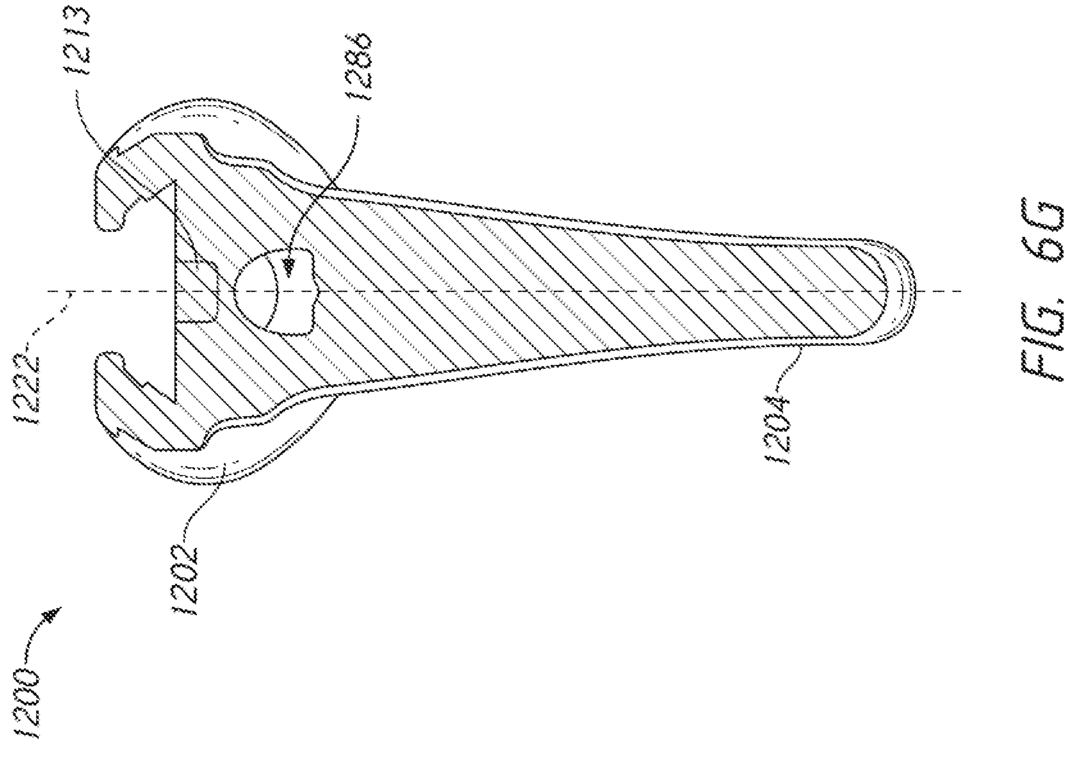
FIG. 6G is a sectional view of the humeral stem anchor of FIG. 6E, taken along section 6G-6G.

FIGS. 6D-F show details of the proximal portion 1226, in particular features for connecting an articular component or articular assembly therewith. The humeral stem 1200 includes a recess 1286 that extends distally from the proximal end 1230 of the humeral stem 1200 and into the proximal portion 1226. The recess 1286 can be surrounded by an inner periphery 1290 disposed about the recess 1286. The inner periphery 1290 can be disposed adjacent to the proximal end 1230 of the humeral anchor 1200. The inner periphery 1290 can be a circular wall facing toward the center of the recess 1286. The inner periphery 1290 can include one or more features to engage an articular component, such as a reverse polymer insert or an anatomic articular assembly. The inner periphery 1290 can include a locking feature 1294 disposed in the inner periphery 1290. The locking feature 1294, e.g., a concave locking feature 1296A, is aligned with the bone compression surface 1250. The locking feature 1294 can have a structure similar to locking features discussed above in connection with the stemless humeral anchor 203 in FIGS. 3A-3C. In one embodiment, the locking feature 1294 comprises a concave locking feature 1296 disposed in the inner periphery 1290. The concave locking feature 1296 can be configured to provide an interference fit for or with an articular body, such as a reverse shoulder implant articular body. The concave locking feature 1296 can include a first concave locking feature 1296A and a second concave locking feature 1296B. The second concave locking feature 1296B is disposed opposite the first concave locking feature 1296A. The first concave locking feature 1296A and the second concave locking features 1296B are disposed at medial and lateral portions of the humeral stem 1200 respectively in one embodiment.

The locking feature 1294 can include a convex locking feature 1298 disposed in the inner periphery 1290. The concave locking feature 1298 can be spaced apart from the convex locking feature 1296. In one embodiment, the convex locking feature 1298 includes a first convex locking feature 1298A and a second convex locking feature 1298B disposed opposite the first convex locking feature 1298A, e.g., at anterior and posterior positions. The convex locking feature 1298 can include an elongate fin 1299 projecting toward the recess 12986. The elongate fin 1299 can be configured to engage a periphery of an articular component, as discussed further below.

The profile of the humeral stem 1200 can be configured for a combination of snug fit in the diaphysis D of a humerus H and for enhanced engagement with bone in a metaphysis M of the humerus H. The distal portion 1216, e.g., the diaphysis portion 1204 can include a circular periphery 1300 at a first location 1304 along the longitudinal axis 1222 of the humeral anchor 1200 adjacent to the distal end 1218, as shown in FIG. 6I. The first location 1304 can be disposed along a length 1308. The length 1308 can have one or more circular peripheries disposed along the length 1308, e.g., from the distal end 1218 to or beyond the first location 1304.

Figure 6J:
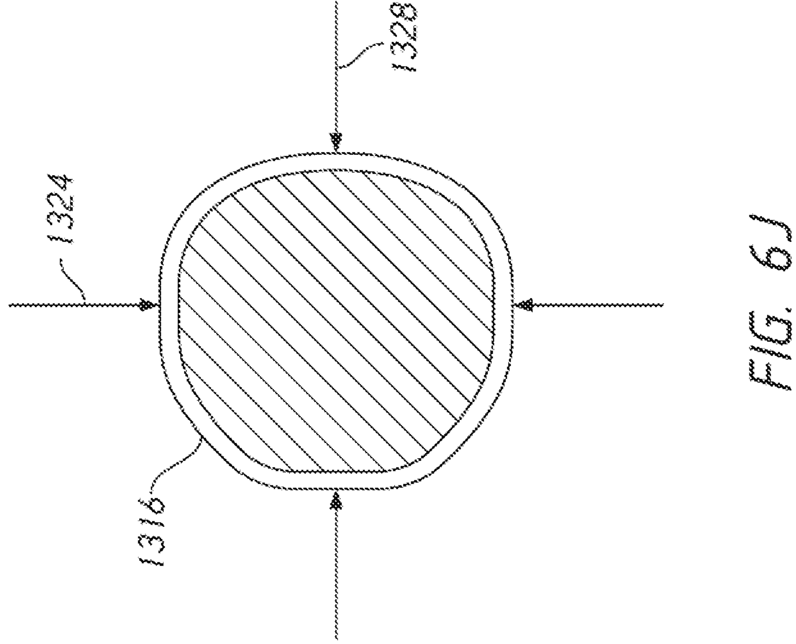
FIG. 6J is a sectional view of the humeral stem anchor of FIG. 6E, taken along section 6J-6J.
Figure 6I:
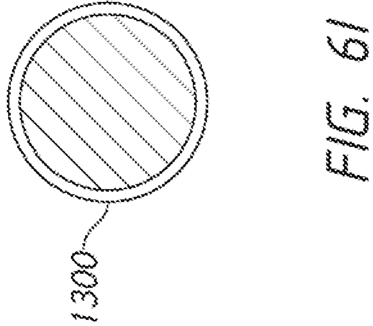
FIG. 6I is a sectional view of the humeral stem anchor of FIG. 6E, taken along section 6I-6I.

The profile of the humeral stem 1200 can change from circular at or adjacent to the distal end 1218 to an oblong periphery 1316 at a second location 1320 disposed between the first location 1304 and the proximal end 1230 of the humeral stem 1200, as shown in FIG. 6J. The oblong periphery 1316 can include a first dimension 1324 in an anterior-posterior direction and a second dimension 1328 in a medial lateral direction. The second dimension 1328 is larger than the first dimension 1324. In one configuration, the oblong profile at the second location 1320 can provide a circular periphery, e.g., with the same radius or a larger radius than the radius at the first location 1304 at a lateral side of the humeral stem 1200 and a second curved profile on the medial side of the humeral stem 1200. For example, the second curved profile can be of a smaller radius of curvature or can be a non-circular shape such as oval or ellipse so that the medial side of the humeral stem 1200 occupies more space medially when disposed in the humerus H than does the lateral side of the circular curvature. The second location 1320 can be proximal of the first location 1304.

Figures 6K, 6L:
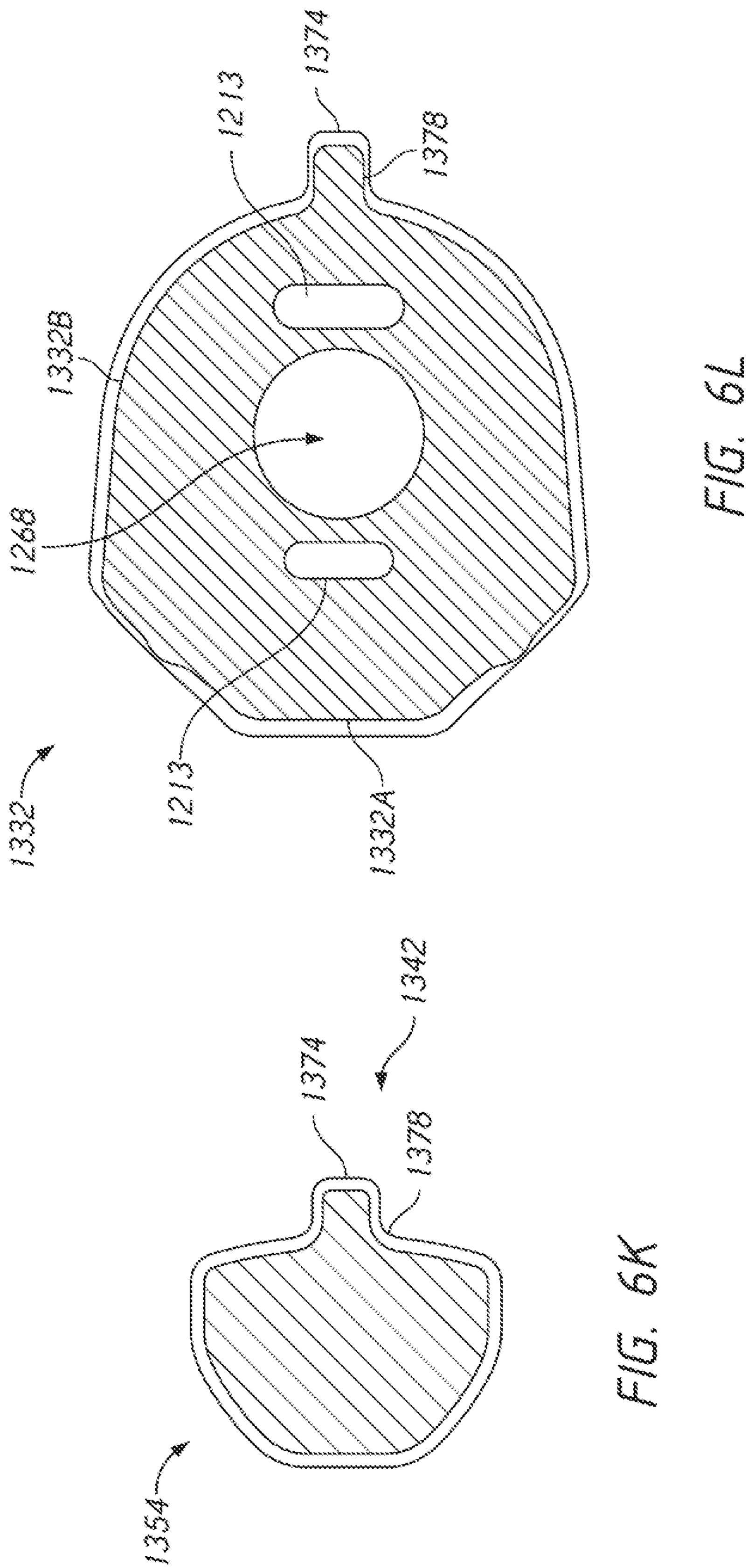
FIG. 6K is a sectional view of the humeral stem anchor of FIG. 6E, taken along section 6K-6K.
FIG. 6L is a sectional view of the humeral stem anchor of FIG. 6E, taken along section 6L-6L.

FIGS. 6E and 6L show that further proximal of the second location 1320, an at least partially polygonal periphery 1332 can be provided at a third location 1336. The third location 1336 can be disposed between the second location 1320 and the proximal end 1230 of the humeral anchor 1200. The at least partially polygonal periphery 1332 can be disposed in a cross-section oriented at an angle 1338 to the longitudinal axis 1222 of the distal portion 1216 and parallel to the proximal end 1230 of the humeral anchor 1200. The sides of the at least partially polygonal periphery 1332 can include a portion 1332A with a smaller medial-lateral dimension from a widest anterior-posterior dimension to a lateral side of the periphery 1332 and a portion 1332B with a larger medial-lateral dimension from a widest anterior-posterior dimension to a medial side of the periphery 1332. Thus the humeral stem 1200 can extend farther and fill more volume in the medial direction at the third location 1336 than in the lateral dimension. This is consistent with the approach to align the lateral side of the humeral stem 1200 with a projection of the intramedullary canal and to have the medial side project medially to fill a more complex space defined between a lateral cortical bone wall and a medial cortical bone wall. The position of the recess 1286 is seen to be shifted medially of the widest part of the at least partially polygonal periphery 1332.

FIGS. 6E and 6K show that between the third location 1336 and the second location 1320 there can be a second at least partially polygonal periphery 1354. The periphery 1354 can be disposed at a fourth location 1358 between the second location 1320 and the proximal end 1230 of the humeral anchor 1200. The second at least partially polygonal periphery 1354 can include a curved convex side configured to be oriented laterally. The second at least partially polygonal periphery 1354 can include a more anterior-posterior oriented side 1342 disposed between ends of the portion 1332B. Between the fourth location 1358 and the second location 1320 the humeral stem 1200 can transition from a configuration in which the lateral portion thereof has a smaller curvature, e.g., is more curved, and the medial portion thereof has a larger curvature, e.g., is flatter than the lateral portion, (see FIG. 6K) to a configuration in which the lateral portion thereof has a larger curvature, e.g., is flatter, and the medial portion thereof has a larger curvature, e.g., is more curved than the lateral portion (see FIG. 6L). This transition can be mostly a result in a change in curvature on the medial side reflecting a higher volume of bone to fill on the medial side when the stem is maintained straight or superior-inferior, e.g., along a direction corresponding to a projection of the lateral inner cortical wall of the intramedullary canal.

An anti-rotation fin 1370 can be disposed along one or more sides of the humeral stem 1200. In one embodiment, the anti-rotation fin 1370 is disposed along a medial side of the humeral stem 1200. The anti-rotation fin 1370 can be found in the at least partially polygonal periphery 1332 adjacent to the proximal end 1230 in one embodiment. The anti-rotation fin 1370 can be found in the second at least partially polygonal periphery 1354 in one embodiment. In one embodiment, the anti-rotation fin 1370 includes a projection 1378 that can extend in a medial direction from the generally anterior-posterior oriented side or portion of the second at least partially polygonal periphery 1354. The anti-rotation fin 1370 can extend continuously from the at least partially polygonal periphery 1338 at the third location 1336 to the second at least partially polygonal periphery 1354 at the fourth location 1358. The anti-rotation fin 1370 can emerge as the humeral stem 1200 transitions from a generally round profile in the length 1308 extending proximally from the distal end 1218 to a medially extended configuration, e.g., to a at least partially polygonal periphery between the first location 1304 and the proximal end 1230.

The anti-rotation fin 1370 is important in maintaining the stability of the humeral stem 1200 in the humerus H. Stability of the humeral stem 1200 is important to prevent dislocation of the implant, which if severe can result in revision surgery, which is a sub-optimal outcome for patients. Even where revision surgery is not required, movement of the humeral stem 1200 can change the biomechanics of the shoulder joint post-surgically. As discussed above, in some combinations an articular component is coupled with the humeral stem 1200 in a rotational position that provides prescribed biomechanics. Rotation of the humeral stem 1200 relative to the humerus H changes the angles between the arm and the scapula, which shifts the biomechanics from that which was prescribed. This can result in sub-optimal arm motion, which can lead to fatigue, injury, damage to the scapula, e.g., avoidable scapular notching, and in an extreme case the need for unwanted revision surgery.

Figure 6M:
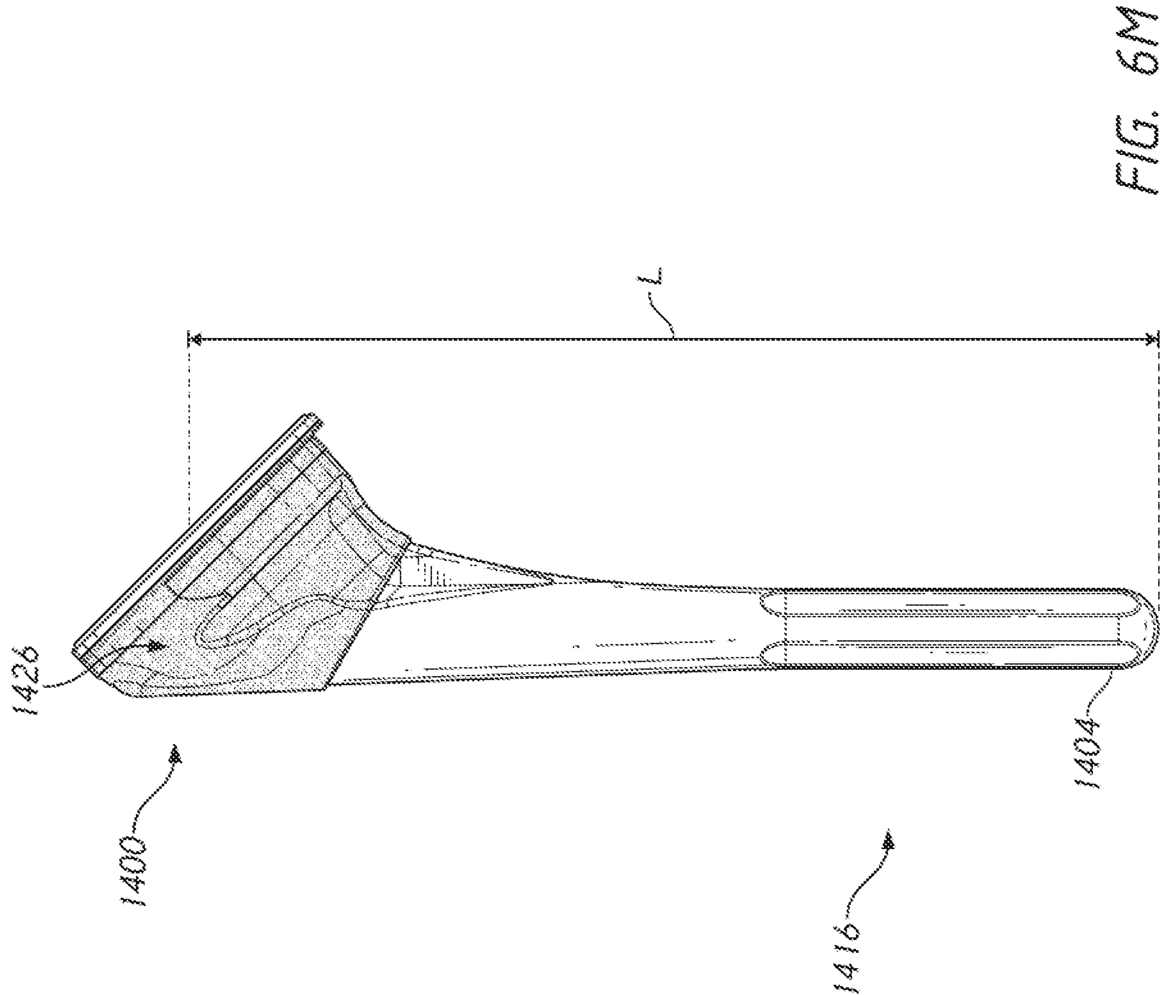
FIG. 6M is a side view of a stem humeral anchor having an extra long length, according to another embodiment.

FIG. 6M is a side view of a humeral stem anchor 1400 having an extended distal portion providing a length L. As with the embodiments of FIGS. 6A-6L, the anchor 1400 can comprise a proximal portion 1426 and a distal portion 1416. The distal portion 1416 can comprise an elongate stem 1404 extending from the proximal portion 1426. As explained above, the proximal portion 1426 can comprise shared locking or engagements features with the stemless and stemmed humeral anchors described above, such that the anchor 1400 can be used with anatomical articular components and reverse articular components. The anchor 1400 of FIG. 6M can have a length L which may be suitable for larger patients or for patients with higher degrees of bone damage or intraoperative fractures. In various embodiments, the length L of the anchor 1400 of FIG. 6M can be in a range of 120 mm to 200 mm, in a range of 130 mm to 180 mm, or in a range of 140 mm to 160 mm. Table 1 below illustrates example lengths for standard stem lengths, long stem lengths, and extra-long stem lengths.

IV. Shoulder Arthroplasty Methods and Instrumentation

The humeral anchors described above can be implanted following methods discussed below in connection with FIGS. 7-21. These methods can advantageously employ certain tools and instruments that can be shared among the stemless anchors and the anchors with stems. This provides advantages in reducing the training required to complete a surgical procedure.

A. Methods of Implanting Humeral Anchors

FIGS. 7-16 illustrate a method of preparing a humerus H to receive implant components and assemblies disclosed herein. The method can be used with bone of typical hardness and bone quality.

A resection step 1500 is performed in an initial part of the method. The resection step 1500 involves applying an intramedullary cutting block assembly 1504 to the humerus H. The resection step 1500 can include an intramedullary rod 1506 that can be advanced into a proximal end of the humerus H, e.g., through a lateral portion of an articular surface of the humerus H. The intramedullary rod 1506 can have a depth stop 1508 disposed at a proximal end thereof. The depth stop 1508 can be configured to limit the advancement of the intramedullary rod 1506 to a selected extent. The intramedullary cutting block assembly 1504 can also have a handle extending proximally from the depth stop 1508. The handle can have one or more markings and apertures to aid in the process of placing the intramedullary cutting block assembly 1504, e.g., aligning the assembly with the humerus H. The intramedullary cutting block assembly 1504 can include a cross-arm 1512 that extends laterally from the handle. The cross-arm 1512 can be positioned rotationally about a longitudinal axis of the intramedullary rod 1506. The intramedullary cutting block assembly 1504 also can include a boom 1516 that extends therefrom to hold a cutting block 1520 in a proper position. For example, the cutting block 1520 can be suspended at an anatomic neck of the humerus H. In some procedures, it is desired to resect the humerus H at the anatomic neck to separate the articular surface of the humerus H from the rest of the humerus. The separation of the articular surface from the rest of the humerus H creates a resection surface seen, for example, in FIG. 8.

In some cases, a surgeon may prefer not to insert the intramedullary rod 1506 into the humerus H and may prefer to use an extramedullary cutting block assembly 1524. The extramedullary cutting block assembly 1524 includes a cutting block 1520A that is similar to the cutting block 1520. The cutting block 1520A is supported from below, e.g., with a mounting block member that can be pinned to an external cortical wall surface of the diaphysis of the humerus H. The extramedullary cutting block assembly 1524 has an advantage in that there is no rod passing through the plane of the resection. The intramedullary cutting block assembly 1504 has an advantage in that there is no need to drill any holes in any part of the humerus H that will remain following the surgery.

Figures 7, 8:
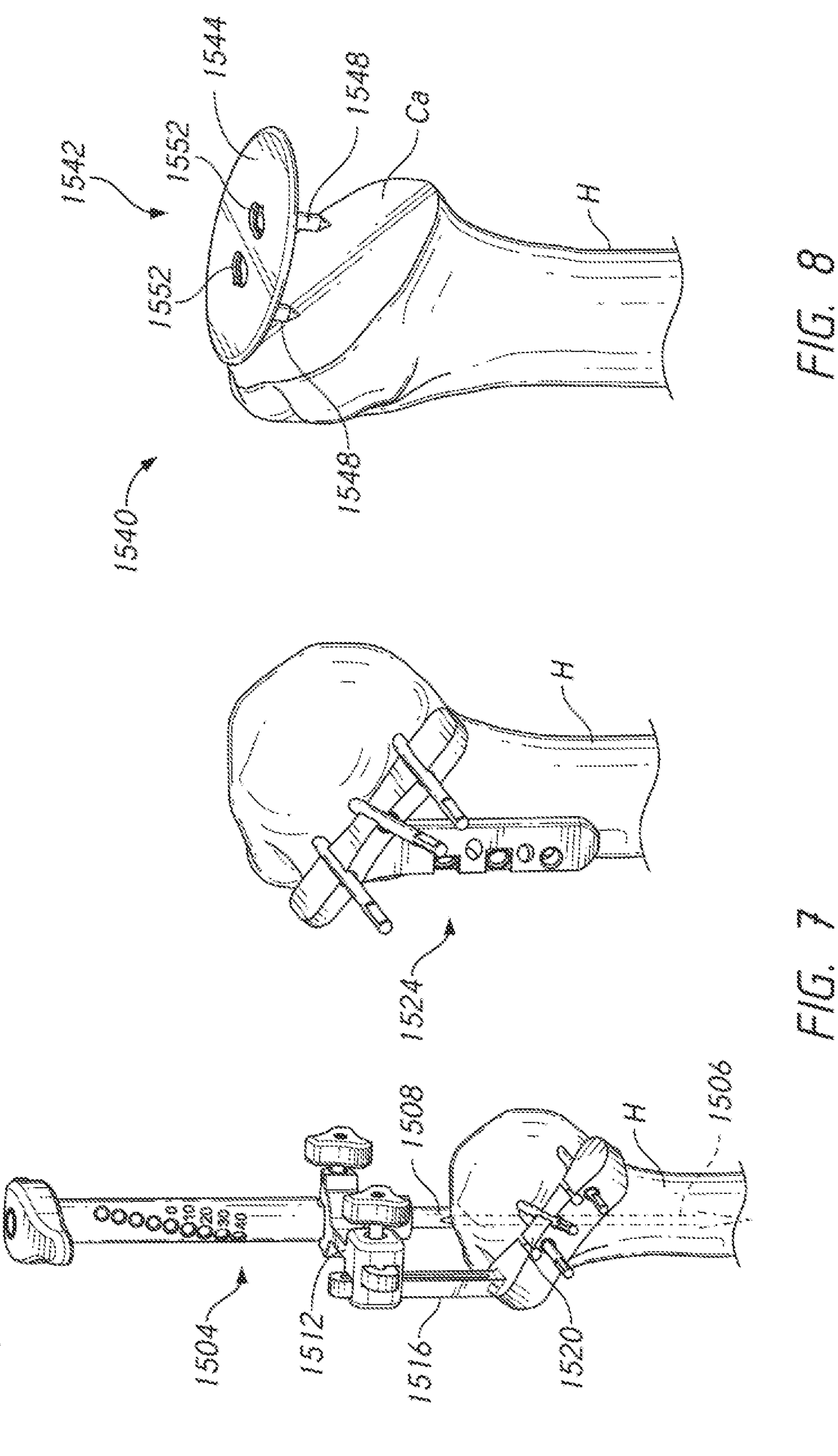
FIG. 7 shows two example methods for resecting a humerus, according to various embodiments.
FIG. 8 illustrates a protection step in which a protection plate is provided over the resected humerus.
Figures 7A, 7B:
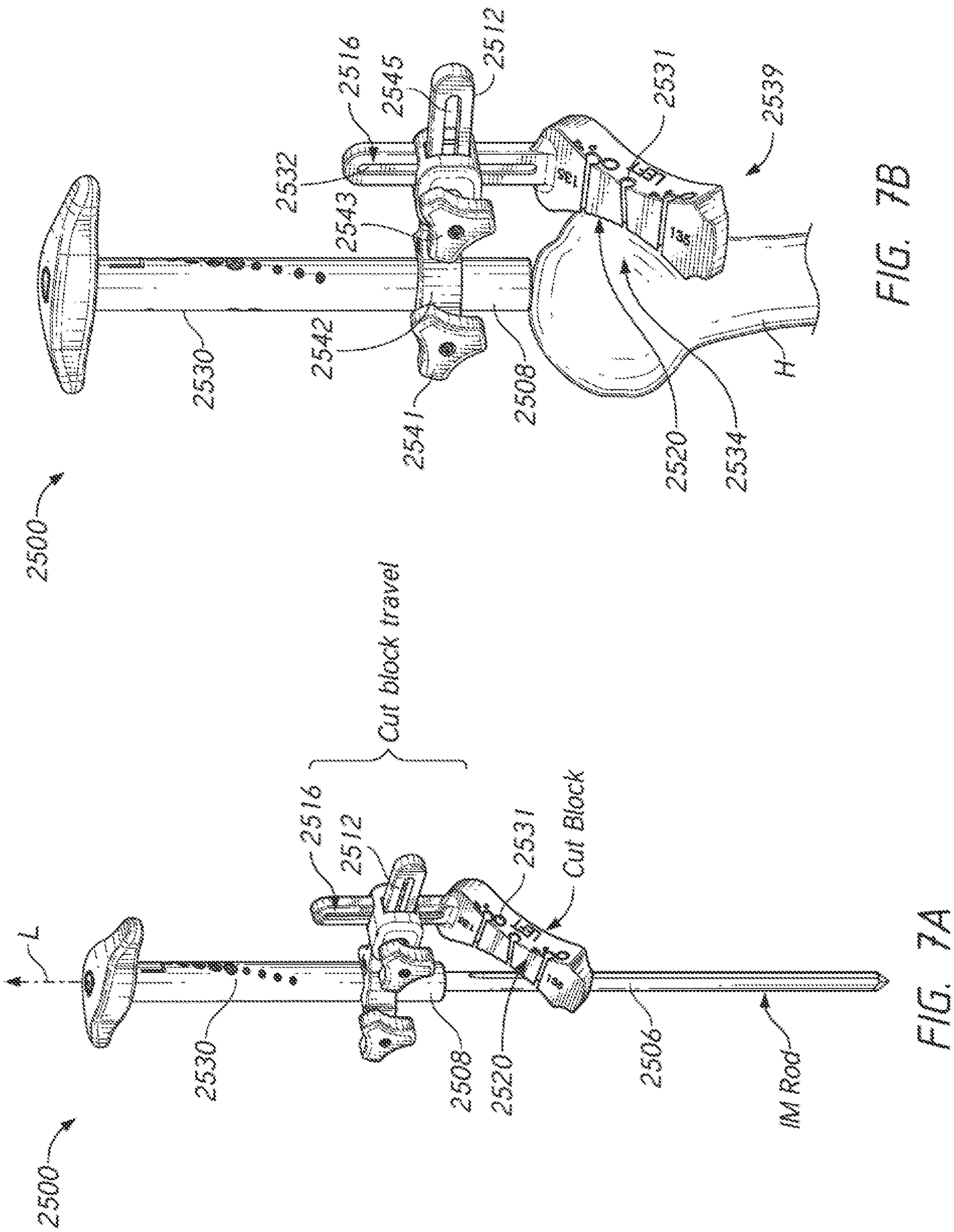
FIGS. 7A-7F illustrate a humeral resection guide and components thereof, according to various embodiments.
Figure 7D:
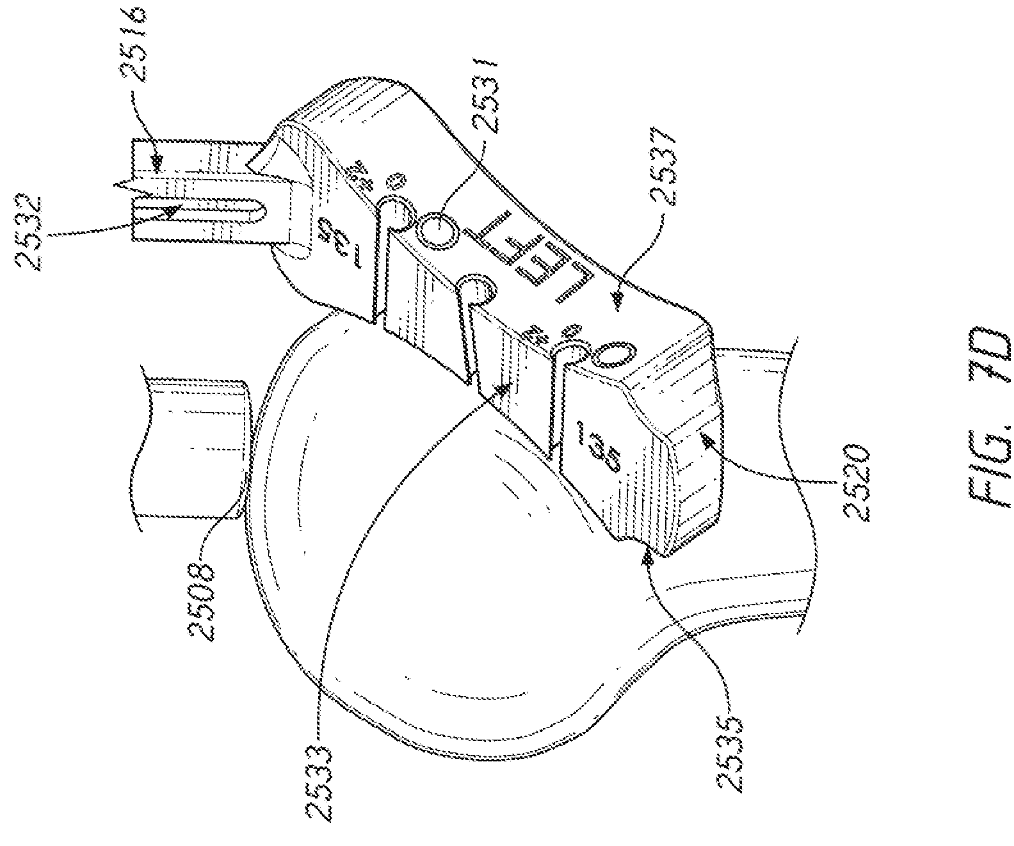

FIGS. 7A-7F illustrate a humeral resection assembly 2500, according to various embodiments. The humeral resection assembly 2500 can be used to resect a humerus bone H of a mammal such as a human. The humeral resection assembly 2500 may be generally similar to the intramedullary cutting block assembly 1504 of FIG. 7, unless otherwise noted. For example, the humeral resection assembly 2500 can comprise an intramedullary rod 2506 configured to be advanced into a proximal end of the humerus, a depth stop 2508 at a proximal end portion of the rod 2506, and a support comprising a handle 2530 extending proximally from the depth stop 2508. As explained above, the intramedullary rod 2506 can comprise a projection that extends distally from the handle 2530, and can be sized and shaped to be inserted into the humerus. As shown in FIG. 7A, the depth stop 2508 can be wider than the intramedullary rod 2506. The depth stop 2508 can be configured to limit the advancement of the intramedullary rod 2506 to a selected extent (see FIG. 7C).

The support can also comprise a cross arm 2512 that can be rotatably connected to the handle 2530 by way of a first connector 2541 and a circumferential band 2542 that extends at least partially (e.g., completely, in some embodiments) around the handle 2530. The first connector 2541 can be adjusted to move the cross arm 2512 vertically along (e.g., superiorly and/or inferiorly) the handle 2530, and/or to rotate the cross arm 2512 about a longitudinal axis L of the handle 2530. For example, the first connector 2541 can comprise a threaded connector that is connected to or integrally formed with the circumferential band 2542. The first connector 2541 can be rotated to loosen and/or tighten the circumferential band 2542 relative to the handle 2530. When the first connector 2541 is sufficiently loose, the clinician can translate the cross arm 2512 vertically along the handle 2530 and/or can rotate the cross arm 2512 about the longitudinal axis L. In various embodiments, the cross arm 2512 can be positioned to extend anteriorly relative to the handle 2530. The cross arm 2512 can also include an opening 2545 and a second connector 2543 extending through the opening 2545. In the illustrated embodiment, the opening 2545 comprises an elongate opening or slot that extends through a thickness of the cross arm 2512. The second connector 2543 can comprise a connector that is the same type as the first connector 2541, e.g., a threaded connector. In other embodiments, the second connector 2543 can be a different type of connector than the first connector 2541.

The humeral resection assembly 2500 can further include a cutting guide component 2539 that includes a cutting block 2520 and a boom 2516 extending at an angle from the cutting block 2520. The cutting block 2520 can have a side surface 2535 configured to face an exterior surface 2534 (such as an anterior exterior surface) of the humerus H. The cutting clock 2520 can include a cutting surface 2533 disposed non-parallel (e.g., approximately perpendicular) relative to the side surface 2535. The cutting surface 2533 can configured to constrain at least one degree of freedom of movement of a cutting instrument during surgical alteration (e.g., resection) of the humerus H. The rod 2506 can extend distal of the cutting block 2520. In addition, one or a plurality of pin holes 2531 can extend through the side surface 2535 to an opposing side surface 2537 of the cutting block 2520. The opposing side face 2537 can be disposed away from the exterior surface 2534 of the humerus H when the side surface 2535 is positioned against and/or adjacent to the exterior surface 2534 of the humerus H, as shown, for example, in FIG. 7D. One or more corresponding pin(s) (not shown) can be provided through the pin hole(s) 2531 and into the humerus H to secure the cutting block 2520 to the humerus H during resection.

The boom 2516 can be integrally formed with or otherwise coupled to the cutting block 2520. As shown in FIGS. 7A, 7B, 7D, and 7F, the boom 2516 can extend away from the cutting surface 2533 of the cutting block 2520. In the illustrated embodiment, the boom 2516 can extend away from the cutting block 2520 at an obtuse angle relative to the cutting surface 2533. The obtuse angle can be in a range of 130° to 150°. In one embodiment, the obtuse angle is approximately 135°. In another embodiment, the obtuse angle is approximately 145°. The boom 2516 can include a cut depth adjustment mechanism comprising a slot 2532 (e.g., an elongate opening or hole) disposed along at least a portion of a length of the boom 2516. The slot 2532 can comprise a blind hole (e.g., recess) or a through hole in various embodiments.

The cross arm 2512 or support can be adjustably connected to the slot 2532 (or cut depth adjustment mechanism) by way of the second connector 2543. The cross arm 2512 can be configured to be positioned along the slot 2532 at a plurality of or over a range of locations along the length of the boom 2516. For example, the second connector 2543 (such as a threaded connector) can extend through the opening 2545 of the cross arm 2512 and the slot 2532 of the boom 2516. The second connector 2543 can be loosened to move the boom 2516 and cutting block 2520 laterally and/or anteriorly along the cross arm 2512, and/or to position the cutting block 2520 inferiorly or superiorly relative to the cross arm 2512. The second connector 2543 can be tightened to secure the boom 2516 to the cross arm 2512 at a desired position relative to the humerus H. As illustrated, the cross arm 2512 can extend anteriorly relative to the handle 2530 between the handle 2530 and the boom 2516 such that the boom 2516 and the cutting block 2520 are spaced anteriorly from the handle 2520 by the cross arm 2512.

Once the cutting block 2520 and boom 2516 are positioned at the desired location along the exterior surface 2534 of the humerus H, the clinician can secure the cutting block 2520 to the humerus H by inserting the pin(s) through the pin hole(s) 2531 and into the humerus H. In some arrangements, the clinician can remove the rod 2506 after the cutting block 2520 is secured to the humerus H. The clinician can utilize the cutting surface 2533 of the cutting block 2520 as a guide along which a resection tool can be supported during resection of the humerus H.

In some procedures, it can be challenging to accurately and quickly position the cutting surface 2533 at the clinically-appropriate cutting location on the exterior surface 2534 of the humerus H. For example, in some procedures, the clinician may have trouble aligning the cutting block 2520 and boom 2516 at the appropriate location along the superior-inferior direction, and/or may not accurately estimate the correct cut depth for resection. The cut block travel length along the slot 2532 of the boom 2516 can be in a range of 20 mm to 60 mm, or approximately 40 mm in some arrangements. It can be challenging for the clinician to select the appropriate cut depth by eye during a resection procedure. Beneficially, the embodiments disclosed herein can provide a target estimated cut depth to enable the clinician to have an initial estimate of the location at which the humerus H should be cut or resected, while providing a stable and accurate platform relative to the neck shaft angle of the cut.

To assist the clinician in accurately positioning the cutting block 2520, the humeral resection assembly 2500 can include a cut depth indicator 2536 comprising one or a plurality of markings disposed at a population derived location along the length of the boom 2516. As explained herein, the population derived location of the cut depth indicator 2536 can be derived at least in part from image data of a plurality of humeruses H. In the illustrated embodiment, the cut depth indicator 2536 comprises a plurality of (for example, two) markings spaced apart along at least a portion of the length of the boom 2516. The cut depth indicator 2536 can be configured to indicate that the cutting surface 2533 is at an initial estimated target cut depth for the surgical alteration (e.g., resection) of the humerus H when the cut depth indicator 2536 is aligned with the support or cross arm 2512. As explained above, the slot 2532 can enable the clinician to slidably position the boom 2516 and cutting block 2520 vertically such that the cutting surface 2533 is at the desired cutting location. In the illustrated embodiments, the slot 2532 can serve as a cut depth adjustment mechanism to position the cutting surface 2533 at the target cut depth.

In various embodiments, a plurality of humerus bones from a human patient population can be used to estimate the initial target cut depth that is a statistical representation or average of a typical human shoulder. For example, in various embodiments, the plurality of humerus bones can be measured (e.g., imaged using X-ray or computed tomography (CT) scans, or physically measured on human humerus bones) to provide a plurality of measurements associated with a plurality of human humerus bones. The measurements can be analyzed to determine an average size of a human humerus H. For example, one or more of the mean, median, or mode of the measurements can be calculated as a representation of the average human humerus H. The measurements and analyses thereof can be used to locate the marking(s) of the target cut depth indicator 2536 along the boom 2516.

Figure 7C:
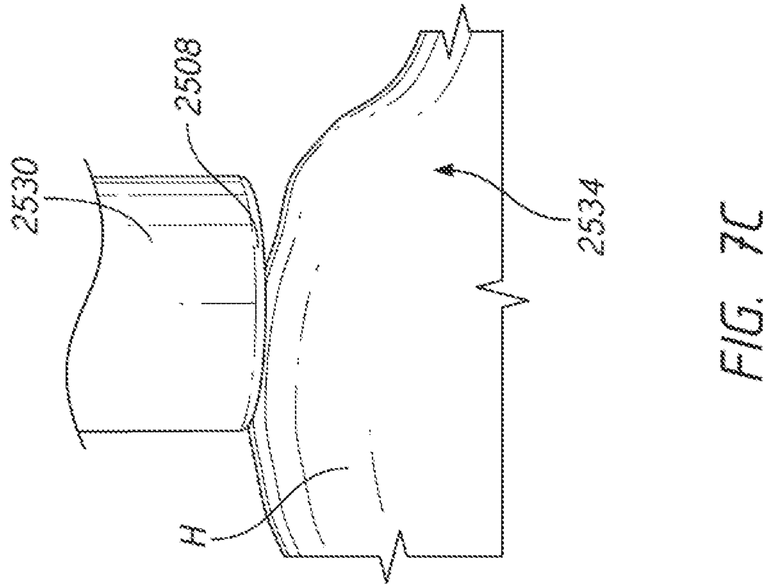
Figures 7E, 7F:
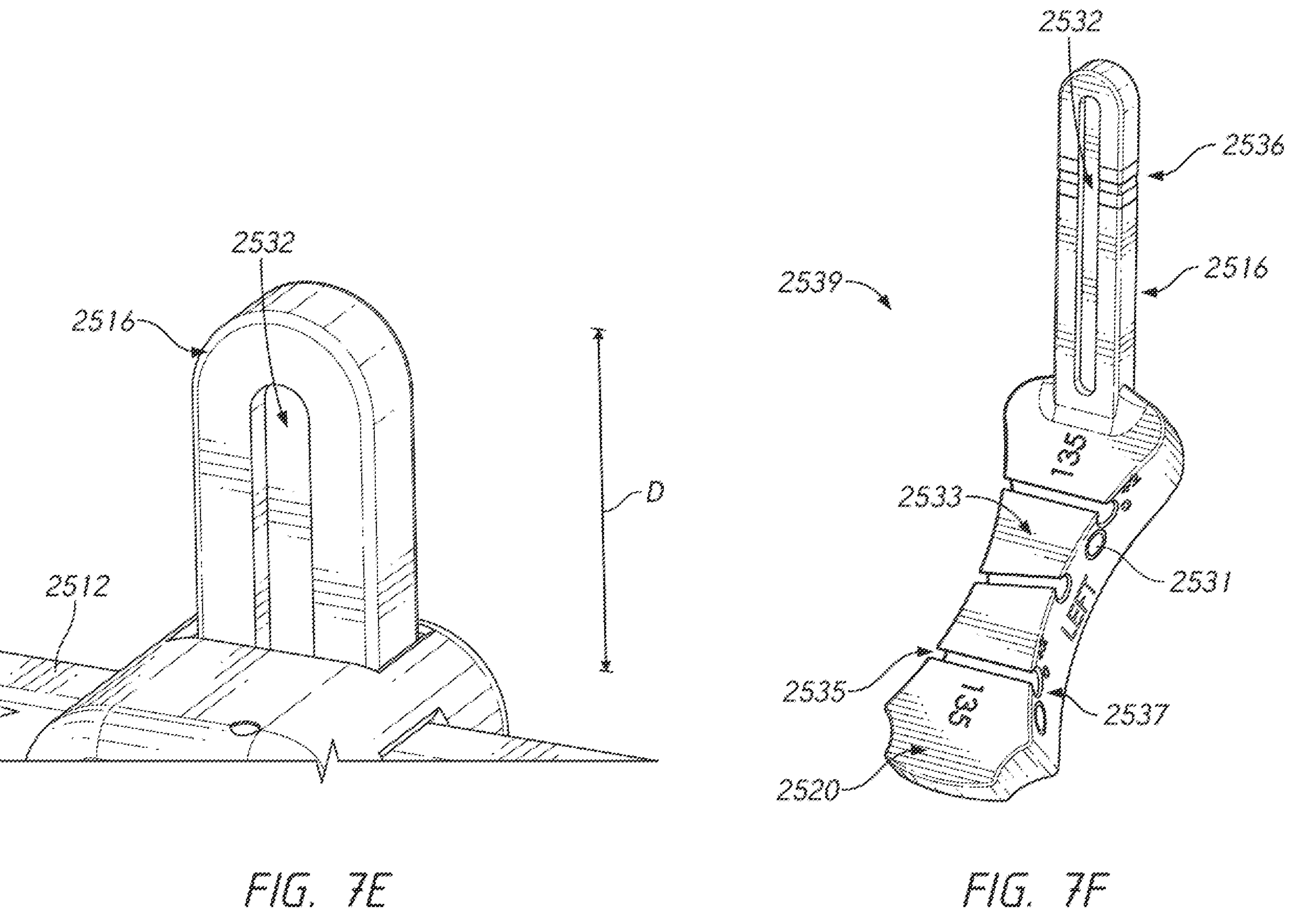
Figure 7G:
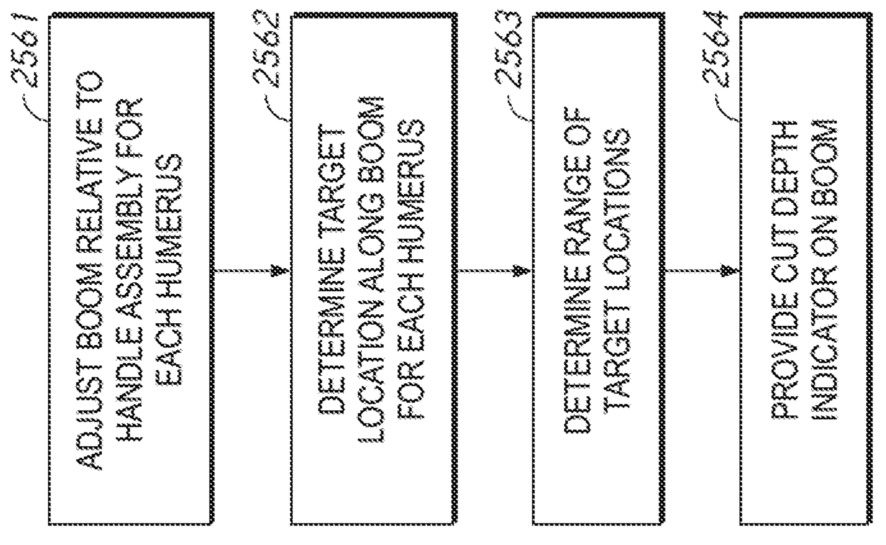
FIG. 7G is a flowchart illustrating a method of manufacturing a humeral resection guide, according to various embodiments.

FIG. 7G is a flowchart illustrating a method 2560 of manufacturing a humeral resection guide 2500, according to various embodiments. As shown in FIG. 7B, the intramedullary rod 2506 can be inserted into the humerus H of each patient of the population of patients aligned with the intramedullary canal. As shown in FIG. 7C, the rod 2506 can be fully seated in the humerus H until the depth stop 2508 contacts the outside cortex of the humerus H. In a block 2561, for each humerus of the plurality of humeruses in the selected population, the boom 2516 can be adjusted (e.g., vertically adjusted) relative to the handle 2530 such that the cutting block 2520 is disposed at a target cut depth for that particular humerus H (see FIG. 7B). The target cut depth can be determined based at least in part on analysis of image data (e.g., X-ray or CT image data) of the plurality of humerus bones. In other embodiments, the target cut depth can be estimated based on measurements of actual humerus bones.

In a block 2562, for each humerus of the plurality of humeruses, a target location along a length of the boom 2516 to which the handle 2530 is connected when the cutting block 2520 is disposed at the target cut depth can be determined. For example, as shown in FIG. 7E, a distance D can be measured from an end of the boom 2516 to the cross arm 2512 of the handle 2530 to determine the target location along the length of the boom 2516.

Based at least in part on the determined target locations for the plurality of humeruses, in a block 2563, a range of target locations along the length of the boom 2516 can be determined. For example, in some embodiments, an average (e.g., a median, mean, or mode) can be calculated based on the plurality of determined target locations to provide the range of target locations. Turning to a block 2564, a cut depth indicator 2536 can be provided on the boom 2516 at a target region of the boom 2516 based at least in part on the determined range of target locations. For example, as explained herein, a plurality of markings can be provided at spaced apart locations along the length of the boom 2516. As shown in FIG. 7F, for example, a pair of parallel lines can be provided on the boom 2516 at the target region to define an initial target location of the cutting block 2520.

Figure 7H:
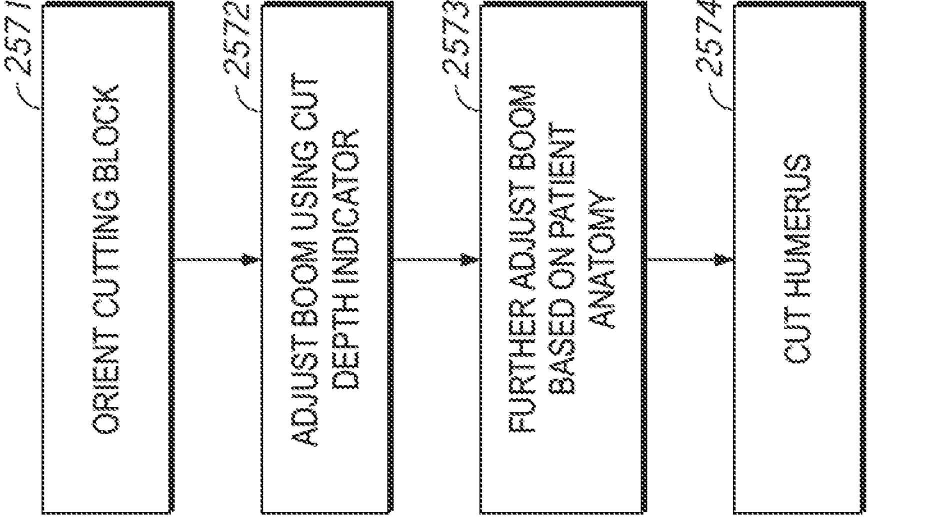
FIG. 7H is a flowchart illustrating a method of surgically altering a humerus using a humeral resection guide, according to various embodiments.

Beneficially, the depth cut indicator 2536 described herein can provide the clinician with an initial estimate of the location at which the cutting surface 2533 of the cutting block 2520 should be placed. FIG. 7H is a flowchart illustrating a method 2570 of surgically altering a humerus H using a humeral resection guide 2500, according to various embodiments. As explained herein, the intramedullary rod 2506 can be inserted into the humerus H of the patient at an orientation aligned with the intramedullary canal and until the depth stop 2508 contacts the outside cortex of the humerus H. In a block 2571, a side surface 2535 of the cutting block 2520 can be oriented to face an exterior surface 2534 of the humerus H.

In a block 2572, the boom 2516 can be adjusted relative to the handle 2530 using a cut depth indicator 2536 on the boom 2516 to position the cutting block 2520 at a target cut depth defined at least in part by the cut depth indicator 2536. The cut depth indicator 2536 can accordingly provide the clinician with an initial estimated location at which to position the boom 2516 and cutting surface 2533. Moving to a block 2573, the boom 2516 can be further adjusted by the clinician based at least in part on the patient's shoulder anatomy. Although the cut depth indicator 2536 can provide an accurate initial estimate of the cut depth, in some situations and for some patients, it may be desirable to further adjust (e.g., translate vertically) the boom 2516 to accommodate variations in the particular patient's humerus H. Thus, the population derived structure of the cut depth indicator 2536 can provide an accurate initial estimate of the cut depth, and the clinician can refine the location based on patient-specific anatomy.

Turning to a block 2574, the humerus H of the patient can be cut (e.g., resected) at the target cut depth. As explained herein, one or more pin(s) can be provided through the pin hole(s) 2531 to secure the cutting block 2520 to the humerus H once the cutting surface 2533 is at the target location. In some embodiments, the rod 2506 can be removed after the cutting block 2520 is secured to the humerus H. In various embodiments, the clinician can place the cutting instrument along the cutting surface 2533, which can act as a guide for the cutting instrument during resection.

FIG. 8 shows that following resection, an optional protect step 1540 can be performed. In the protect step 1540 the resected surface that was formed in the resection step 1500 can be protected while other aspects of the surgery are on-going. It is important to protect the newly exposed cancellous bone Ca because this bone is to be formed in later parts of the method to have a recess having an inner profile that matches the outer or exterior and distal surface of any of the anchors (e.g., the stemless anchor or the metaphysis portion of the stemmed anchors). The protect step 1540 can be performed by applying a protect tool 1542 to the resected surface to cover the cancellous bone Ca. The protect tool 1542 can include a protect plate 1544. The protect plate 1544 can have one or a plurality, e.g., two spikes 1548 extending from a bone facing (distal or medial) side of the protect plate 1544. The spikes 1548 can be sharp enough at their distal end to allow the spikes 1548 to be pressed into the cancellous bone Ca. The protect plate 1544 can include one or a plurality of, e.g., two, handling apertures 1552 disposed therein. The handling apertures 1552 can extend entirely through the protect plate 1544 in one embodiment. The handling apertures 1552 can be gripped by a tool, such as would be similar to the scissors tool sown in FIG. 13. Once the protect step 1540 is complete, other aspects of the method can follow.

Figures 9, 10:
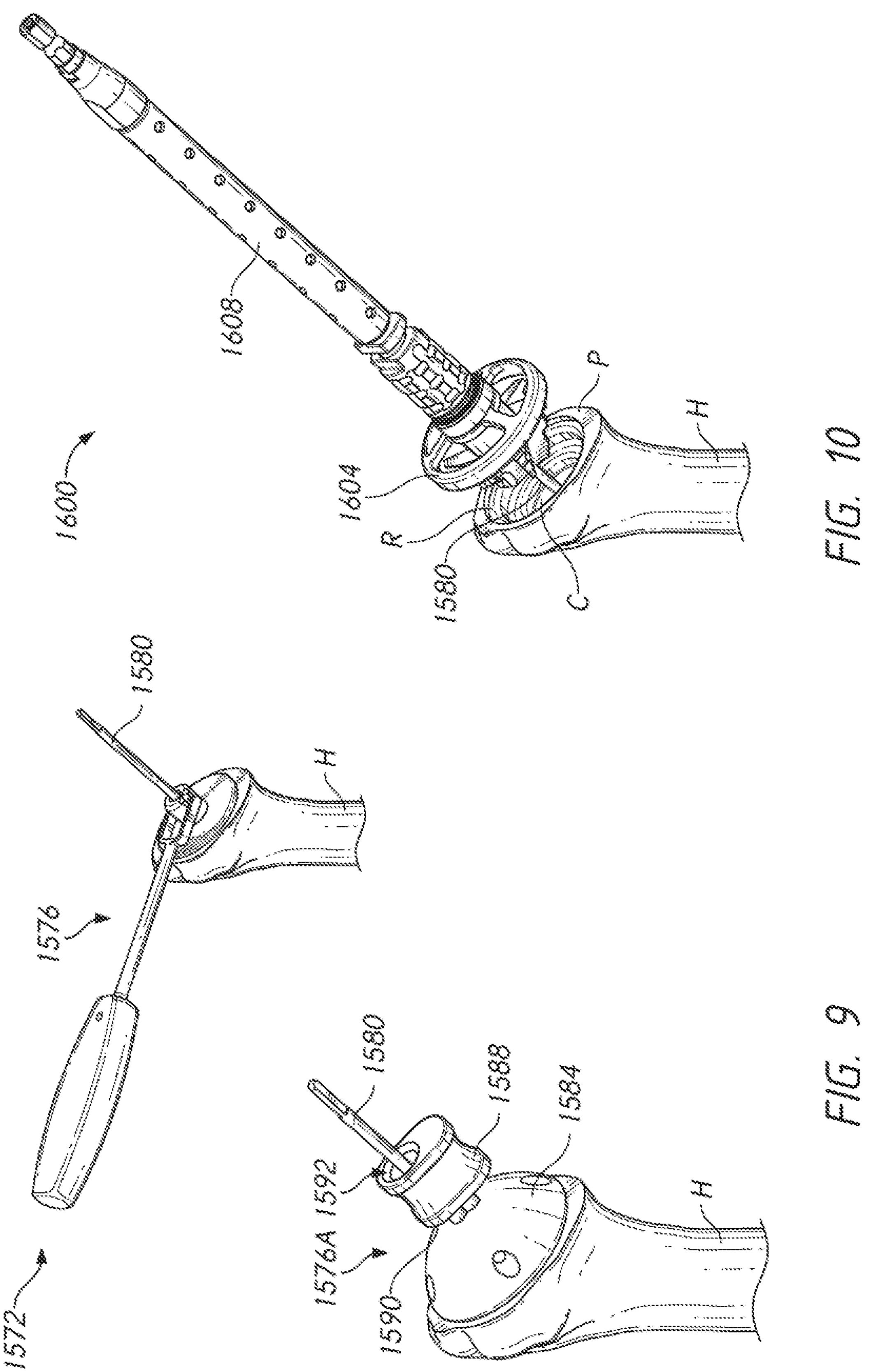
FIG. 9 illustrates a method for sizing a humerus before implanting a humeral anchor, according to various embodiments.
FIG. 10 illustrates an example method of reaming the resected humerus.

FIG. 9 shows a sizing step 1572 that can be subsequently performed. The protect tool 1542 can optionally be removed prior to the sizing step 1572. In the sizing step 1572 a handle and sizer assembly 1576 is placed against the resected humerus at the exposed cancellous bone Ca. The handle and sizer assembly 1576 can enable a determination of which size of the stemless humeral anchor 103 (or other anchor as disclosed or claimed herein) should be used for the particular patient. For example, the handle and sizer assembly 1576 can have a number 1, 2, 3, or 4 on a face thereof that corresponds to four similarly labeled or numbered sizes. The handle and sizer assembly 1576 preferably have an aperture formed therein for placement of a guide pin 1580. The guide pin 1580 can be advanced through the aperture in the handle and sizer assembly 1576 and into the cancellous bone Ca at the resection surface and thereafter sufficiently deep into the humerus H to be stable for subsequent procedures.

FIG. 9, lower image, shows another example of a handle and sizer assembly 1576A. The handle and sizer assembly 1576A includes a head sizer 1584 and a handle 1588. The head sizer 1584 can have the same form as an anatomical articular body, e.g., with a convex surface facing away from the resection and a planar surface facing the resection. The head sizer 1584 provides a very clear visual confirmation of how an anatomic head would sit on the resection surface. The handle 1588 can include a projection 1590 that can be advanced into a keyed opening in the head sizer 1584. The connection between the projection 1590 and the keyed aperture can be a snug fit so that simple hand force can be used to insert the handle 1588 into the head sizer 1584 and also remove the head sizer 1584 from the handle 1588. The snug fit can provide a retention force that is sufficient to prevent the head sizer 1584 from falling off the handle 1588 so that the surgeon can use the handle 1588 to place the head sizer 1584 on the resected surface and remove the head sizer 1584 from that surface without more complex tools like graspers. The handle 1588 can have a concave side periphery that can be shaped to at least partially receive the convex curvature of the surgeon's fingers making the handle 1588 comfortable and easy to grip. The handle 1588 can have a pin aperture 1592 formed therethrough. The pin aperture 1592 can have a length from a proximal side of the handle 1588 to a distal side thereof through the projection 1590. The length can be sufficient to accurately guide the guide pin 1580 into the humerus H through the cancellous bone Ca exposed at the resection.

After the pin has been placed the handle and sizer assembly 1576, 1576A can be removed over the proximal end of pin leaving the pin in place.

FIG. 10 shows a reaming step 1600 that can follow the resection step 1500. The reaming step 1600 optionally is performed over the guide pin 1580 so it can also follow the sizing step 1572 or another step in which a pin is placed in some examples After the reamer is advanced toward the bone, the reaming step 1600 can be used to form a recess or cavity C in the cancellous bone Ca of the humerus H that is exposed by the resection step 1500. The reaming step 1600 can produce a stepped internal recess or cavity C in the metaphysis of the humerus H shaped to receive a humeral anchor portion, e.g., the stemless anchor 103 or a metaphysis portion of a stemmed anchor. The cavity C may include a first or proximal cavity portion and a second or distal cavity portion extending to a greater depth into the bone than the first cavity portion. The distal portion of the cavity may have a reduced diameter compared to the proximal portion. The cavity C may also include a stepped portion between the first portion and the second portion of the cavity. The recess can be rotationally symmetric in some examples, such that a reamer assembly including a reaming head 1604 and a driver shaft 1608 can be used to form the recess. The reaming head 1604 may also form a recessed surface R below the resection plane P of the bone. The recessed surface may be proximal of and at least partially surround the cavity C. The recessed surface R and the cavity C may be formed simultaneously (e.g., using reaming head 1800) or formed sequentially (e.g., using reaming heads 1850A, B). The reaming head 1604 can be configured to be removably attached to the driver shaft 1608 to enable selection of one of a plurality of size of reaming head 1604 to be used with a common driver shaft 1608. The size of the reaming head 1604 corresponds to the size determined in the sizing step 1572 in some examples. One or both of the reaming head 1604 and the driver shaft 1608 are cannulated to enable the direction of reaming to be controlled by the orientation of the guide pin 1580.

Figures 10A, 10B:
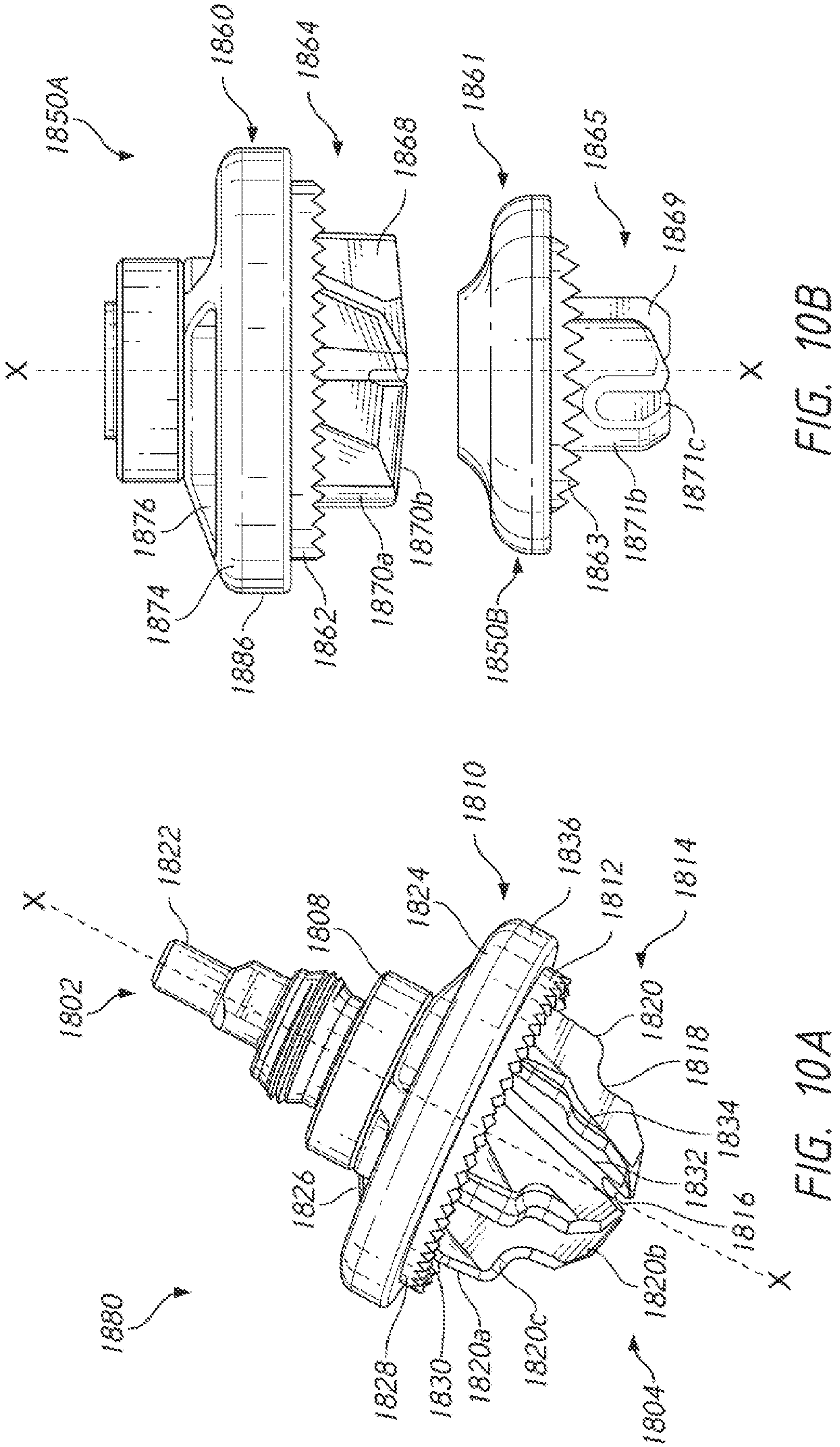
FIGS. 10A-10B illustrate examples of reamers configured to form a space suitable for a stem or stemless humeral anchor.

FIGS. 10A-10B illustrate example reaming heads that may be used in the reaming step 1600.

FIG. 10A illustrates a reaming head 1800 having a first or proximal end 1802 and a second or distal end 1804. The reaming head 1800 includes a drive shaft 1822 at the first end 1802. The drive shaft 1822 is configured to be removably attached to the driving mechanism. The driving mechanism is configured to rotate the reamer head 1800 about a drive shaft axis X to remove bone. The reaming head 1800 may also include an indicator 1808 positioned near the first end 1802. The indicator 1808 may provide an indication of size. Different sized reamers may correspond to different sized anchor. The indicator may be a color indicator, numeral indicator, or other indicator.

The reamer head 1800 includes a proximal portion 1810 and a distal portion 1814. The proximal portion 1810 includes a proximal face 1824 of the reaming head 1800. The proximal face 1824 includes one or more apertures 1826 extending therethrough and visible by the surgeon during the procedure so the surgeon may visualize the bone region being reamed. The apertures 1826 enable bone material to be evacuated from the reamer during reaming. The apertures 1826 may also reduce the total weight of the reaming head 1800. The proximal portion 1810 may include a depth stop 1836 configured to control an insertion depth of the reamer head 1800.

The proximal portion 1810 includes a distal facing cutting edge 1812. The distal facing cutting edge 1812 include a plurality of teeth extending circumferentially around the proximal portion 1810 of the reaming head 1800. The distal facing cutting edge 1812 is configured to form a recessed surface R with respect to the resection plane P (see FIG. 10). The depth stop 1836 may project radially outward of the distal facing cutting edge 1812 such that the depth stop may be seated on the resection plane P when the distal facing cutting edge 1812 forms the recessed surface R.

The distal facing cutting edge 1812 defines an inner periphery 1830 and an outer periphery 1828. A thickness of the recessed surface R corresponds to a thickness of the distal facing cutting edge 1812 measured between the inner periphery 1820 and the outer periphery 1828. The distal facing cutting edge 1812 does not remove any material interior to the inner periphery 1820. When the anchor is implanted, the proximal end of the anchor (e.g., proximal end 239 of anchor 203) is configured to be seated on the recessed surface R formed by the distal facing cutting edge 1812.

The distal portion 1814 of the reaming head 1800 extends distally from the proximal portion 1810 of the reaming head 1800. The entire distal portion 1814 may be within the inner periphery 1820 of the proximal portion 1800. The distal portion 1814 forms the cavity C extending distally from the recessed surface R (see FIG. 10). The cavity C is also positioned radially inward of the recessed surface R.

As shown in FIG. 10A, the distal portion 1814 includes a plurality of radial arms 1818 extending radially outward from a central region of the reaming head 1800. The plurality of radial arms 1818 may be circumferentially spaced apart from each other. Each radial arm 1818 is defined by a first flat face 1832 and a second flat face 1834 opposite the first flat face 1832. The first flat face 1832 and the second flat face 1834 are separated by a thickness. A width of each of the flat faces 1832, 1834, measured in a radial direction, is greater than the thickness of each arm 1818. The thickness of each radial arm 1818 forms a lateral cutting edge 1820. The lateral cutting edge 1820 has a different profile than the distal cutting edge 1812. For example, the distal cutting edge 1812 may include a plurality of teeth or a serrated edge, while lateral cutting edge 1820 forms a blade edge.

The distal portion 1814 may be configured to form the two-stage cavity C. As explained above, the cavity C may include a proximal portion and a distal portion extending at a greater depth than the proximal portion. The two-stage cavity C is formed by the shape of the lateral cutting edges 1820. Each lateral cutting edge 1820 includes a proximal section defined by a first cutting edge 1820*a*. The first cutting edge 1820*a* may be parallel to or angled with respect to the drive shaft axis X. The first cutting edge 1820*a* forms the proximal portion of the cavity C.

The lateral cutting edge 1820 includes a distal section defined by a second cutting edge 1820*b*. The second cutting edge 1820*b* terminates at a sharped end at the second end 1804 of the reamer head 1800. The second cutting edge 1820*b* is positioned radially inward of the first cutting edge 1820*a*. The second cutting edge 1820*b* may be parallel to or angled with respect to the drive shaft X. The second cutting edge 1820 may be parallel to or angled with respect to the first cutting edge 1820*a*. The second cutting edge 1820*b* forms the distal portion of the cavity C.

The first cutting edge 1820*a* may be separated from the second cutting edge 1820*b* by a stepped portion 1820*c*. The stepped portion 1820*c* projects inward from the first cutting edge 1820*a* and toward the second cutting edge 1820*b*. The transition between the first cutting edge 1820*a* and the stepped portion 1820*c* may form a rounded corner or a sharp corner. The transition between the stepped portion 1820*c* and the second cutting edge 1820*b* may form a rounded corner or a sharp corner. The stepped portion 1820*c* may form an annular ledge between the proximal portion of the cavity and the distal portion of the cavity.

The reaming head 1800 may include a guide channel 1816 configured to receive a guide pin. The guide channel 1816 extends through the second end 1804 of the reaming head and is centrally located with respect to the radial arms 1818.

FIG. 10B illustrates another reaming head system configured to form the cavity C shown in FIG. 10 but in a two-part form. The reaming head system includes a first reaming head 1850A and a second reaming head 1850B. The first reaming head 1850A and the second head reaming head 1850B may include any of the features of the reaming head 1800. Each of the first reaming head 1850A and the second reaming head 1850B is configured to be removably attached to the drive mechanism. The drive mechanism is configured to rotate the reaming heads 1850A, 1850B about the drive shaft axis X to remove bone. Each reaming head 1850A, 1850B may be driven about a guide pin to enable the direction of reaming to be controlled by the orientation of the guide pin.

The first reaming head 1850A is configured to form the recessed surface R and the proximal portion of cavity C (see FIG. 10). As shown in FIG. 10B, the first reaming head 1850A includes a proximal portion 1860 and a distal portion 1864. In use, the first reaming head 1850A may be used first to form the recessed surface R and the proximal portion of the cavity C. Thereafter, the second reaming head 1850B may be used to form distal portion of the cavity C and the stepped portion between the proximal portion and the distal portion of the cavity C.

The proximal portion 1860 includes a proximal face 1874. The proximal face 1874 may include one or more apertures 1876 extending therethrough and visible by the surgeon during the procedure. The proximal portion 1860 may include a depth stop 1886 configured to control an insertion depth of the reamer head 1850A. The proximal portion 1860 also includes a distal facing cutting edge 1862 configured form the recessed surface R with respect to the resection plane P (see FIG. 10). The distal facing cutting edge 1862 may have a similar profile to the distal facing cutting edge 1812.

The distal portion 1864 of the first reaming head 1850A may be configured to form the proximal portion of the cavity C. The distal portion 1864 extends distally from the proximal portion 1860. The entire distal portion 1864 may be within the inner periphery of the proximal portion 1860. As shown in FIG. 10B, the distal portion 1864 includes a plurality of radial arms 1868 extending radially outward from a central region of the reaming head 1850A. The plurality of radial arms 1868 may be circumferentially spaced apart from each other. Each radial arm 1868 forms a lateral cutting edge 1870*a*. The lateral cutting edge 1870*a* may be parallel to or angled with respect to the drive shaft axis X. Each radial arm 1868 may also include a distal edge 1870*b* extending radially inward from the lateral cutting edge 1870*a*. The distal edge 1870*b* may be planar or angled with respect to a transverse axis perpendicular to the drive shaft axis X.

The second reaming head 1850B includes a proximal portion 1861 and a distal portion 1865. The proximal portion 1861 includes a distal facing cutting edge 1863. The distal facing cutting edge 1863 includes a plurality of teeth configured to form an annular ledge between the proximal portion of the cavity C and the distal portion of the cavity C (see FIG. 10A). The distal facing cutting edge 1863 includes an inner periphery and an outer periphery. A diameter of the outer periphery of the distal facing cutting edge 1863 may be no greater than a diameter of the distal portion 1864 of the reaming head 1850A.

The distal portion 1865 may be configured to form the distal portion of the cavity C. The distal portion 1865 extends distally from the proximal portion 1861. The entire distal portion 1865 may be within the inner periphery of the proximal portion 1861. The distal portion 1865 of the second reaming head 1850B may have a reduced diameter compared to the distal portion 1864 of the first reaming head 1850A. As shown in FIG. 10B, the distal portion 1865 includes a plurality of radial arms 1869 extending radially outward from a central region of the reaming head 1850B. The plurality of radial arms 1869 may be circumferentially spaced apart from each other. Each radial arm 1869 forms a first lateral cutting edge 1871*b*, which may be parallel to or angled with respect to the drive shaft axis X. Each radial arm 1869 may also include a distal edge 1871*c* extending radially inward from the laterally cutting edge 1871*b*. The distal edge 1871*c* may be planar or angled with respect to a transverse axis perpendicular to the drive shaft axis X.

Figures 11, 12:
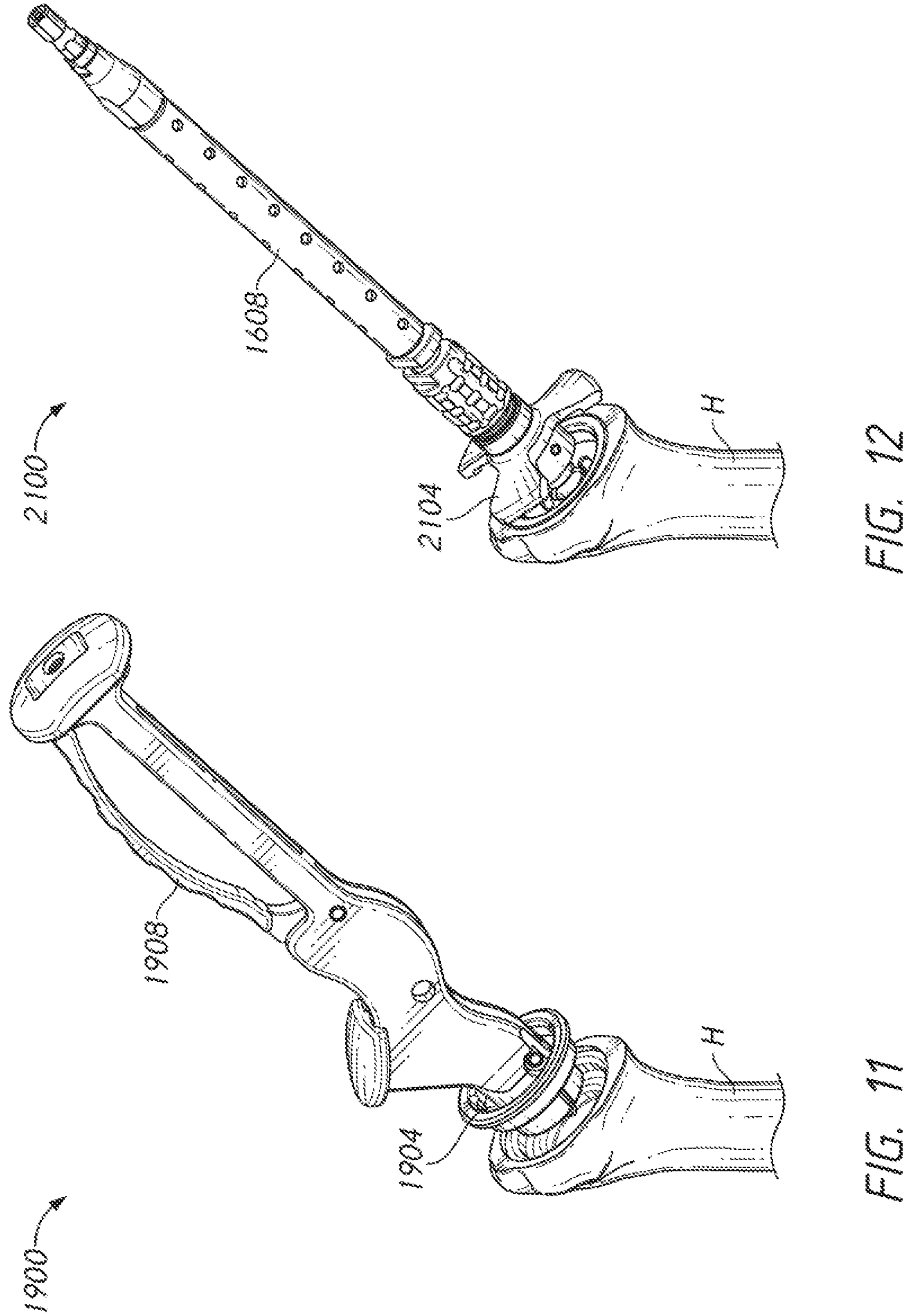
FIG. 11 illustrates an example method of blazing a reamed humerus.
FIG. 12 illustrates an example method of planing the humerus.

FIG. 11 shows an optional blazing step 1900. The blazing step 1900 can follow the reaming step 1600 in order to more precisely form the recess formed in the reaming step 1600. For example, it is desired that the humeral anchors disclosed herein (e.g., the stemless anchor 103 or humeral stem 1200) be placed in a controlled manner such that a collar or annular member (e.g., the bone compression surface 1250) sits flush on a prepared portion of the cancellous bone at or below the resection surface, and such that fin(s) (e.g., fins 309) can be easily implanted into the humerus. If the shape of the recess is only somewhat close to that of the outer surface of the anchor, and/or if the shape of the recess does not accommodate the outer surface of the fins, the anchor may not sit flush on the humerus. Moreover, without a pathway along which to insert the fin(s), it can be challenging to securely implant the fins(s) into the humerus. The blazing step 1900 uses a blazer 1904 and a stem impactor-inserter 1908 to compress the cancellous bone exposed in the reaming step 1600 so that the shape of the wall around the recess in the humerus H matches the shape of the anchor exterior wall in the metaphysis portion thereof. Moreover, the blazer 1904 can form pathways or channels into which the fin(s) can be inserted. The blazer 1904 can also serve as a body into which a trial anchor is placed.

The blazer 1904 can be very similar to the anchor that it is intended to prepare the recess in the humerus H to receive. It can have the same exterior surface of the anchor, for example. The blazer 1904 also can have the same tooling interface so that the stem impactor-inserter 1908 can be used for the blazing step 1900 and for impacting the anchor into the humerus H, as discussed below in connection with FIG. 14. The stem impactor-inserter 1908 is described in greater detail below, but in general the stem impactor-inserter 1908 can have one or a plurality of impaction heads. When provided with a plurality of impaction heads, the stem impactor-inserter 1908 can allow a single tool to be used for the blazing step 1900 regardless of whether the surgeon prefers a stemless or a stemmed implant. Reduction in the number of tools to be provided to the surgeon creates efficiencies and economies as well as reducing waste and cost in the provision of this health-care service, as described in greater detail below.

Following the blazing step 1900, a planing step 2100 can optionally be performed. The planing step 2100 can improve the shape of the remaining resection surface formed in the resection step 1500, e.g., the portion of the resection between the anchor recess and the cortical bone forming the outer wall of the humerus H at the resection. The planing step 2100 can remove any high points on the resection surface that might interfere with the placement of the articular body in the humeral anchor, as discussed below. The planing step 2100 incorporates a planer 2104. The planer 2104 is configured to mate with the blazer 1904 and to be mounted to the driver shaft 1608. Outwardly extending arms with distally extending teeth can be rotated about the blazer 1904 at the level of or just below the level of the resection formed in the resection step 1500. Such rotation can bring the remaining periphery of the resection into a more planar form without high points that could obstruct the connection of an articular body to the anchor.

Figures 13, 14:
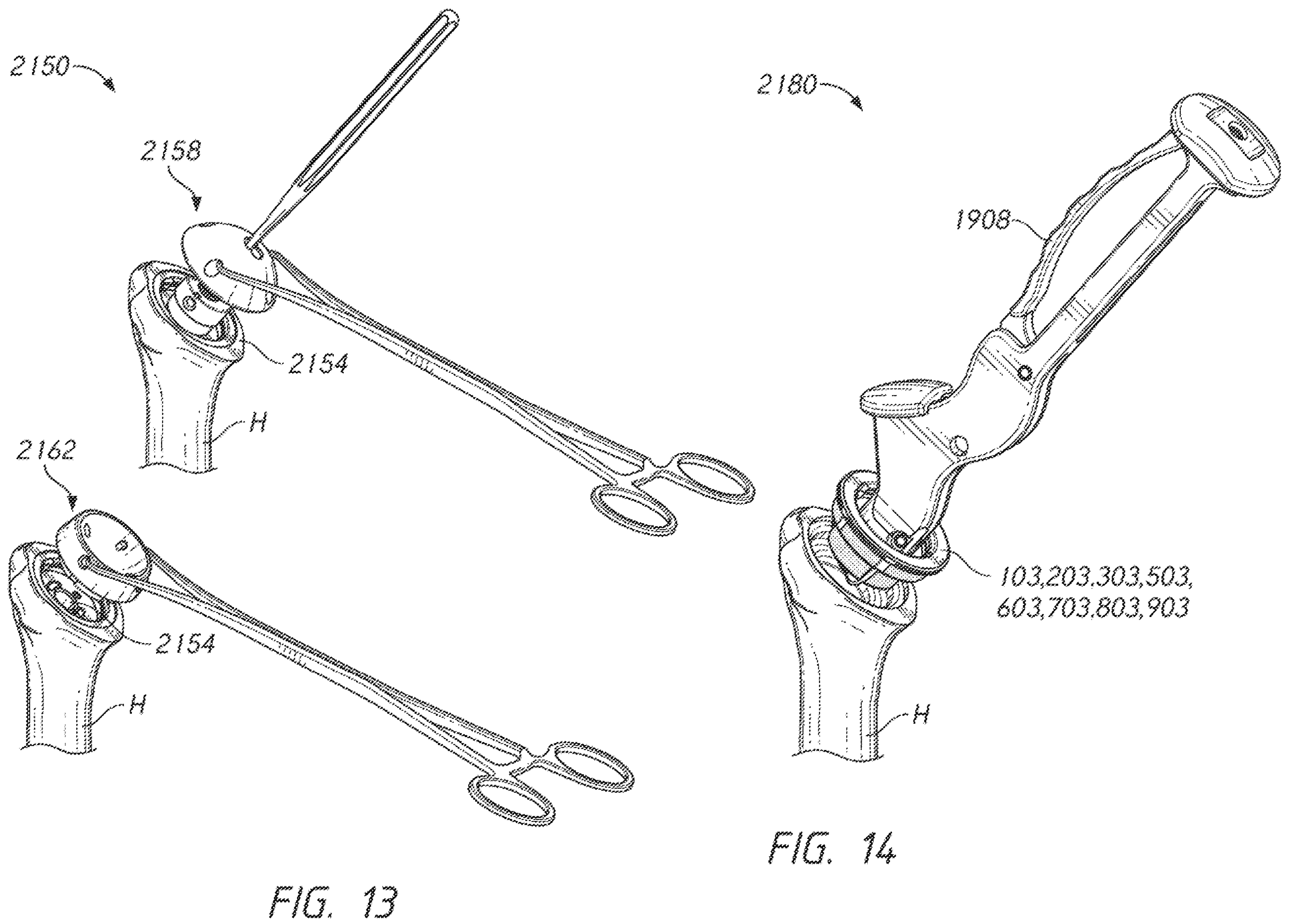
FIG. 13 illustrates an example method in which a reverse trial implant or an anatomic trial implant is inserted into the humerus.
FIG. 14 illustrates an example method in which a stemless humeral implant is implanted into the humerus.

FIG. 13 shows that after the humerus H has been prepared, the method can continue with a trial step 2150. The trial step 2150 can employ a trial anchor 2154 which can be placed using the stem impactor-inserter 1908, as discussed above. The trial anchor 2154 can have more easily disengaged connections with a trial head assembly 2158 (for an anatomical reconstruction) or a trial insert assembly 2162 (for a reverse construction) than would be the case in a final implant. The trial step 2150 can enable a surgeon to choose or confirm a size to be used in the final implant. To the extent an implant can be adjusted by an eccentric coupler or connection feature, the trial step 2150 can allow the surgeon to find the proper level of eccentricity. An eccentric coupler 168 can be used to center the center of rotation of the resection or to provide an eccentric position therefrom. The level of eccentricity can be noted with reference to indicia formed on a proximal surface of the anchor (whether the humeral stem 1200 or the stemless anchor 103, 203, 303, 503). Once the final implant size, configuration, and/or orientation have been confirmed the method can proceed to the implantation of the final implant.

FIG. 14 shows the stem impactor-inserter 1908 coupled with the stemless anchor 103. As noted in the figure the stem impactor-inserter 1908 can be coupled with any of the other stemless anchors 203, 303, 503. Further the stem impactor-inserter 1908 can be coupled with the humeral stem 1200 as indicated by the surgeon. For example, the use of the common instrumentation enables the surgeon to determine during the procedure that the stemless anchor 103 is not appropriate and then to quickly switch to the humeral stem 1200 following any additional preparation of the humerus H that would make the humerus ready for the humeral stem 1200.

In the case of the stemless anchor 103, the stem impactor-inserter 1908 can grip the anchor in the recess thereof by engaging the tooling interfaces, e.g., the blind holes 245. Thereafter, the anchor 103 can be moved into the recess formed in the humerus H and pressed against the prepared surface. Thereafter, an impactor, e.g., a mallet, can be used to apply a load to the impaction head at the proximal end of the stem impactor-inserter 1908 and along the longitudinal axis thereof. The load can thus be directed transverse to, e.g., generally perpendicular to the plane of the resection surface that is formed in the resection step 1500.

In the case of the humeral stem 1200, the stem impactor-inserter 1908 can grip the anchor in the recess thereof by engaging the tooling interface 1213, which can comprise these same configuration blind holes as are found in the stemless anchor 103. The distal end 1218 of the humeral stem 1200 can be inserted through the formed recess in the resection surface and further inserted into the intramedullary canal. Once the diaphysis portion 1204 is in the diaphysis of the humerus H and the metaphysis portion 1202 is in the metaphysis of the humerus, an impaction load can be applied to the stem impactor-inserter 1908. In particular, an impactor, e.g., a mallet, can strike the impaction head that is disposed adjacent to the distal end of the stem impactor-inserter 1908 driving the humeral stem 1200 into firm engagement with the humerus H generally along the axis of the diaphysis portion 1204 of the humeral stem 1200.

Thus the inserting step 2180 can be achieved for a stemless implant such as the anchor 103 and for a stemmed implant such as the humeral stem 1200 using a same impactor instrument, e.g., the stem impactor-inserter 1908.

Figures 15, 16:
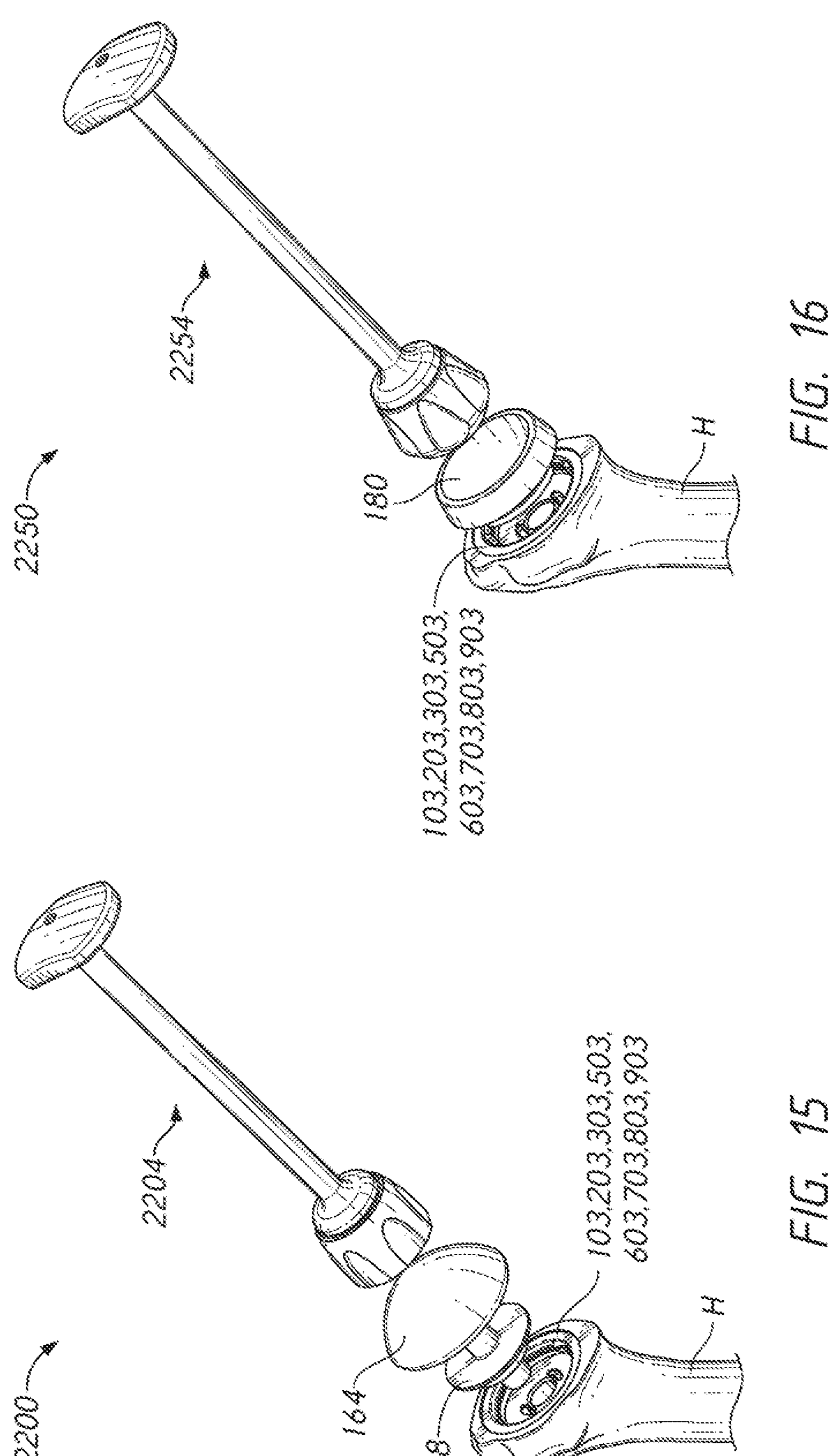
FIG. 15 illustrates an example method in which an anatomical articular component is impacted onto the stemless humeral implant.
FIG. 16 illustrates an example method in which a reverse articular component is impacted onto the stemless humeral implant.

FIG. 15 shows an impacting step 2200 that follows the inserting step 2180. The impacting step 2200 involves impacting an anatomic assembly into the stemless anchor 103 (or another stemless anchor 203, 303, 503). As discussed above, the kit 100 includes shared implant components. As such, the impacting step 2200 can be the same for the humeral stem 1200 as for the stemless anchors 103. The impacting step 2200 can involve placing the coupler 168 adjacent to the anchor 103. The coupler 168 can be a centered coupler or an eccentric coupler. An eccentric coupler can have a feature that provides a visual cue as to rotational position of the coupler 168 relative to the anchor 103. To the extent the trial step 2150 indicated a preferred eccentric rotational position the same position can be re-created in the impacting step 2200. In particular, the visual cues can be used to rotationally position the coupler 168 and determined in the trial step 2150. The anatomic articular body 164 can then be placed on the coupler 168 and the anatomic articular body 164 and the coupler 168 can be impacted together onto the anchor 103. The same steps can be performed with the humeral stem 1200, aligning the coupler 168 with indicial on a proximal face of the humeral stem 1200. An impacting load can be applied by a mallet or other tool to the head impactor 2204.

FIG. 16 shows an impacting step 2250 that is similar to the impacting step 2200 except the impacting step 2250 is being used for a reverse articular body 180. The reverse articular body 180 can be aligned with the stemless anchor 103 (or in a modified example with the humeral stem 1200). In some cases, the reverse articular body 180 can be asymmetric such that rotating the reverse articular body 180 can result in a change in the location of the center of the articular surface of the reverse articular body 180. If the trial step 2150 indicated that a specific rotational position is desired for the reverse articular body 180, then the surgeon will rotate the reverse articular body 180 to that position before applying an impaction load to the reverse insert impactor 2254. The reverse insert impactor 2254 can be identical to the head impactor 2204 other than a distal surface of the reverse insert impactor 2254 has a convex shape and the distal end of the head impactor 2204 has a concave shape.

Figures 17, 18:
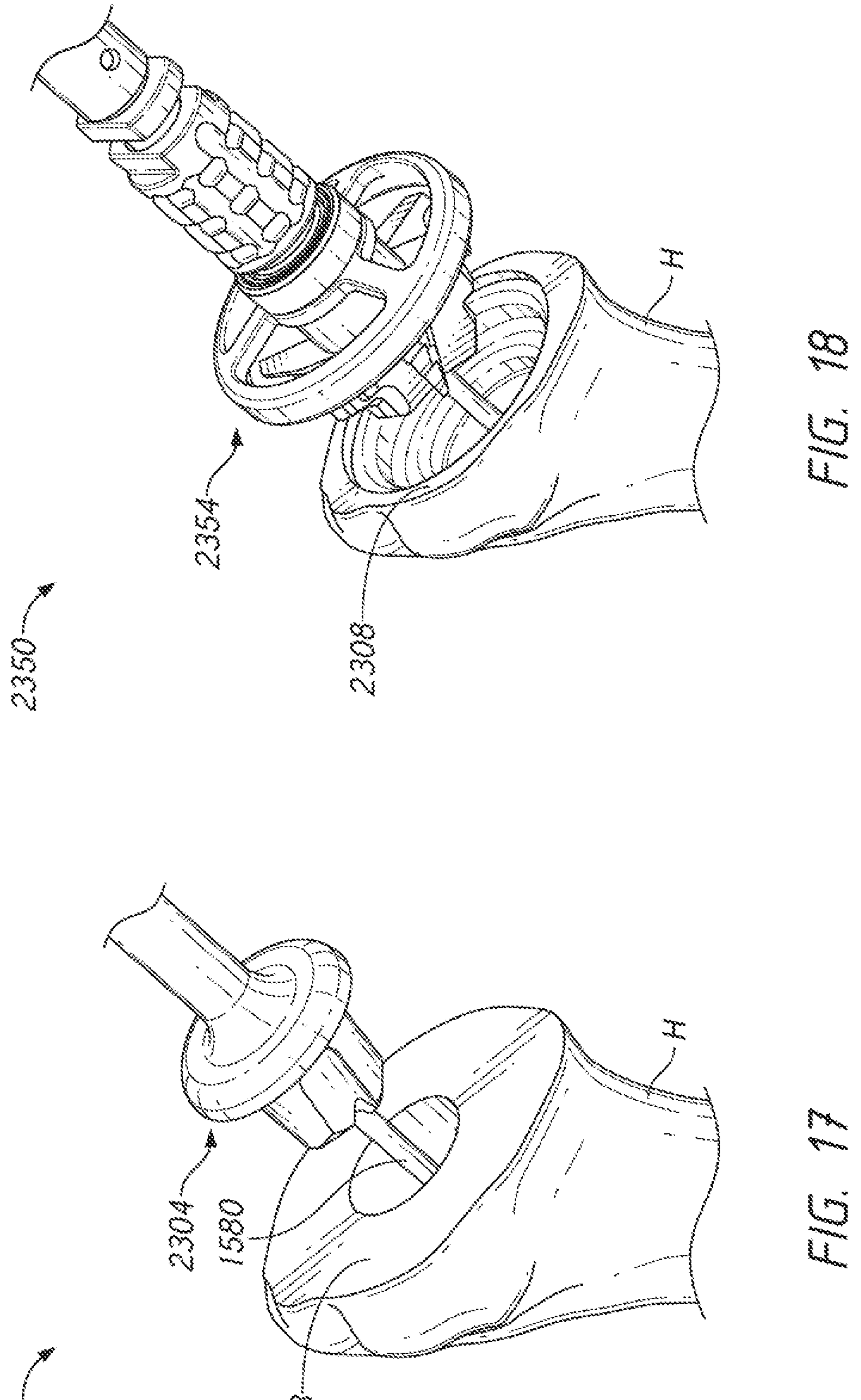
FIG. 17 illustrates an example method in which the humerus is drilled prior to reaming to facilitate preparation of a humerus of a patient with relatively hard bone.
FIG. 18 illustrates an example method in which the humerus undergoes a progressive reaming technique, expanding a recess in hard bone.

Although a typical patient can benefit from the methods described in connection with FIGS. 7-16, FIGS. 17-20 illustrate techniques for other patients. FIGS. 17-18 show one approach to a patient with harder than normal bone matter. The method can follow the resection step 1500 and sizing step 1572 with a drilling step 2300. The drilling step 2300 can benefit from the placement of the guide pin 1580. A drill head 2304 can be advanced over the guide pin 1580. The drill head 2304 can have a smaller and more rigid profile than the reaming head 1604. The drill head 2304 can form a starter hole 2308 in the cancellous bone distal of the resection formed in the resection step 1500. The starter hole 2308 can be centered on the guide pin 1580 and can have a volume that is less than the final volume to be prepared, e.g., about 10-25 percent of the volume to be ultimately prepared. Following the preparation of the starter hole 2308, a larger hole closer to the final size can be formed in a progressive reaming step 2350. The progressive reaming step 2350 can employ an initial reamer 2354 that has a reaming head that is smaller than the reaming head 1604. The initial reamer 2354 can be more rigid than the reaming head 1604 due to its smaller size. Also, the resistance of the bone can be less if the initial reamer 2354 is tasked with removing less bone volume than the reaming head 1604. The progressive reaming step 2350 can employ multiple intermediate reamers that are sized between the size of the initial reamer 2354 and the reaming head 1604 to gradually increase the size of the recess distal to the resection until the recess is properly sized for the steps following the reaming step 1600 in the process flow above.

Figures 19, 20:
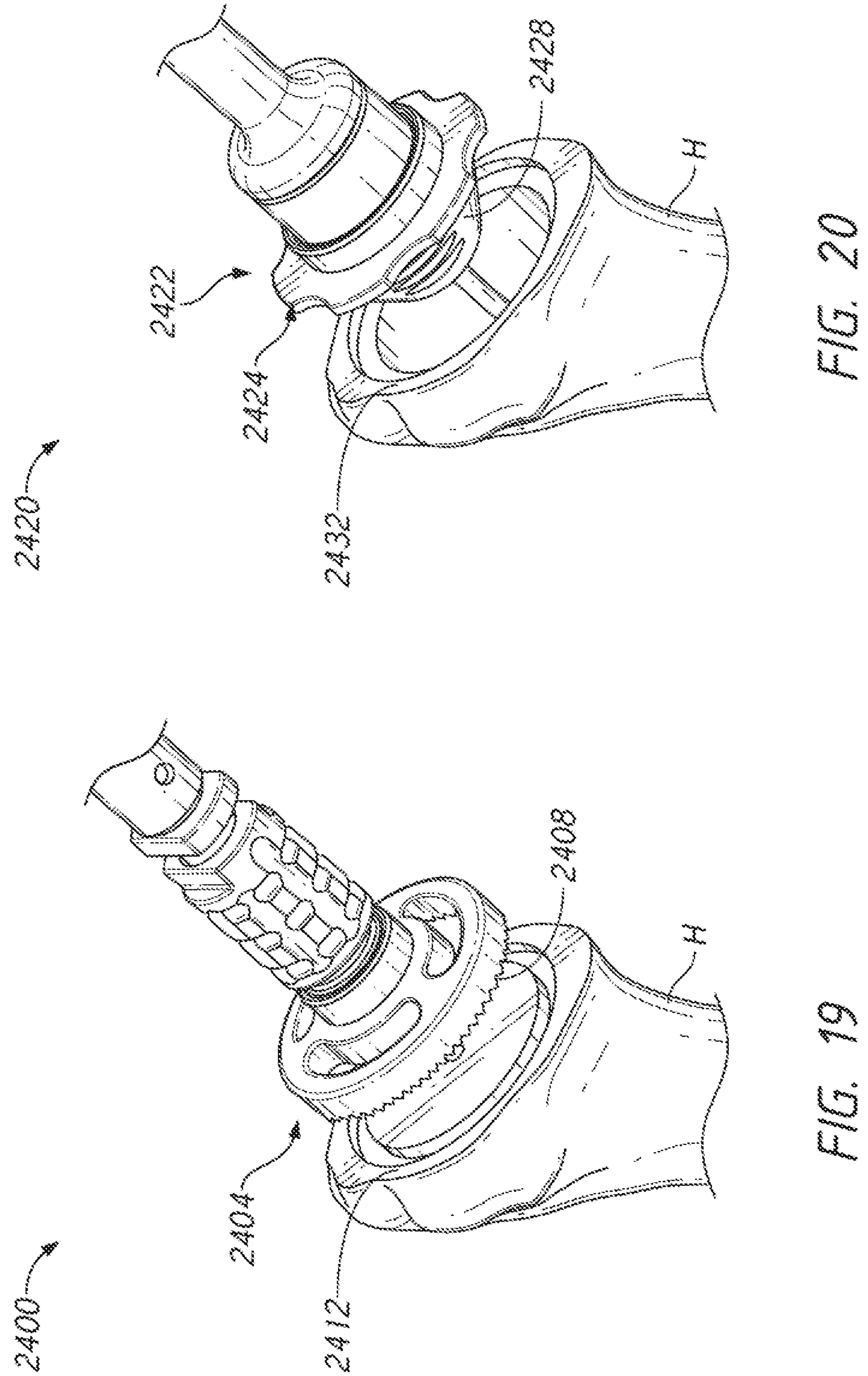
FIG. 19 illustrates an example method in which a portion of the humerus is reamed using a collar reamer to facilitate preparation of a humerus of a patient with relatively soft bone.
FIG. 20 illustrates an example method of compacting the humerus, to form a recess appropriately for a patient with relatively soft bone.

FIGS. 19-20 shows an example of treating a patient with softer than normal bone. In a collar reaming step 2400 a surgeon can form an annular channel 2412 in the resected humerus H. The annular channel 2412 can be in the location and in the size of the outermost reamed area that would be formed in the reaming step 1600. The surface formed in the collar reaming step 2400 is generally configured to mate with the bone compression surface 1250 or with the collar of the stemless anchors 103, 203, 303, 503. A collar reamer 2404 can be provided to form the annular channel 2412. The collar reamer 2404 can be similar to the reaming head 1604 but can omit the inner and distal cutting features, while retaining the annular reaming teeth 2408. As a result, the collar reamer 2404 leaves an area of the resection surface located radially inward of the annular channel 2412 generally unaffected or unreamed. After the annular channel 2412 has been prepared a compacting step 2420 can be performed. The compacting step 2420 can be similar to the blazing step 1900 in that the process involves an axial pressing of a compactor 2422 into the cancellous bone inward of the annular channel 2412. The compactor 2422 can include a depth stop 2424 configured to abut the annular channel 2412 when the compactor 2422 is fully inserted. The depth stop 2424 can include tabs or flanges at opposite sides of the periphery of the proximal end of the compactor 2422. The depth stop 2424 can extend entirely around the periphery of the proximal end of the compactor 2422 in some examples. The compactor 2422 can have a compacting profile 2428 projecting distally of the depth stop 2424 to a distal end of the compactor 2422. The compacting profile 2428 can create a compacted recess close in volume to the recess resulting from the reaming step 1600, e.g., slightly smaller than the blazer 1904 to allow the blazing step 1900 to complete the forming of the recess for receiving the trial anchor 2154 in the process flow above. In another example, the compacting profile 2428 is generally the same as the profile of the blazer 1904 such that the compacting step 2420 can be considered to combine the preparation of the inner area accomplished by the resection step 1500 with the blazing step 1900 into a single step of compacting. The soft bone patient method can continue with the trial step 2150 and the rest of the steps set forth above.

B. Dual Use Surgical Instruments

As discussed above, one advantage of various kits and systems disclosed herein is that multiple different types of humeral anchors can be implanted using shared instrumentation. Examples of shared instrumentation are discussed below.

1. Stem and Stemless Impactor-Inserter

As discussed above, a bone anchor, stemmed and/or stemless, may include one or more interfacing features, such as blind holes, configured to engage a tool and enable insertion of the bone anchor (e.g., stemless or stemmed humeral anchor) into the bone. FIGS. 11A-11D illustrate an inserter 2500 configured to position a bone anchor, stemmed and/or stemless, into the bone. As discussed in more detail below, the inserter 2500 is configured to receive impaction forces, for example from a mallet, to properly insert the bone anchor into the bone. The proximal surface of the bone anchor takes most of the impaction force via direct contact with a distal surface 2503 of inserter 2500.

The inserter 2500 may include an elongate body 2505. The elongate body 2505 may generally extend from a first or proximal end 2502 of the inserter 2500 to a second or distal end 2504 of the inserter 2500. The elongate body 2505 may include an interfacing feature 2514 at the second end 2504 of the inserter 2500. The interfacing feature 2514 may be configured engage the inserter interface of a bone anchor. For example, the interfacing feature 2514 may be a stationary peg that is fixed with respect to the remainder of the inserter 2500 and does not move (see FIG. 11B).

The inserter 2500 may also include a moveable assembly 2506 (see FIG. 11D) coupled with the elongate body 2505. The moveable assembly 2506 may include a handle 2508 disposed between the first end 2502 and the second end 2504 of the inserter 2500. The handle 2508 may be coupled, for example pivotably coupled, with the elongate body 2505 at pivot location 2518.

Figure 11B:
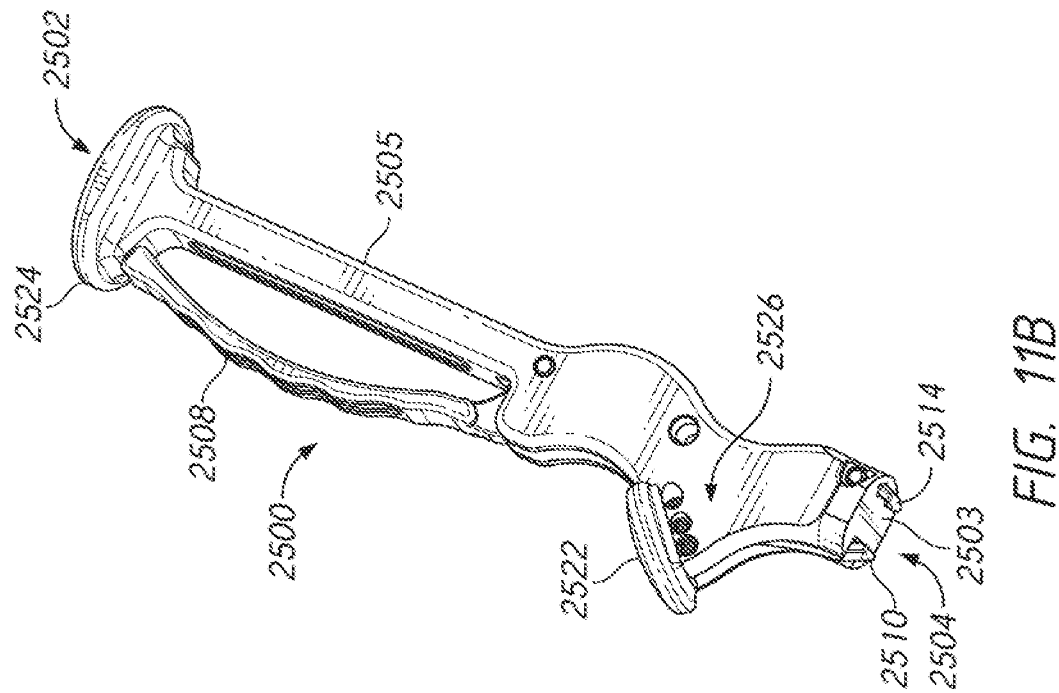
FIGS. 11A-11D illustrate an example of an inserter configured to position a humeral anchor into the humerus.
Figure 11A:
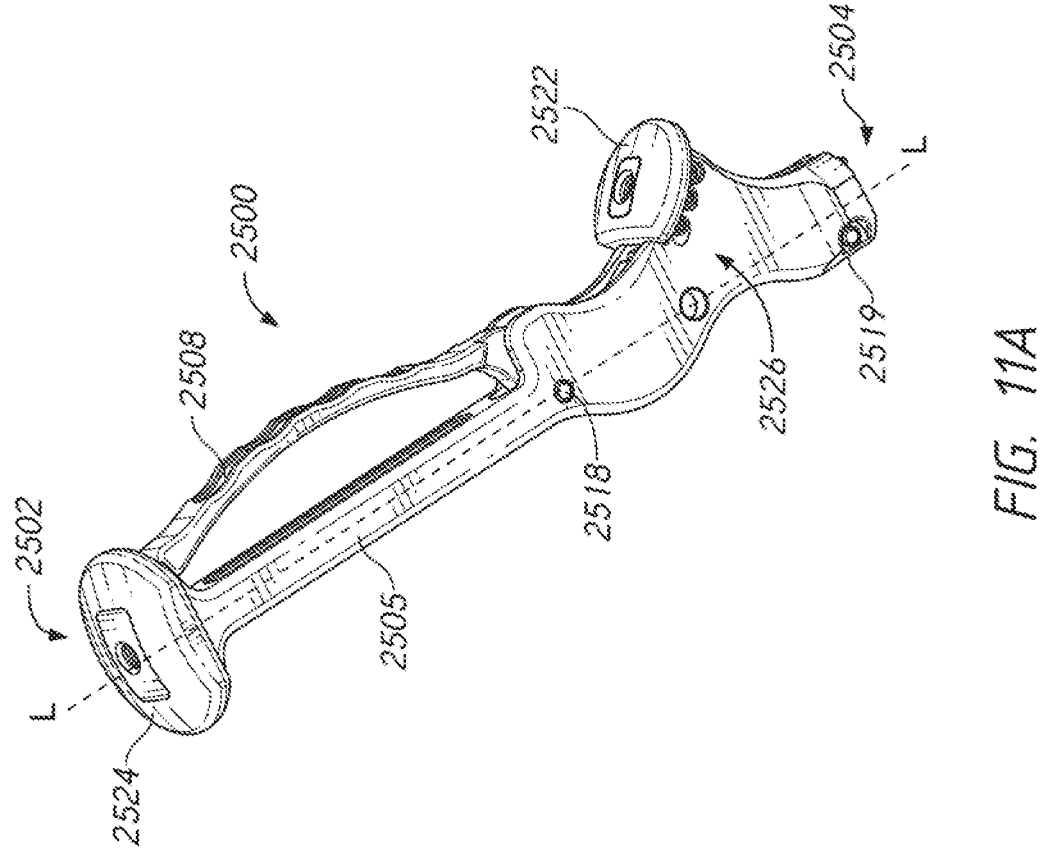
Figure 11D:
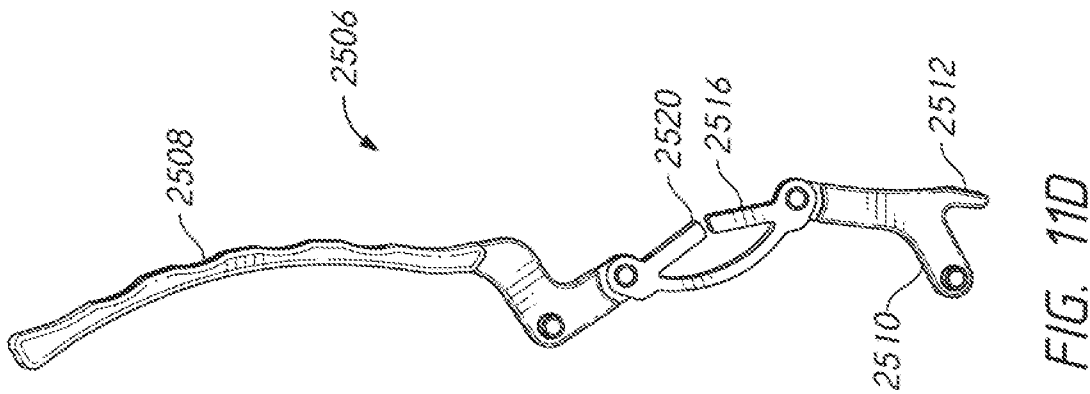
Figure 11C:
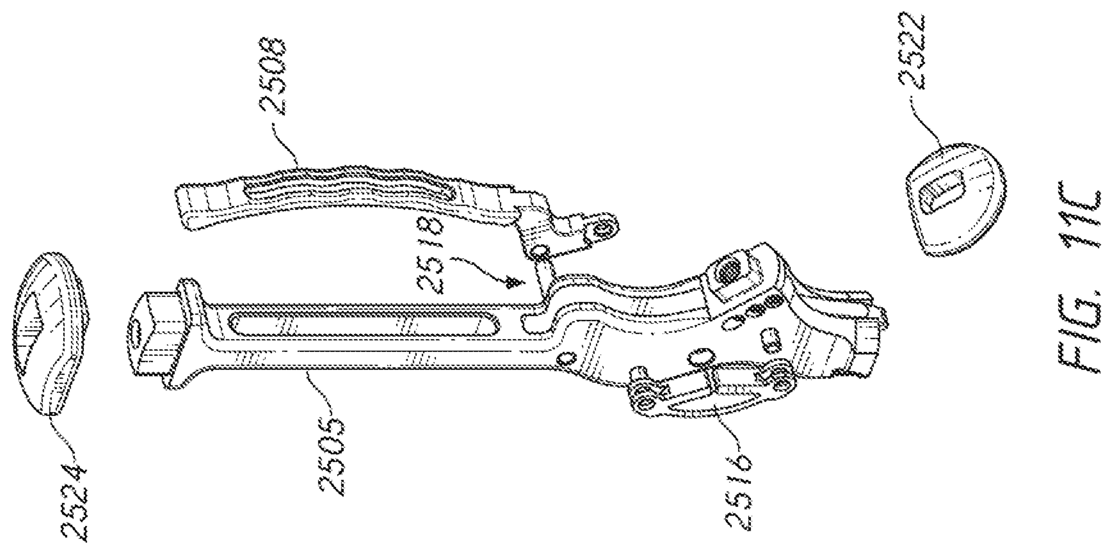

As shown in FIG. 11D, the moveable assembly 2506 may also include a bone anchor interface 2510 disposed at the second end 2504 of the inserter 2500. The bone anchor interface 2510 may be coupled, for example pivotably coupled, with the elongate body 2505 at pivot location 2519. The bone anchor interface 2510 may include an interfacing feature 2512 configured to engage the inserter interface of a bone anchor. For example, the interfacing feature 2512 may be a peg configured to interface with a blind hole on the bone anchor. The converging angle of the interfacing feature 2512 with respect to the interfacing feature 2514 draws the bone anchor against the distal surface 2503 of the inserter 2500, which also serves to better distribute impaction forces across a larger surface area of the proximal surface of the bone anchor.

The handle 2508 may be directly or indirectly coupled to the bone anchor interface 2510. For example, the handle 2508 may be indirectly coupled to the bone anchor interface 2510 by a spring linkage 2516. The spring linkage 2516 may have an arcuate portion and a spring gap 2520. The spring linkage 2516 may be indirectly coupled to the elongate body 2505 by the handle 2508 and/or the bone anchor interface 2510 without a direct connection between the spring linkage 2516 and the elongate body 2505.

The handle 2508 is configured to move the bone anchor interface 2510 between a first configuration and a second configuration. A proximal end of the handle 2508 is free to move relative to the elongate body 2505. The transition between the first configuration and the second configuration may include rotation and/or translation of the interfacing feature 2512 with respect to elongate body 2505. For example, actuating (e.g., pivoting) the handle 2508 toward the elongate body 2505 may move the bone anchor interface 2510 from the first configuration to the second configuration, while releasing the handle 2508 may move the bone anchor interface 2510 back to the first configuration. In the second configuration, the interfacing feature 2512 is rotated and at least partially retracted with respect to a distal surface 2503 of the inserter 2500. In this position, the surgeon may engage the inserter interface of the bone anchor. While the interfacing feature 2512 engages the inserter interface of the bone anchor, the handle 2508 may be released (e.g., away from the elongate body 2505) so as to apply a gripping force to the bone anchor. In the first configuration, the spring linkage 2516 has been compressed (e.g. the spring gap 2520 has been slightly closed), and provides a spring force which helps to hold the interfacing feature 2512 closed against the bone anchor.

Inserter 2500 may include at least one impaction head 2522, 2524 configured to receive impaction forces from, for example, a mallet. For example, the inserter 2500 may include a first impaction head 2522 and a second impaction head 2524. The first impaction head 2522 and the second impaction head 2524 may be disposed at different longitudinal positions along the elongate body 2505. For example, the second impaction head 2524 may be disposed at the first end 2502 of the inserter 2500, while the first impaction head 2522 may be positioned closer to the second end 2504 of the inserter 2500.

The first impaction head 2522 may be coupled with the elongate body 2505 and disposed at a first angle relative to the longitudinal axis of the elongate body 2505. When a force is applied to the first impaction head 2522, the impacting force is directed to the stemmed and/or stemless bone anchor in a direction aligned with a longitudinal axis of the bone anchor to embed the bone anchor in the bone. The second impaction head 2524 may be coupled with the elongate body 2505 and disposed at a second angle, different than the first angle, relative to the longitudinal axis of the elongate body 2505. When a force is applied to the second impaction head 2524, the impacting force is directed to the stemmed and/or stemless bone anchor in a direction perpendicular to a resection plane of the bone in which the bone anchor will be embedded. For example, the first impaction head 2522 may be used to insert a stemmed bone anchor and the second impaction head 2524 may be used to insert a stemless bone anchor. In another example, both the first impaction head 2522 and the second impaction head 2524 may be used to embed a stem portion in the bone. As another example, the inserter 2500 may only include the first impaction head 2522.

The first impaction head 2522 may be disposed at an angle relative to the second impaction head 2524 and/or the longitudinal axis L of the elongate body 2505. The first impaction head 2522 may be disposed at an acute angle relative to the second impaction head 2524, for example between about 35 degrees and about 65 degrees to accommodate stemmed bone anchors having an inclination angle between 125 degrees and about 155 degrees. In one example, the first impaction head 2522 may be disposed at a 45 degree angle relative to the second impaction head 2524.

The inserter 2500 may also be configured to receive a retroversion rod. For example, the retroversion rod may be inserted into one of the openings 2526. Each opening may position the retroversion rod at a different angle, corresponding to the desired angle of resection, and allow the surgeon to evaluate the version. If the proximal bone resection was not accurate or for other reasons dictated by surgeon judgment, the surgeon can modify the resection plane.

The inserter 2500 may form part of a kit including a stemless bone anchor and/or a stemmed bone anchor. The stemless and/or stemmed bone anchor may include any of the features of the implants described above. The bone anchor interface 2510 may be configured to engage the inserter interface of the stemless bone anchor and/or the inserter interface of the stemmed bone anchor.

The kit may include a first inserter and a second inserter. Each of the first inserter and the second inserter may include any of the features described above with respect to the inserter 2500. In the first inserter, the first impaction head and the second impaction head may be disposed at a first angle relative to each other. In the second inserter, the first impaction head and the second impaction head may be disposed at a second angle relative to each other. The second angle may be different from the first angle. One of the first inserter and the second inserter may be selected based on the angle at which the resection is formed in the bone.

In use, the same inserter 2500 may engage the inserter interface of a first, stemless bone anchor or the inserter interface of a second, stemmed bone anchor. The stemless and/or stemmed bone anchor may include any of the features of the implants described above. For example, the inserter 2500 may engage the inserter interface of the stemless bone anchor and advance the stemless bone anchor into bone matter exposed at a resection of a bone. When advancing the stemless bone anchor, a force may be applied to the second impaction head 2524 of the inserter 2500 to apply a force perpendicular to the resection plane of the bone.

The same inserter 2500 may engage the inserter interface of the stemmed bone anchor and advance the stemmed bone anchor to position the stem of the bone anchor in a medullary canal of the bone. When advancing the stemmed bone anchor, a force may be applied to the first impaction head 2522 of the inserter 2500 to apply a force aligned with a longitudinal axis of the stemmed bone anchor to embed the stem in the bone.

2. Reamer for Preparation of Humerus for Stem and Stemless Anchors

As discussed above, the kit 100 can include stemless humeral anchors and humeral anchors with stems. Proximal or metaphyseal portions of these anchors can have the same or similar structures. For example, the proximal end 239 of the humeral anchor 203 can have an overhanging surface opposite the proximal face of the anchor. The overhanging surface can rest on resected bone, e.g., on cancellous bone of the humerus. Similarly, the bone compression surface 1250 of the humeral anchor 1200 can be provided to overhang the same bone surface or portion. The shared design concepts can advantageously use a shared reamer or a collection of reamers having at least one shared design feature.

As noted above, the reamer head 1800 can have an outer periphery with a distal facing cutting edge configured to form the recessed surface R. The recessed surface R can be formed inward of the cortical wall, as discussed above. The recessed surface R can be configured to receive the overhanging surface of the anchor 203 or the anchor 1200 or another one of the anchors disclosed herein. Additional features of the reamer 1800 and a reamer including the reamer head 1850A are discussed above.

Other reamers that can be used for either stem or stemless humeral anchor preparation are also described herein. For example, the initial reamer 2354 can be used in a progressive reaming method for either stem or stemless preparation. The reamer 2354 can be succeeded by larger reamers and/or by tools for accessing and preparing a humeral intramedullary canal. The reamer 2354 can form the recessed surface R. Also, the collar reamer 2404 can be used to prepare a humerus with soft bone for either a stemless or a stemmed anchor. The collar reamer 2404 can prepare the recessed surface, which can come before providing access to the intramedullary canal through relatively soft bone.

Because the kit 100 includes reamers and other instruments that can be used with more than one type of humeral anchor, e.g., with a stemmed and a stemless anchor, the kit is less complex and also less costly than a kit requiring specialized reamers and instruments for each of the stemmed and stemless anchors. Also, given that tools are sometimes discarded after a surgery rather than reused, this approach reduces waste and inefficiencies in the provision of the surgery to the patient. This provides multiple advantages given the cost of such procedures.

Terminology

Although certain embodiments have been described herein, the implants and methods described herein can interchangeably use any articular component, as the context may dictate.

As used herein, the relative terms "proximal" and "distal" shall be defined from the perspective of the implant. Thus, proximal refers to the direction of the articular component and distal refers to the direction of an anchor component, such as a stem of a humeral anchor or a thread or porous surface or other anchoring structure of a stemless anchor when the implant is assembled.

Conditional language, such as "can," "could," "might," or "may" unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1" includes "1." Phrases preceded by a term such as "substantially," "generally," and the like include the recited phrase and should be interpreted based on the circumstances (e.g., as much as reasonably possible under the circumstances). For example, "substantially spherical" includes "spherical." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Although certain embodiments and examples have been described herein, it should be emphasized that many variations and modifications may be made to the humeral head assembly shown and described in the present disclosure, the elements of which are to be understood as being differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, it will be understood by those skilled in the art that the scope of the inventions extends beyond the specifically disclosed embodiments to any and all embodiments having equivalent elements, modifications, omissions, combinations or sub-combinations of the specific features and aspects of the embodiments (e.g., of aspects across various embodiments), adaptations and/or alterations, and uses of the inventions as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "coupling a glenoid guide with the glenoid rim" include "instructing coupling of a glenoid guide with a glenoid rim."

What is claimed is:

1. A method of manufacturing a humeral resection guide comprising a cutting block and a boom extending away from the cutting surface of the cutting block at an obtuse angle, the method comprising:

for each humerus of a plurality of humeruses, adjusting the boom relative to a handle assembly such that the cutting block is disposed at a target cut depth for that humerus;

for each humerus of the plurality of humeruses, determining a target location along a length of the boom to which the handle assembly is connected when the cutting block is disposed at the target cut depth by measuring a distance from an end of the boom to a cross arm of the handle assembly;

determining a range of target locations along the length of the boom based at least in part on the determined target locations for the plurality of humeruses; and providing a cut depth indicator on the boom at a target region of the boom based at least in part on the determined range of target locations, the cut depth indicator comprising a plurality of parallel lines extending in a direction perpendicular to the length of the boom and spaced apart along the length of the boom.

2. The method of claim 1, wherein providing the cut depth indicator comprises providing a plurality of markings spaced apart along the length of the boom.

3. The method of claim 1, wherein the cutting block has a plurality of pin holes extending through a side surface of the cutting block to an opposing side surface of the cutting block.

4. The method of claim 1, wherein the cutting block has a plurality of grooves extending through a side surface of the cutting block to an opposing side surface of the cutting block.

5. A method of surgically altering a humerus using a humeral resection guide comprising a cutting block and a boom extending away from the cutting block, the method comprising:

orienting a side surface of the cutting block to face an exterior surface of the humerus; and adjusting the boom relative to a handle using a cut depth indicator on the boom to position the cutting block at a target cut depth by measuring a distance from an end of the boom to a cross arm of the handle, the cut depth indicator comprising a plurality of parallel lines extending in a direction perpendicular to the length of the boom and spaced apart along the length of the boom.

6. The method of claim 5, further comprising a step of further adjusting the boom relative to the handle based at least in part on a patient anatomy.

7. The method of claim 5, further comprising cutting through the humerus at the target cut depth.

8. The method of claim 5, wherein the cutting block has a plurality of pin holes extending through a side surface of the cutting block to an opposing side surface of the cutting block.

9. The method of claim 5, wherein the cutting block has a plurality of grooves extending through a side surface of the cutting block to an opposing side surface of the cutting block.

* * * * *